(12) United States Patent
Ni et al.

(10) Patent No.: US 11,986,674 B2
(45) Date of Patent: *May 21, 2024

(54) RADIATION THERAPY SYSTEM AND METHOD

(71) Applicant: SHANGHAI UNITED IMAGING HEALTHCARE CO., LTD., Shanghai (CN)

(72) Inventors: Cheng Ni, Shanghai (CN); Xingen Yu, Shanghai (CN); Yanfang Liu, Shanghai (CN); Jingjie Zhou, Shanghai (CN); Jianfeng Liu, Shanghai (CN); Li Wang, Shanghai (CN); Peng Wang, Shanghai (CN); Yangyang Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 427 days.

This patent is subject to a terminal disclaimer.

(21) Appl. No.: 17/216,665

(22) Filed: Mar. 29, 2021

(65) Prior Publication Data

US 2021/0213305 A1 Jul. 15, 2021

Related U.S. Application Data

(63) Continuation of application No. 16/298,471, filed on Mar. 11, 2019, now Pat. No. 10,960,229, which is a
(Continued)

(51) Int. Cl.
*A61N 5/10* (2006.01)
*A61B 5/055* (2006.01)
(Continued)

(52) U.S. Cl.
CPC ............ *A61N 5/1049* (2013.01); *A61B 5/055* (2013.01); *A61N 5/1045* (2013.01);
(Continued)

(58) Field of Classification Search
CPC .... A61B 5/055; A61N 5/1049; A61N 5/1045; A61N 5/1081; G01R 33/3403; G01R 33/4808
See application file for complete search history.

(56) References Cited

U.S. PATENT DOCUMENTS 8,384,387 B1 2/2013 Damadian et al.
8,487,269 B2 7/2013 Amies et al.
(Continued)

FOREIGN PATENT DOCUMENTS

AU 2014271351 A1 1/2015
AU 2016201333 B2 9/2017
(Continued)

OTHER PUBLICATIONS

First Office Action in Chinese Application No. 201880060517.6 dated Feb. 3, 2021, 25 pages.
(Continued)

*Primary Examiner* — Baisakhi Roy
(74) *Attorney, Agent, or Firm* — METIS IP LLC

(57) ABSTRACT

The present disclosure relates to a system and a method. The system may include a magnetic resonance imaging (MRI) apparatus configured to acquire MRI data with respect to a region of interest (ROI) and a therapeutic apparatus configured to apply therapeutic radiation to at least one portion of the ROI. The MRI apparatus may include a plurality of main magnetic coils arranged coaxially along an axis, a plurality of shielding magnetic coils arranged coaxially along the
(Continued)

axis, and a cryostat in which the plurality of main magnetic coils and the plurality of shielding magnetic coils are arranged.

19 Claims, 38 Drawing Sheets

Related U.S. Application Data continuation of application No. PCT/CN2018/115394, filed on Nov. 14, 2018.

(51) Int. Cl.
*G01R 33/34* (2006.01)
*G01R 33/48* (2006.01)
*G21K 5/04* (2006.01)
*H05H 7/22* (2006.01)

(52) U.S. Cl.
CPC ....... *A61N 5/1081* (2013.01); *G01R 33/3403* (2013.01); *G01R 33/4808* (2013.01); *G21K 5/04* (2013.01); *H05H 7/22* (2013.01); *A61N 2005/1055* (2013.01); *A61N 2005/1091* (2013.01); *A61N 2005/1094* (2013.01)

(56) References Cited

U.S. PATENT DOCUMENTS

| | | | |
|---|---|---|---|
| 8,788,016 B2 | 7/2014 | Roell et al. | |
| 8,836,332 B2 | 9/2014 | Shvartsman et al. | |
| 8,983,573 B2 | 3/2015 | Carlone et al. | |
| 9,421,398 B2* | 8/2016 | Shvartsman | G01R 33/4808 |
| 9,526,918 B2* | 12/2016 | Kruip | A61B 5/055 |
| 10,463,883 B2* | 11/2019 | Shvartsman | G01R 33/421 |
| 10,543,380 B2* | 1/2020 | Uhlemann | A61N 5/1071 |
| 10,960,229 B2* | 3/2021 | Ni | G21K 5/04 |
| 11,633,625 B2* | 4/2023 | Wang | A61B 5/055 |
| | | | 324/307 |
| 2006/0151195 A1* | 7/2006 | Donazzi | H01B 9/023 |
| | | | 174/110 R |
| 2008/0208036 A1 | 8/2008 | Amies et al. | |
| 2009/0149735 A1 | 6/2009 | Fallone et al. | |
| 2010/0114276 A1 | 5/2010 | Min et al. | |
| 2010/0176811 A1 | 7/2010 | Tsuda | |
| 2011/0196226 A1 | 8/2011 | Gross et al. | |
| 2011/0196227 A1 | 8/2011 | Gross et al. | |
| 2011/0218420 A1 | 9/2011 | Carlone et al. | |
| 2011/0260729 A1 | 10/2011 | Carlone et al. | |
| 2011/0301449 A1 | 12/2011 | Maurer, Jr. | |
| 2012/0150018 A1 | 6/2012 | Yamaya et al. | |
| 2012/0253172 A1 | 10/2012 | Loeffler et al. | |
| 2013/0225975 A1 | 8/2013 | Harvey | |
| 2014/0066755 A1 | 3/2014 | Matteo et al. | |
| 2014/0128719 A1 | 5/2014 | Longfield | |
| 2014/0135615 A1* | 5/2014 | Kruip | A61N 5/1081 |
| | | | 600/411 |
| 2014/0275963 A1 | 9/2014 | Shvartsman et al. | |
| 2015/0065860 A1 | 3/2015 | Shvartsman et al. | |
| 2015/0119625 A1 | 4/2015 | Knox et al. | |
| 2015/0119693 A1 | 4/2015 | Arber et al. | |
| 2015/0209600 A1 | 7/2015 | Overweg | |
| 2015/0217136 A1 | 8/2015 | Stanescu et al. | |
| 2015/0224341 A1 | 8/2015 | Vahala et al. | |
| 2016/0114192 A1 | 4/2016 | Lachaine et al. | |
| 2016/0136456 A1* | 5/2016 | Jonas | G01R 33/3815 |
| | | | 62/51.1 |
| 2016/0146911 A1 | 5/2016 | Chmielewski et al. | |
| 2016/0213951 A1 | 7/2016 | Uhlemann et al. | |
| 2016/0256712 A1* | 9/2016 | Vahala | A61N 5/1039 |
| 2016/0263400 A1 | 9/2016 | Calvert | |
| 2018/0251333 A1 | 9/2018 | Knierim et al. | |
| 2019/0219650 A1 | 7/2019 | Shvartsman et al. | |
| 2019/0274649 A1 | 9/2019 | Fahrig et al. | |
| 2020/0246637 A1 | 8/2020 | Wang et al. | |
| 2021/0046330 A1 | 2/2021 | Kleven | |
| 2021/0162236 A1 | 6/2021 | Shvartsman et al. | |

FOREIGN PATENT DOCUMENTS

| | | |
|---|---|---|
| CN | 104161532 A | 11/2014 |
| CN | 105233425 A | 1/2016 |
| EP | 1893290 B1 | 12/2010 |
| EP | 2986340 B1 | 11/2016 |
| GB | 2393373 A | 3/2004 |
| KR | 101378447 B1 | 3/2014 |
| KR | 101540940 B1 | 8/2015 |
| KR | 101545171 81 | 8/2015 |
| KR | 101604976 B1 | 3/2016 |
| WO | 2012049466 A1 | 4/2012 |
| WO | 2014144399 A1 | 9/2014 |
| WO | 2014203105 A1 | 12/2014 |
| WO | 2015055473 A1 | 4/2015 |
| WO | 2015169655 A1 | 11/2015 |
| WO | 2015197475 A1 | 12/2015 |
| WO | 2021046675 A1 | 3/2021 |

OTHER PUBLICATIONS

International Search Report in PCT/CN2018/115394 dated Jul. 25, 2019, 5 pages.
Written Opinion in PCT/CN2018/115394 dated Jul. 25, 2019, 4 pages.
International Search Report in PCT/CN2021/138123 dated May 5, 2022, 5 pages.
Written Opinion in PCT/CN2021/138123 dated May 5, 2022, 4 pages.

* cited by examiner

RADIATION THERAPY SYSTEM AND METHOD

CROSS-REFERENCE TO RELATED APPLICATIONS

This application is a Continuation of U.S. application Ser. No. 16/298,471, filed on Mar. 11, 2019, which is a Continuation of International Application No. PCT/CN2018/115394, filed on Nov. 14, 2018, the contents of which is incorporated herein by reference.

TECHNICAL FIELD

The present disclosure generally relates to a radiation therapy system, and more particularly, relates to an image-guided radiation therapy system which combines radiation therapy and magnetic resonance imaging technique.

BACKGROUND

Radiation therapy on a tumor is currently affected by difficulties to track the variation (e.g., motion) of the tumor in different treatment sessions. Nowadays, various imaging techniques may be applied to provide real-time images of the tumor before or within each treatment session. For example, a magnetic resonance imaging (MRI) apparatus may be used in combination with a radiation therapy apparatus to provide MRI images of the tumor. The combination of the MRI apparatus and the radiation therapy apparatus, which forms a therapeutic apparatus, may encounter difficulties in arranging components of the MRI apparatus (e.g., a plurality of main magnetic coils, a plurality of shielding magnetic coils) and components of the radiation therapy apparatus (e.g., a linear accelerator) in a relatively compact space without causing interferences. Therefore, it may be desirable to provide a therapeutic apparatus that provides high therapeutic quality and also has a compact structure as well.

SUMMARY

In a first aspect of the present disclosure, a radiation therapy system is provided. The system may include a magnetic resonance imaging (MRI) apparatus and a radiation therapy apparatus. The MRI apparatus may be configured to acquire MRI data with respect to a region of interest (ROI). The MRI apparatus may include a plurality of main magnetic coils, a plurality of shielding magnetic coils, and an annular cryostat in which the plurality of main magnetic coils and the plurality of shielding magnetic coils are coaxially arranged along an axis of the annular cryostat. The plurality of shielding magnetic coils may be arranged at a larger radius from the axis than the plurality of main magnetic coils. The annular cryostat may include at least one outer wall and at least one inner wall coaxial around the axis. The annular cryostat may include an annular recess between the at least one outer wall and the at least one inner wall. The annular recess may have an opening formed at the at least one outer wall. The radiation therapy apparatus may be configured to apply therapeutic radiation to at least one portion of the ROI. The radiation therapy apparatus may include a linear accelerator, one or more collimation components, a first shielding structure, and at least one second shielding structure. The linear accelerator may be configured to accelerate electrons in an electron beam to produce a photon beam of the therapeutic radiation. The linear accelerator may be at least partially located within the annular recess of the annular cryostat. The one or more collimation components configured to shape the photon beam of the therapeutic radiation. The first shielding structure may be configured to provide magnetic shielding for at least one of the linear accelerator and the one or more collimation components. The at least one second shielding structure may be substantially identical to the first shielding structure, wherein the first shielding structure and the at least one second shielding structure are respectively located at selected circumferential locations within the annular recess.

In some embodiments, the at least one second shielding structure may be located at an opposite circumferential position of the first magnetic shielding structure with respect to the axis.

In some embodiments, the linear accelerator may be at least partially surrounded by the first shielding structure, and the first magnetic shielding structure may provide passive magnetic shielding for the linear accelerator.

In some embodiments, the first shielding structure may form a semi-closed loop around an axis of the linear accelerator.

In some embodiments, the semi-closed loop may include at least two plates arranged along a circumferential direction of the linear accelerator.

In some embodiments, the radiation therapy apparatus may further include two annular magnetic shielding layers, and the first shielding structure may be at least formed by two first magnetic shielding separators connecting the two annular magnetic shielding layers.

In some embodiments, the two annular magnetic shielding layers may be coaxial around the axis.

In some embodiments, the two annular magnetic shielding layers may be arranged along the axis of the annular cryostat and parallel to each other.

In some embodiments, the radiation therapy apparatus may further include an inner magnetic shielding layer and an outer magnetic shielding layer, both of which may be connected to the two annular magnetic shielding layers. The first shielding structure may be formed by the two annular magnetic shielding layers, the inner magnetic shielding layer, the outer magnetic shielding layer, and the two first magnetic shielding separators connecting the two annular magnetic shielding layers.

In some embodiments, the outer magnetic shielding layer may include a plurality of slots, and at least one of the plurality of slots may be located at a position corresponding to one of the two first magnetic shielding separators.

In some embodiments, the at least one second shielding structure may include more than two second shielding structures, and the first shielding structure and the at least one second shielding structure may be evenly distributed within the annular recess.

In some embodiments, the annular cryostat may include at least two chambers and a neck portion, the at least two chambers being connected through the neck portion and in fluid communication with each other, the annular recess being at least defined by the at least two chambers and the neck portion.

In some embodiments, the annular recess may be located between the at least two chambers, and an outermost surface of the neck portion may form an innermost boundary of the annular recess.

In some embodiments, electron beam may move along an electron beam path that is parallel to the axis of the annular cryostat, and the radiation therapy apparatus may further include a target; and a beam deflection unit configured to deflect the electrons from the electron beam onto the target to produce the photon beam of the therapeutic radiation.

In some embodiments, the annular cryostat may include an annular concave structure having an opening formed at the at least one inner wall. The radiation therapy apparatus may further include a multi-leaf collimator (MLC) accommodated in the annular concave structure of the annular cryostat and configured to control a shape of the photon beam of the therapeutic radiation that passes through it.

In some embodiments, one or more of the plurality of main magnetic coils may be arranged to surround the annular concave structure, and the one or more of the plurality of main magnetic coils may have a larger radius from the axis than the rest of the plurality of main magnetic coils.

In some embodiments, the MLC may be connected to the linear accelerator via two or more rods.

In some embodiments, the MLC may be configured to move within the annular concave structure along a sliding structure.

In a second aspect of the present disclosure, a radiation therapy system is provided. The radiation therapy system may include a magnetic resonance imaging (MRI) apparatus configured to acquire MRI data with respect to a region of interest (ROI) and a radiation therapy apparatus configured to apply therapeutic radiation to at least one portion of the ROI. The MRI apparatus may include a plurality of main magnetic coils, a plurality of shielding magnetic coils, and an annular cryostat in which the plurality of main magnetic coils and the plurality of shielding magnetic coils may be coaxially arranged along an axis of the annular cryostat. The plurality of shielding magnetic coils may be arranged at a larger radius from the axis than the plurality of main magnetic coils, the annular cryostat including at least one outer wall and at least one inner wall coaxially around the axis. The annular cryostat may include an annular recess between the at least one outer wall and the at least one inner wall, and the annular recess having an opening formed at the at least one outer wall. The radiation therapy apparatus may include a linear accelerator configured to accelerate electrons in an electron beam along an electron beam path that is parallel to the axis, the linear accelerator being at least partially located within the annular recess of the cryostat; a target; and a beam deflection unit configured to deflect the electrons from the electron beam onto the target to produce a photon beam of the therapeutic radiation.

In some embodiments, the annular cryostat may include at least two chambers arranged along the axis of the annular cryostat, the at least two chambers being connected through a neck portion and in fluid communication with each other, the annular recess being at least defined by the at least two chambers and the neck portion.

In some embodiments, the annular recess may be located between the at least two chambers, and an outermost surface of the neck portion may form an innermost boundary of the annular recess.

In some embodiments, the radiation therapy apparatus may include a first shielding structure configured to provide magnetic shielding for the linear accelerator, wherein the first shielding structure may be continuous distributed along a direction of the axis and stretch to cover two ends of the linear accelerator along the direction of the axis.

In some embodiments, the radiation therapy apparatus may further include at least one second shielding structure substantially identical to the first shielding structure, wherein the first shielding structure and the at least one second shielding structure may be respectively located at selected circumferential locations within the annular recess.

In some embodiments, the linear accelerator may be at least partially surrounded by the first shielding structure, and the first magnetic shielding structure may provide passive magnetic shielding for the linear accelerator.

In some embodiments, the first shielding structure may form a semi-closed loop around an axis of the linear accelerator.

In some embodiments, the semi-closed loop may include at least two plates arranged along a circumferential direction of the linear accelerator.

In some embodiments, the radiation therapy apparatus may further include two annular magnetic shielding layers, and the first shielding structure may be at least formed by two first magnetic shielding separators connecting the two annular magnetic shielding layers.

In some embodiments, the two annular magnetic shielding layers may be coaxial around the axis.

In some embodiments, the two annular magnetic shielding layers may be arranged along the axis of the annular cryostat and parallel to each other.

In some embodiments, the radiation therapy apparatus may further include an inner magnetic shielding layer and an outer magnetic shielding layer, both of which may be connected to the two annular magnetic shielding layers, and the first shielding structure may be formed by the two annular magnetic shielding layers, the inner magnetic shielding layer, the outer magnetic shielding layer, and the two first magnetic shielding separators connecting the two annular magnetic shielding layers.

In some embodiments, the outer magnetic shielding layer may include a plurality of slots, and at least one of the plurality of slots may be located at a position corresponding to one of the two first magnetic shielding separators.

In some embodiments, the first shielding structure and the at least one second shielding structure may be evenly distributed within the annular recess.

In some embodiments, the annular cryostat may include an annular concave structure having an opening formed at the at least one inner wall. The radiation therapy apparatus may include a multi-leaf collimator (MLC) accommodated in the annular concave structure of the annular cryostat and configured to control a shape of the photon beam of the therapeutic radiation that passes through it.

In some embodiments, one or more of the plurality of main magnetic coils may be arranged to surround the annular concave structure, and the one or more of the plurality of main magnetic coils may have a larger radius from the axis than the rest of the plurality of main magnetic coils.

In some embodiments, the MLC may be connected to the linear accelerator via two or more rods.

In some embodiments, the MLC may be configured to move within the annular concave structure along a sliding structure.

In a third aspect of the present disclosure, a radiation therapy system is provided. The radiation therapy system may include a magnetic resonance imaging (MRI) apparatus configured to acquire MRI data with respect to a region of interest (ROI), and a radiation therapy apparatus configured to apply therapeutic radiation to at least one portion of the ROI. The MRI apparatus may include a plurality of main magnetic coils; a plurality of shielding magnetic coils; and an annular cryostat in which the plurality of main magnetic coils and the plurality of shielding magnetic coils may be coaxially arranged along an axis of the annular cryostat. The plurality of shielding magnetic coils may be arranged at a larger radius from the axis than the plurality of main magnetic coils. The annular cryostat may include at least one outer wall and at least one inner wall coaxially around the axis. The annular cryostat may include an annular recess having a first opening formed at the at least one outer wall, and an annular concave structure having a second opening formed at the at least one inner wall. The radiation therapy apparatus may include a linear accelerator configured to accelerate electrons in an electron beam to produce a beam of the therapeutic radiation, the linear accelerator being at least partially located within the annular recess of the cryostat; and a multi-leaf collimator (MLC) accommodated in the annular concave structure of the annular cryostat and configured to control a shape of the beam of the therapeutic radiation that passes through it.

In some embodiments, one or more of the plurality of main magnetic coils may be arranged to surround the annular concave structure, and the one or more of the plurality of main magnetic coils may have a larger radius from the axis than the rest of the plurality of main magnetic coils.

In some embodiments, the MLC may be connected to the linear accelerator via two or more rods.

In some embodiments, the MLC may be configured to move within the annular concave structure along a sliding structure.

In some embodiments, the radiation therapy apparatus may include a first shielding structure configured to provide magnetic shielding for the linear accelerator, wherein the first shielding structure is continuous distributed along a direction of the axis and stretches to cover two ends of the linear accelerator along the direction of the axis.

In some embodiments, the radiation therapy apparatus may further include at least one second shielding structure substantially identical to the first shielding structure, wherein the first shielding structure and the at least one second shielding structure are respectively located at selected circumferential locations within the annular recess.

In some embodiments, the linear accelerator may be at least partially surrounded by the first shielding structure, and the first magnetic shielding structure may provide passive magnetic shielding for the linear accelerator.

In some embodiments, the first shielding structure may form a semi-closed loop around an axis of the linear accelerator.

In some embodiments, the semi-closed loop may include at least two plates arranged along a circumferential direction of the linear accelerator.

In some embodiments, the radiation therapy apparatus may further include two annular magnetic shielding layers, and the first shielding structure may be at least formed by two first magnetic shielding separators connecting the two annular magnetic shielding layers.

In some embodiments, the two annular magnetic shielding layers may be coaxial around the axis.

In some embodiments, the two annular magnetic shielding layers may be arranged along the axis of the annular cryostat and parallel to each other.

In some embodiments, the radiation therapy apparatus may further include an inner magnetic shielding layer and an outer magnetic shielding layer, both of which may be connected to the two annular magnetic shielding layers. The first shielding structure may be formed by the two annular magnetic shielding layers, the inner magnetic shielding layer, the outer magnetic shielding layer, and the two first magnetic shielding separators connecting the two annular magnetic shielding layers.

In some embodiments, the outer magnetic shielding layer may include a plurality of slots, and at least one of the plurality of slots may be located at a position corresponding to one of the two first magnetic shielding separators.

In some embodiments, the first shielding structure and the at least one second shielding structure may be evenly distributed within the annular recess.

In some embodiments, the annular cryostat may include at least two chambers and a neck portion, the at least two chambers being connected through the neck portion and in fluid communication with each other, the annular recess being at least defined by the at least two chambers and the neck portion.

In some embodiments, the annular recess may be located between the at least two chambers, and an outermost surface of the neck portion may form an innermost boundary of the annular recess.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Figure 1:
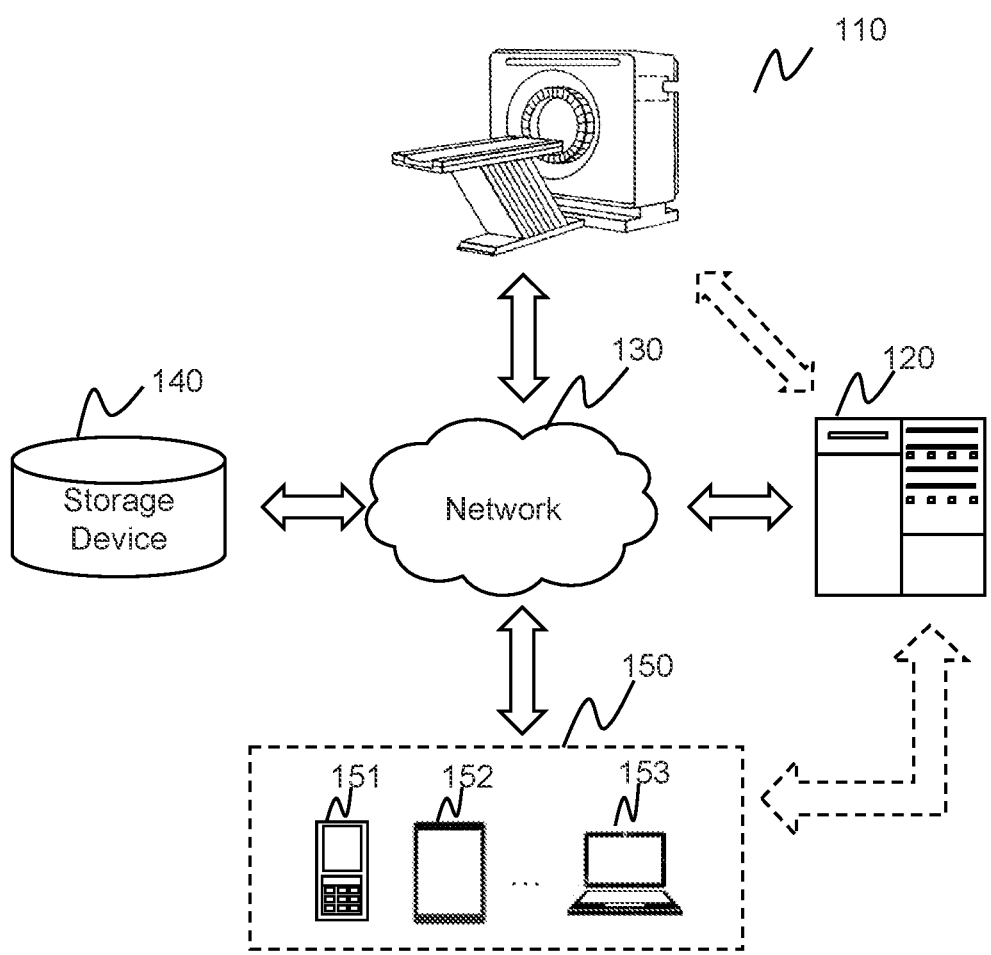
FIG. 1 is a block diagram illustrating an exemplary radiation therapy system according to some embodiments of the present disclosure.

FIG. 1 is a block diagram illustrating an exemplary radiation therapy system 100 according to some embodiments of the present disclosure. In some embodiments, the radiation therapy system 100 may be a multi-modality imaging system including, for example, a positron emission tomography-radiotherapy (PET-RT) system, a magnetic resonance imaging-radiotherapy (MRI-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, one or more processing engines 120, a network 130, a storage device 140, and one or more terminal devices 150. In some embodiments, the therapeutic apparatus 110, the one or more processing engines 120, the storage device 140, and/or the terminal device 150 may be connected to and/or communicate with each other via a wireless connection (e.g., the wireless connection provided by the network 130), a wired connection (e.g., the wired connection provided by the network 130), or any combination thereof.

The therapeutic apparatus 110 may include a magnetic resonance imaging component (hereinafter referred to as "MRI apparatus"). The MRI apparatus may generate image data associated with magnetic resonance signals (hereinafter referred to as "MRI signals") via scanning a subject or a part of the subject. In some embodiments, the subject may include a body, a substance, an object, or the like, or any combination thereof. In some embodiments, the subject may include a specific portion of a body, a specific organ, or a specific tissue, such as head, brain, neck, body, shoulder, arm, thorax, cardiac, stomach, blood vessel, soft tissue, knee, feet, or the like, or any combination thereof. In some embodiments, the therapeutic apparatus 110 may transmit the image data via the network 130 to the one or more processing engines 120, the storage device 140, and/or the terminal device 150 for further processing. For example, the image data may be sent to the one or more processing engines 120 for generating an MRI image, or may be stored in the storage device 140.

The therapeutic apparatus 110 may also include a radiation therapy component (hereinafter referred to as "radiation therapy apparatus"). The radiation therapy apparatus may provide radiation for target region (e.g., a tumor) treatment. The radiation used herein may include a particle ray, a photon ray, etc. The particle ray may include neutron, proton, electron, p-meson, heavy ion, a-ray, or the like, or any combination thereof. The photon ray may include X-ray, y-ray, ultraviolet, laser, or the like, or any combination thereof. For illustration purposes, a radiation therapy apparatus associated with X-ray may be described as an example.

In some embodiments, the therapeutic apparatus 110 may generate a certain dose of X-rays to perform radiotherapy under the assistance of the image data provided by the MRI apparatus. For example, the image data may be processed to locate a tumor and/or determine the dose of X-rays.

The one or more processing engines 120 may process data and/or information obtained from the therapeutic apparatus 110, the storage device 140, and/or the terminal device 150. For example, the one or more processing engines 120 may process image data and reconstruct at least one MRI image based on the image data. As another example, the one or more processing engines 120 may determine the position of the treatment region and the dose of radiation based on the at least one MRI image. The MRI image may provide advantages including, for example, superior soft-tissue contrast, high resolution, geometric accuracy, which may allow accurate positioning of the treatment region. The MRI image may be used to detect the variance of the treatment region (e.g., a tumor regression or metastasis) during the time when the treatment plan is determined and the time when the treatment is carried out, such that an original treatment plan may be adjusted accordingly. The original treatment plan may be determined before the treatment commences. For instance, the original treatment plan may be determined at least one day, or three days, or a week, or two weeks, or a month, etc., before the treatment commences.

In the original or adjusted treatment plan, the dose of radiation may be determined according to, for example, synthetic electron density information. In some embodiments, the synthetic electron density information may be generated based on the MRI image.

In some embodiments, the one or more processing engines 120 may be a single processing engine that communicates with and process data from the MRI apparatus and the radiation therapy apparatus of the therapeutic apparatus 110. Alternatively, the one or more processing engines 120 may include at least two processing engines. One of the at least two processing engines may communicate with and process data from the MRI apparatus of the therapeutic apparatus 110, and another one of the at least two processing engines may communicate with and process data from the radiation therapy apparatus of the therapeutic apparatus 110. In some embodiments, the one or more processing engines 120 may include a treatment planning system. The at least two processing engines may communicate with each other.

In some embodiments, the one or more processing engines 120 may be a single server or a server group. The server group may be centralized or distributed. In some embodiments, the one or more processing engines 120 may be local to or remote from the therapeutic apparatus 110. For example, the one or more processing engines 120 may access information and/or data from the therapeutic apparatus 110, the storage device 140, and/or the terminal device 150 via the network 130. As another example, the one or more processing engines 120 may be directly connected to the therapeutic apparatus 110, the terminal device 150, and/or the storage device 140 to access information and/or data. In some embodiments, the one or more processing engines 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the one or more processing engines 120, the storage device 140, or the terminal device 150) may communicate information and/or data with one or more other components of the radiation therapy system 100 via the network 130. For example, the one or more processing engines 120 may obtain image data from the therapeutic apparatus 110 via the network 130. As another example, the one or more processing engines 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the one or more processing engines 120 and/or the terminal device 150. In some embodiments, the storage device 140 may store data and/or instructions that the one or more processing engines 120 may execute or use to perform exemplary methods described in the present disclosure. In some embodiments, the storage device 140 may include a mass storage device, a removable storage device, a cloud based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the one or more processing engines 120 or the terminal device 150). One or more components of the radiation therapy system 100 may access the data or instructions stored in the storage device 140 via the network 130. In some embodiments, the storage device 140 may be part of the one or more processing engines 120.

The terminal device 150 may be connected to and/or communicate with the therapeutic apparatus 110, the one or more processing engines 120, and/or the storage device 140. For example, the one or more processing engines 120 may acquire a scanning protocol from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistance (PDA), a gaming device, a navigation device, a point of sale (POS) device, a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the one or more processing engines 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the one or more processing engines 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the one or more processing engines 120 may be integrated into the therapeutic apparatus 110. However, those variations and modifications do not depart the scope of the present disclosure.

Figure 2:
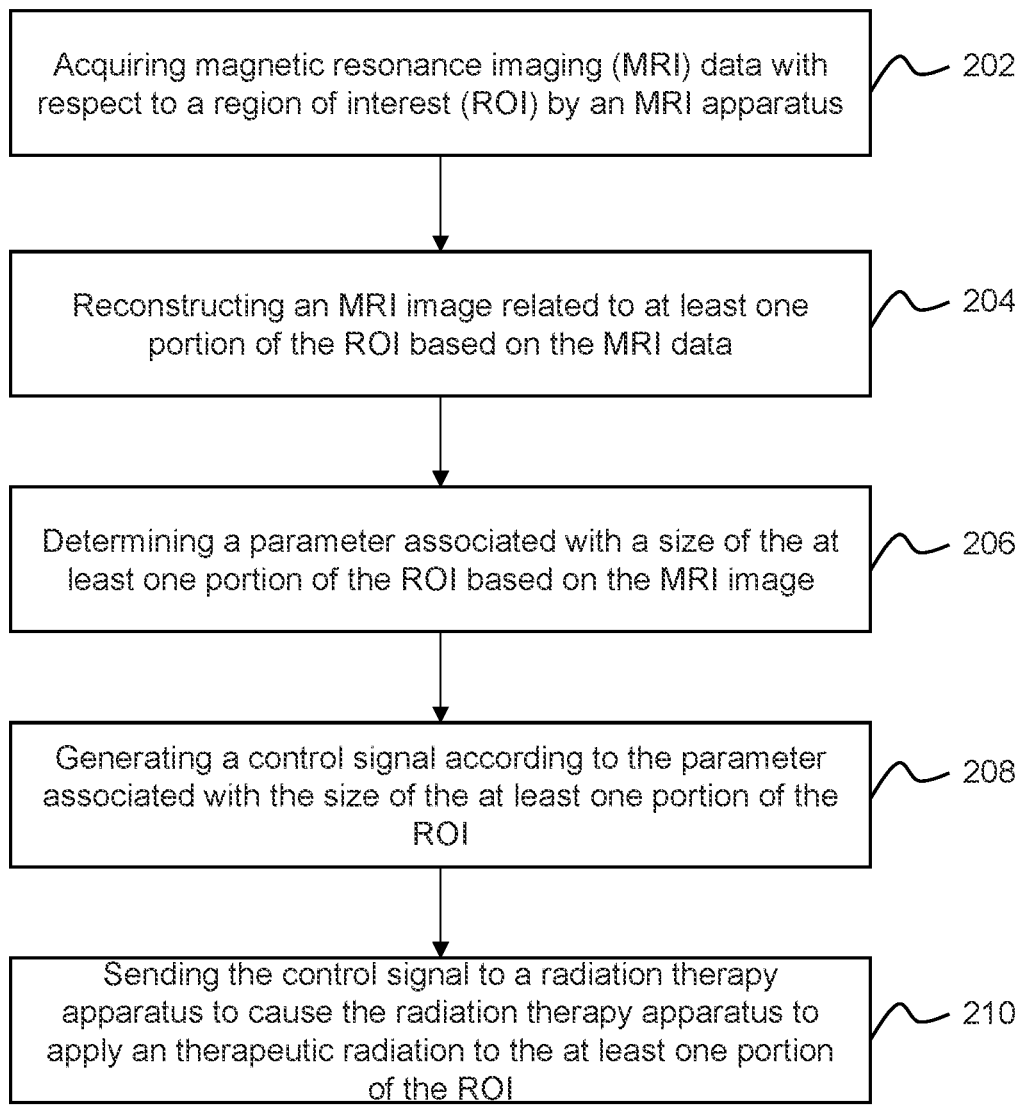
FIG. 2 is a flowchart illustrating an exemplary process for applying an therapeutic radiation in a radiation therapy system according to some embodiments of the present disclosure.

FIG. 2 is a flowchart of an exemplary process 200 for applying a therapeutic radiation by a radiation therapy system according to some embodiments of the present disclosure. In some embodiments, one or more operations of the process 200 illustrated in FIG. 2 may be implemented in the radiation therapy system 100 illustrated in FIG. 1. For example, the process 200 illustrated in FIG. 2 may be stored in the storage device 140 in the form of instructions, and invoked and/or executed by the one or more processing engines 120 illustrated in FIG. 1. For illustration purposes, the implement of the process 200 in the one or more processing engines 120 is described herein as an example. It shall be noted that the process 200 can also be similarly implemented in the terminal device 150.

In 202, the one or more processing engines 120 may acquire magnetic resonance imaging (MRI) data with respect to a region of interest (ROI) by an MRI apparatus. The MRI data may be MR signals received by an RF coil from a subject. More detailed description related to the MR signals may be found elsewhere in the present disclosure at, for example, FIG. 3 and the description thereof.

In some embodiments, an ROI may refer to a treatment region associated with a tumor. The treatment region may be a region of a subject (e.g., a body, a substance, an object). In some embodiments, the ROI may be a specific portion of a body, a specific organ, or a specific tissue, such as head, brain, neck, body, shoulder, arm, thorax, cardiac, stomach, blood vessel, soft tissue, knee, feet, or the like, or any combination thereof.

In 204, the one or more processing engines 120 may reconstruct an MRI image related to at least one portion of the ROI based on the MRI data. The MRI image may be reconstructed as a distribution of atomic nuclei inside the subject based on the MRI data. Different kinds of imaging reconstruction techniques for the image reconstruction procedure may be employed. Exemplary image reconstruction techniques may include Fourier reconstruction, constrained image reconstruction, regularized image reconstruction in parallel MRI, or the like, or a variation thereof, or any combination thereof.

The MRI image may be used to determine a therapeutic radiation to a tumor. For example, the one or more processing engines 120 may determine the position of the tumor and the dose of radiation according to the MRI image. In some embodiments, it may take at least several minutes to reconstruct an MRI image representing a large imaging region. In some embodiments, in order to generate the MRI image during a relative short time period (e.g., every second), the one or more processing engines 120 may reconstruct an initial image representing a smaller imaging region (e.g., at least one portion of the ROI) compared to that of the MRI image representing a large imaging region, and then combine the initial image with the MRI image representing a large imaging region. For example, the one or more processing engines 120 may replace a portion of the MRI image representing a large imaging region related to the ROI with the initial image. The MRI image representing a large imaging region may include information of non-ROI (e.g., a healthy tissue) near the ROI and that of the ROI. In some embodiments, the MRI image representing a large imaging region may be acquired and reconstructed before the therapeutic radiation on the tumor. For example, the MRI image representing a large imaging region may be acquired less than 1 day, or half a day, or 6 hours, or 3 hours, or 1 hour, or 45 minutes, or 30 minutes, or 20 minutes, or 15 minutes, or 10 minutes, or 5 minutes, etc., before the radiation source starts emitting a radiation beam for treatment. In some embodiments, the MRI image representing a large imaging region may be obtained from a storage device in the radiation therapy system 100, such as the storage device 140.

In 206, the one or more processing engines 120 may determine a parameter associated with a size of the at least one portion of the ROI based on the MRI image. In some embodiments, the parameter associated with a size of the at least one portion of the ROI may include the size of the cross section of a tumor which has the maximum area and is perpendicular to the direction of the radiation beams impinging on the at least one portion of the ROI. In some embodiments, the parameter associated with a size of the at least one portion of the ROI may indicate the shape of the cross section of the tumor. For example, the parameter associated with a size of at least one portion of the ROI may indicate that the shape of the cross section of the tumor is circle, and further indicate the diameter of the circle. In some embodiments, to determine the parameter associated with a size of at least one portion of the ROI, the one or more processing engines 120 may extract texture information from the MRI image, and determine texture features that are indicative of the ROI by identifying frequent texture patterns of the ROI in the extracted texture information. Then, the one or more processing engines 120 may measure the size of the region which includes the texture features in the MRI image, and determine the parameter associated with the size of the ROI.

In 208, the one or more processing engines 120 may generate a control signal according to the parameter associated with the size of at least one portion of the ROI. The control signal may be dynamically adjusted based on the plurality of MRI images taken at different time points. In some embodiments, the control signal may include parameters associated with the therapeutic radiation on the tumor. For example, the control signal may include the dosage of X-rays and a duration of the radiation beam. For another example, the control signal may include parameters of multi-leaf collimator (MLC) that determines the shape of the radiation beam projected on the subject. The MLC may include a plurality of individual leaves of high atomic numbered materials (e.g., tungsten) moving independently in and out of the path of the radiation beam. In some embodiments, the control signal may include parameters associated with movements of one or more components of a radiation therapy apparatus. For example, the control signal may include a parameter associated with one or more positions of a radiation source of the radiation therapy apparatus (e.g., the radiation therapy apparatus in the therapeutic apparatus 110, a radiation therapy apparatus 300). For another example, the control signal may include a parameter associated with a height or a position of a platform of the radiation therapy apparatus (e.g., a location of the platform 308 of the treatment table 330 along an axis of the magnetic body 302) to properly position a patient so that the treatment region (e.g., a cancerous tumor or lesion) in the patient may properly receive the radiation beam from the radiation therapy apparatus.

In 210, the one or more processing engines 120 may send the control signal to a radiation therapy apparatus to cause the radiation therapy apparatus to apply the therapeutic radiation. During the therapeutic radiation, the radiation source of the radiation therapy apparatus may rotate, and the dosage of X-rays, duration of radiation beam from a radiation source, the shape of MLC and the position of the platform may be varied. In some embodiments, the radiation beam may be emitted only when the radiation source of the radiation therapy apparatus rotates to certain angles (e.g., 60 degrees, 120 degrees, 180 degrees, 240 degrees, 300 degrees, 360 degrees). For example, an intensity modulated radiation therapy (IMRT) may be applied. The radiation source may stop rotating intermittently. The radiation source may rotate to a desired position, pause there, and emit a radiation beam, and then resume to rotate. In some embodiments, the radiation source may rotate continuously, and emit a radiation beam continuously or intermittently. In some embodiments, the radiation source may continuously emit the radiation beam while rotating.

In some embodiments, as described above, a treatment region (e.g., a region including a tumor) may be determined according to the image data acquired from the MRI apparatus. Then a radiation beam may be generated by a radiation source of the radiation therapy apparatus to perform the therapeutic radiation to the treatment region. For example, the dosage of the radiation beam and/or the position of the treatment region may be determined in real-time with the assistance of the MRI apparatus.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 202 and 204 may be performed simultaneously.

Figure 3A:
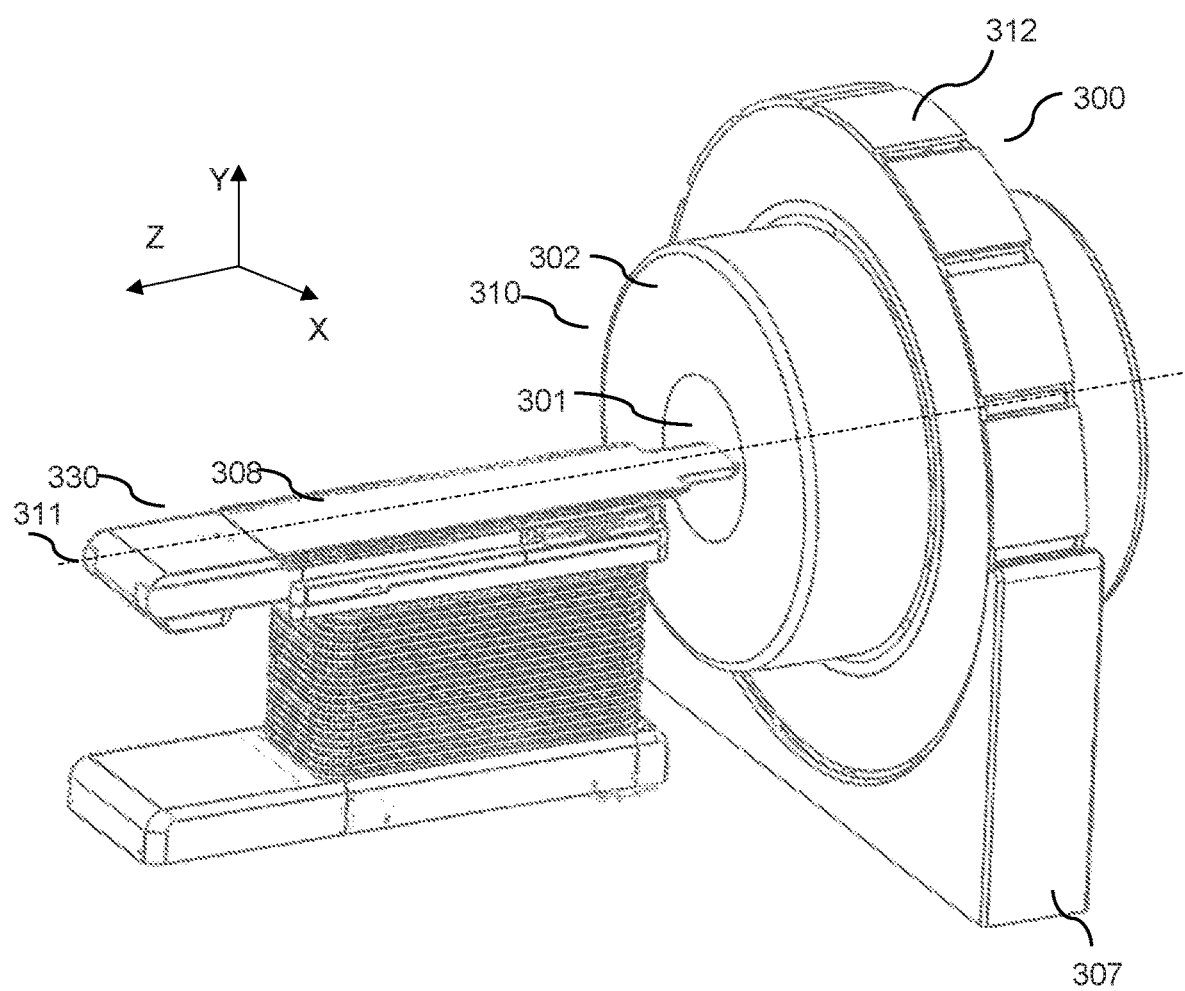
FIG. 3A illustrates an exemplary therapeutic apparatus according to some embodiments of the present disclosure.

FIG. 3A illustrates an exemplary therapeutic apparatus 110 according to some embodiments of the present disclosure. As illustrated in FIG. 3A, the therapeutic apparatus 110 may include an MRI apparatus 310, a radiation therapy apparatus 300, and a treatment table 330. In some embodiments, the MRI apparatus 310 may generate the MRI data as described in connection with operation 202, and the radiation therapy device 300 may apply the therapeutic radiation as described in connection with operation 210.

The MRI apparatus 310 may include a bore 301, a magnetic body 302, one or more gradient coils (not shown), and one or more radiofrequency (RF) coils (not shown). The MRI apparatus 310 may be configured to acquire image data from an imaging region. For example, the image data may relate to the treatment region associated with a tumor. In some embodiments, the MRI apparatus 310 may be a permanent magnet MRI scanner, a superconducting electromagnet MRI scanner, or a resistive electromagnet MRI scanner, etc., according to the types of the magnetic body 302. In some embodiments, the MRI apparatus 310 may be a high-field MRI scanner, a mid-field MRI scanner, and a low-field MRI scanner, etc., according to the intensity of the magnetic field. In some embodiments, the MRI apparatus 310 may be of a closed-bore (cylindrical) type, an open-bore type, or the like.

The magnetic body 302 may have the shape of an annulus and may generate a static magnetic field BO. The magnetic body 302 may be of various types including, for example, a permanent magnet, a superconducting electromagnet, a resistive electromagnet, etc. The superconducting electromagnet may include niobium, vanadium, technetium alloy, etc.

The one or more gradient coils may generate magnetic field gradients to the main magnetic field BO in the X, Y, and/or Z directions (or axes). In some embodiments, the one or more gradient coils may include an X-direction (or axis) coil, a Y-direction (or axis) coil, a Z-direction (or axis) coil, etc. For example, the Z-direction coil may be designed based on a circular (Maxwell) coil, the X-direction coil and the Y-direction coil may be designed on the basis of the saddle (Golay) coil configuration. As used herein, the X direction may also be referred to as the readout (RO) direction (or a frequency encoding direction), the Y direction may also be referred to as the phase encoding (PE) direction, the Z direction may also be referred to as the slice-selection encoding direction. In the present disclosure, the readout direction and the frequency encoding direction may be used interchangeably.

Merely by way of example, the gradient magnetic fields may include a slice-selection gradient field corresponding to the Z-direction, a phase encoding (PE) gradient field corresponding to the Y-direction, a readout (RO) gradient field corresponding to the X-direction, etc. The gradient magnetic fields in different directions may be used to encode the spatial information of MR signals. In some embodiments, the gradient magnetic fields may also be used to perform at least one function of flow encoding, flow compensation, flow dephasing, or the like, or any combination thereof.

The one or more RF coils may emit RF pulses to and/or receive MR signals from a subject (e.g., a body, a substance, an object) being examined. As used herein, an RF pulse may include an excitation RF pulse and a refocusing RF pulse. In some embodiments, the excitation RF pulse (e.g., a 90-degree RF pulse) may tip magnetization vector away from the direction of the main magnetic field BO. In some embodiments, the refocusing pulse (e.g., a 180-degree RF pulse) may rotate dispersing spin isochromatic about an axis in the transverse plane so that magnetization vector may rephase at a later time. In some embodiments, the RF coil may include an RF transmitting coil and an RF receiving coil. The RF transmitting coil may emit RF pulse signals that may excite the nucleus in the subject to resonate at the Larmor frequency. The RF receiving coil may receive MR signals emitted from the subject. In some embodiments, the RF transmitting coil and RF receiving coil may be integrated into one single coil, for example, a transmitting/receiving coil. The RF coil may be one of various types including, for example, a quotient difference (QD) orthogonal coil, a phase-array coil, etc. In some embodiments, different RF coils 240 may be used for the scanning of different parts of a body being examined, for example, a head coil, a knee joint coil, a cervical vertebra coil, a thoracic vertebra coil, a temporomandibular joint (TMJ) coil, etc. In some embodiments, according to its function and/or size, the RF coil may be classified as a volume coil and a local coil. For example, the volume coil may include a birdcage coil, a transverse electromagnetic coil, a surface coil, etc. As another example, the local coil may include a solenoid coil, a saddle coil, a flexible coil, etc.

The radiation therapy device 300 may include a drum 312 and a pedestal 307. The drum 312 may have the shape of an annulus. The drum 312 may be disposed around the magnetic body 302 and intersect the magnetic body 302 at a central region of the magnetic body 302 along the axis 311 of the bore 301. The drum 312 may accommodate and support a radiation source that is configured to emit a radiation beam towards the treatment region in the bore 301. The radiation beam may be an X-ray beam, an electron beam, a gamma ray source, a proton ray source, etc. The drum 312, together with the radiation source mounted thereon, may be able to rotate around the axis 311 of the bore 301 and/or a point called the isocenter. Merely by way of example, the drum 312, together with the radiation source mounted thereon, may be able to rotate any angle, e.g., 90 degrees, 180 degrees, 360 degrees, 450 degrees, 540 degrees, around the axis 311. The drum 306 may be further supported by the pedestal 307.

It should be noted that the above description is merely provided for the purposes of illustration, and not intended to limit the scope of the present disclosure. For persons having ordinary skills in the art, multiple variations or modification may be made under the teaching of the present disclosure. For example, the radiation therapy device 300 may further include a linear accelerator configured to accelerate electrons, ions, or protons, a dose detecting device, a temperature controlling device (e.g., a cooling device), a multiple layer collimator, or the like, or any combination thereof. However, those variations and modifications do not depart from the scope of the present disclosure.

The treatment table 330 may include a platform 308 and a base frame 309. In some embodiments, the platform 308 may move along the horizontal direction and enter into the bore 301 of the MRI apparatus 310. In some embodiments, the platform 308 may move two-dimensionally, three-dimensionally, four-dimensionally, five-dimensionally or six-dimensionally. In some embodiments, the platform 308 may move according to the variance (e.g., position change) of the tumor estimated by, for example, a real-time MRI image obtained during a treatment.

In some embodiments, the subject may be placed on the platform 308 and sent into the MRI device. In some embodiments, the subject may be a human patient. The human patient may lie on the back, lie in prone, lie on the side on the platform 308.

During the treatment, the drum 312 may be set to rotate around the magnetic body 302. In some embodiments, the magnetic body 302 may include a recess (not shown) at its outer wall. The recess may be disposed around the entire circumference of the magnetic body 302. For example, the recess may have the shape of an annulus surrounding the magnetic body 302, thus accommodating at least part of the drum 312. In some embodiments, the recess may be disposed around part of the circumference of the magnetic body 302. For example, the recess may have the shape of one or more arcs around the magnetic body 302.

In some embodiments, the radiation source may move along an entire path of rotation within the recess. The radiation source may generate the radiation beam according to one or more parameters. Exemplary parameter may include a parameter of the radiation beam, a parameter of the radiation source, or a parameter of the platform 308. For example, the parameter of the radiation beam may include an irradiating intensity, an irradiating angle, an irradiating distance, an irradiating area, an irradiating time, an intensity distribution, or the like, or any combination thereof. The parameter of the radiation source may include a position, a rotating angle, a rotating speed, a rotating direction, the configuration of the radiation source, or the like, or any combination thereof. In some embodiments, the generation of the radiation beam by the radiation source may take into consideration energy loss of the radiation beam due to, e.g., the magnetic body 302 located in the pathway of the radiation beam that may absorb at least a portion of the radiation beam. For example, the irradiating intensity of the radiation beam may be set larger than that in the situation in which there is no energy loss due to, e.g., the absorption by the magnetic body 302 accordingly to compensate the energy loss such that the radiation beam of a specific intensity may impinge on a treatment region (e.g., a tumor).

Figure 3B:
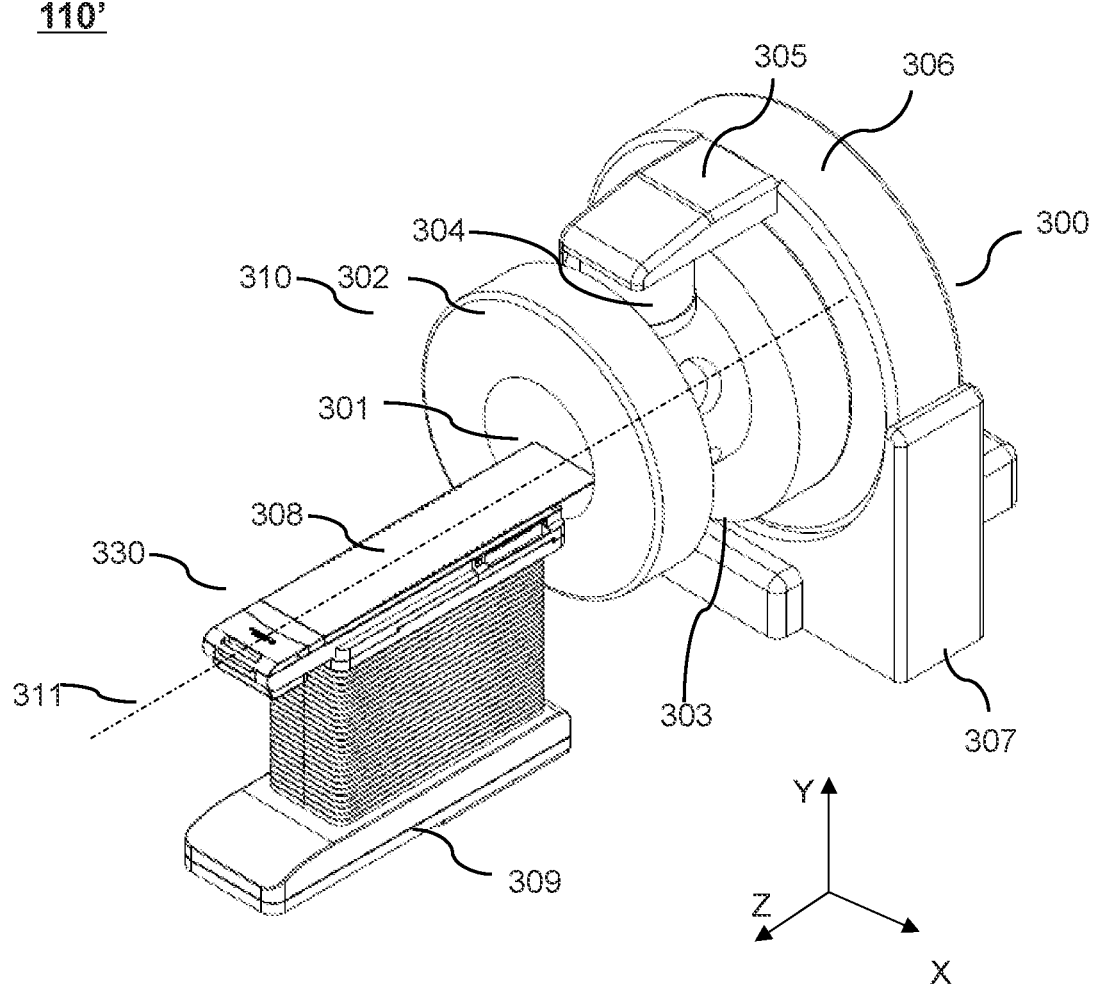
FIG. 3B illustrates another exemplary therapeutic apparatus according to some embodiments of the present disclosure.

FIG. 3B illustrates another exemplary therapeutic apparatus 110' according to some embodiments of the present disclosure. Compared with the therapeutic apparatus 110 described in FIG. 3A, the therapeutic apparatus 110' may use a gantry 306 instead of the drum 312. The gantry 306 may be disposed at one side of the magnetic body 302. A treatment head 304 may be installed on the gantry 306 via a treatment arm 305. The treatment head 304 may accommodate the radiation source. The gantry 306 may be able to rotate the treatment head 304 around the axis 311 of the bore 301.

As shown in FIG. 3B, a recess 303 may be formed at the outer wall of the magnetic body 302 and have the shape of an annulus. The recess 303 may accommodate at least a portion of the treatment head 304 and provide a path for rotation of the treatment head 304. This arrangement may reduce the distance between the treatment head 304 and the axis 311 of the bore 301 along the radial direction of the magnetic body 302. In some embodiments, the reduction of the distance between the treatment head 304 and the axis 311 of the bore 301 may cause an increase of the radiation dose that may reach the treatment region (e.g., a tumor) which leads to an enhancement in the therapeutic efficiency. In some embodiments, the width of the recess 303 along the Z direction (i.e., the axial direction of the magnetic body 302) may be no less than the width of the treatment head 304 along the Z direction.

It should be noted that the above description of the therapeutic apparatus 110 is merely provided for the purposes of illustration, and not intended to limit the scope of the present disclosure. For persons having ordinary skills in the art, multiple variations and modifications may be made under the teachings of the present disclosure. For example, the assembly and/or function of the therapeutic apparatus 110 may vary or change according to a specific implementation scenario. In some embodiments, the magnetic body 302 of the MRI apparatus 310 may also rotate relative to the treatment head 304. For example, the radiation therapy device 300 and the MRI apparatus 310 may synchronously or asynchronously rotate around a same axis (e.g., the axis 311). However, those variations and modifications do not depart from the scope of the present disclosure.

Figure 4A:
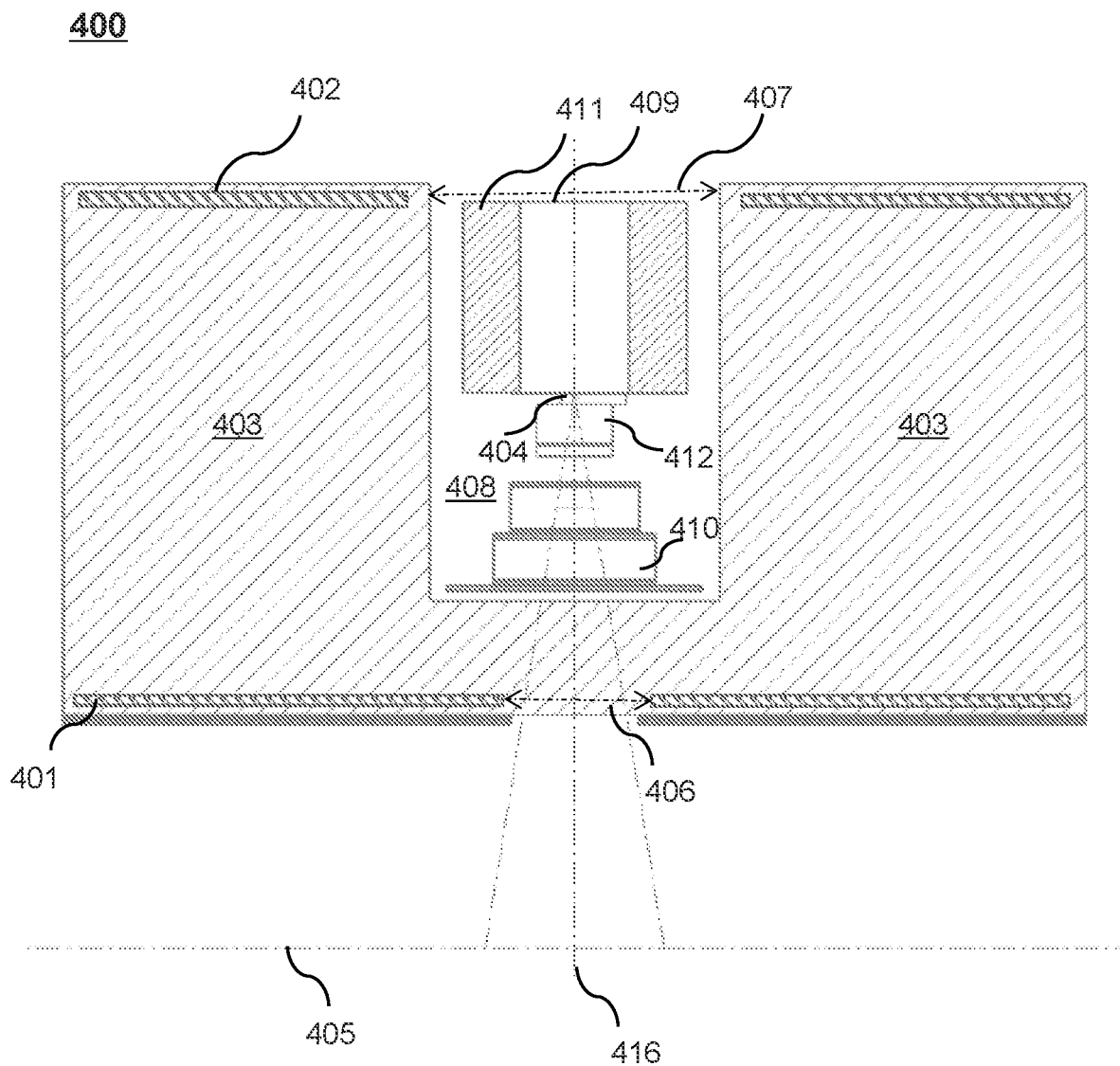
FIG. 4A shows an upper portion of a cross-sectional view of an exemplary therapeutic apparatus viewed along the X direction according to some embodiments of the present disclosure.

FIG. 4A shows an upper portion of a cross-sectional view of an exemplary therapeutic apparatus 400 viewed along the X direction according to some embodiments of the present disclosure. The therapeutic apparatus 400 may include an MRI apparatus that is configured to generate MRI data and a radiation therapy apparatus that is configured to apply therapeutic radiation.

As shown in FIG. 4A, the MRI apparatus may include a plurality of main magnetic coils 401, a plurality of shielding magnetic coils 402, and a cryostat 403.

The plurality of main magnetic coils 401 and the plurality of shielding magnetic coils 402 may be accommodated in the cryostat 403 and maintained in the superconductive state under a certain condition (e.g., when both the coils are merged in a cooling medium in the cryostat 403).

The cryostat 403 may have the shape of an annulus with an axis 405 (e.g., the axis 311 in FIG. 3A). The plurality of main magnetic coils 401 may be arranged coaxially along the axis 405 to generate a uniform magnetic field (e.g., a static magnetic field B0) within a specific region (e.g., the region within the bore 301) when the plurality of main magnetic coils 401 carry an electric current along a first direction.

The plurality of shielding magnetic coils 402 may also be arranged coaxially along the axis 405 at a larger radius from the axis 405 than the plurality of main magnetic coils 401. The plurality of shielding magnetic coils 402 may carry an electric current along a second direction that is opposed to the first direction. The plurality of shielding magnetic coils 402 may help shield the magnetic field generated by the plurality of main magnetic coils 401 on a region outside the MRI apparatus.

As shown in FIG. 4A, the cryostat 403 may include two chambers (e.g., the left chamber and the right chamber for brevity). The two chambers may be located at opposite sides of the cryostat 403 along the axial direction (i.e., the direction of the axis 405) and may be connected by a neck portion between the two chambers. The neck portion may have a smaller radial size than the two chambers. Each chamber may have the shape of an annulus with a different outer wall. In some embodiments, the outer wall may refer to the outermost surface of each chamber that has the shape of a ring. The two chambers and the neck portion may share a same inner wall, i.e., the inner wall of the cryostat 403. In some embodiments, the inner wall may refer to the innermost surface of each chamber that also has the shape of a ring. In some embodiments, each chamber may accommodate at least one of the plurality of main magnetic coils 401 and at least one of the plurality of shielding magnetic coils 402. For example, at least one of the plurality of main magnetic coils 401 may be arranged near the inner wall of the left chamber, and at least one of the plurality of shielding magnetic coils 402 may be arranged near the outer wall of the left chamber. A gap 406 may be formed between the main magnetic coils arranged in the left chamber and the main magnetic coils arranged in the right chamber, allowing the radiation beam produced by the radiation therapy apparatus to pass through. The two chambers may be in fluid communication with each other through the neck portion between them. The cryostat 403 may contain cooling mediums in which the plurality of main magnetic coils 401 and the plurality of shielding magnetic coils 402 are merged to achieve the superconducting state.

The cryostat 403 may have a recess 408 at a radial position between the inner wall of the cryostat 403 and the outer walls of the different chambers of the cryostat 403. The recess 408 may have an opening 407 formed between the outer walls of the two chambers of the cryostat 403. The recess 408 may have the shape of an annulus when viewed in a perspective view. The annulus may have same or different widths (i.e., the size in the axial direction) at different radial positions. The recess 408 may have a depth (i.e., the thickness of the annulus in the radial direction) which is defined as the distance from the opening 407 to the outermost surface of the neck portion of the cryostat 403 in the radial direction.

The recess 408 may be configured to accommodate the components of the radiation therapy apparatus. As shown in FIG. 4A, the recess 408 may accommodate a radiation source that includes a linear accelerator 409, a shielding structure 411, a collimator 412, a target 404 and a multi-leaf collimator (MLC) 410.

The linear accelerator 409 may be configured to accelerate charged subatomic particles or ions to a high speed. In some embodiments, the linear accelerator 409 may accelerate electrons using microwave technology. For example, the linear accelerator 409 may accelerate electrons in an electron beam with energy group between 4 MeV to 22 MeV using high RF electromagnetic waves.

The linear accelerator 409 may be mounted to a gantry or a drum (e.g., the gantry 306 or the drum 312) that is capable of rotating around the axis 405 and may enable the radiation beam to be emitted from an arbitrary circumferential position. As shown in FIG. 4A, the gantry or the drum may rotate to a first position where the linear accelerator 409 may be located above the axis 405. The linear accelerator 409 may include an accelerating waveguide (tube) whose axis is perpendicular to the axis 405. The accelerating waveguide (tube) may provide a linear path for accelerating the electrons along a beam path that is perpendicular to the axis 405.

The accelerating waveguide (tube) of the linear accelerator 409 may be at least partially surrounded by the shielding structure 411. In some embodiments, the shielding structure 411 may provide a cavity coaxial with the longitudinal axis of the tube of the linear accelerator 409, with at least one end being open to let through the radiation beam emitted from the linear accelerator 409. In some embodiments, the shielding structure 411 may have any configuration. For example, the shielding structure 411 may include one annulus on the left side of the recess (i.e., the side near the left chamber) and one annulus on the right side of the recess (i.e., the side near the right chamber) with plates connecting the two annulus. Alternatively, the annulus may be replaced by separate arc segments. It should be noted that the shielding structure 411 may be of any shapes provided that at least one end of the shielding structure 411 is open for the radiation beam emitted from the linear accelerator 409 to pass. Details regarding the exemplary configurations of the shielding structure 411 may be found elsewhere in the disclosure (e.g., FIGS. 8A-16B and the descriptions thereof).

In some embodiments, the shielding structure 411 may include a plurality of shielding layers. At least one of the plurality of shielding layers may be used to reduce the magnetic interference between one or more components of the MRI apparatus and the radiation therapy apparatus. For example, the shielding structure 411 may include a magnetic shielding layer configured to shield the magnetic field produced by the MRI apparatus (e.g., the main magnetic coils, the shielding magnetic coils, the gradient coils) in case that the electrons may be influenced by the magnetic field.

Additionally, at least one of the plurality of shielding layers may be used to reduce the RF and/or microwave interference between one or more components of the MRI apparatus and the radiation therapy apparatus. For example, the shielding structure 411 may include an electromagnetic shielding layer configured to shield the RF signals produced by the MRI apparatus (e.g., the RF coils) and the microwave produced by the radiation therapy apparatus.

The plurality of shielding layers may be made of same material and/or different materials. For example, both the electromagnetic shielding layer and the magnetic shielding layer may be made of high magnetic susceptibility and permeability material (e.g., non-oriented silicon steel), or one of the electromagnetic shielding layer and the magnetic shielding layer is made of high electric conductivity and magnetic permeability material. In some embodiments, the plurality of shielding layers may be magnetically and/or electrically isolated from each other with a suitable dielectric material, such as air or plastic, between them.

Additionally or alternatively, at least one of the plurality of shielding layers may be used to protect one or more components of the MRI apparatus from the radiation produced by the linear accelerator 409. For example, one shielding layer of the plurality of shielding layers may be made of a material that is able to absorb the radiation produced by the radiation beam of the linear accelerator 409. Exemplary material that is able to absorb the radiation may include materials for absorbing photon ray and/or materials for absorbing neutron ray. The materials for absorbing photon ray may include steel, aluminum, lead, tungsten, etc. The materials for absorbing neutron ray may include boron, graphite, etc. It should be noted that, in some embodiments, the shielding structure 411 may be made only with radiation absorbing material, without high magnetic susceptibility and permeability material. In this way, the shielding structure 411 may only provide radiation shielding for one or more components of the MRI apparatus.

The target 404 may be configured to receive the accelerated charged subatomic particles or ions (e.g., an electron beam) to produce the radiation beam for the therapeutic radiation. For example, the electron beam may collide with the target 404 to generate high-energy X-rays according to the bremsstrahlung effect. In some embodiments, the target 404 may be located near the exit window of the linear accelerator 409 to receive the accelerated electron beam. In some embodiments, the target 404 may be made of materials including aluminium, copper, silver, tungsten, or the like, or any combination thereof. Alternatively, the target 404 may be made of composite materials including tungsten and copper, tungsten and silver, tungsten and aluminium, or the like, or any combination thereof.

The radiation beam from the target 404 may pass through the collimator 412 to form a beam with a specific shape (e.g., cone beam). In some embodiments, the collimator 412 may include a primary collimator, a flattening filter and at least one secondary collimator.

Figure 6A:
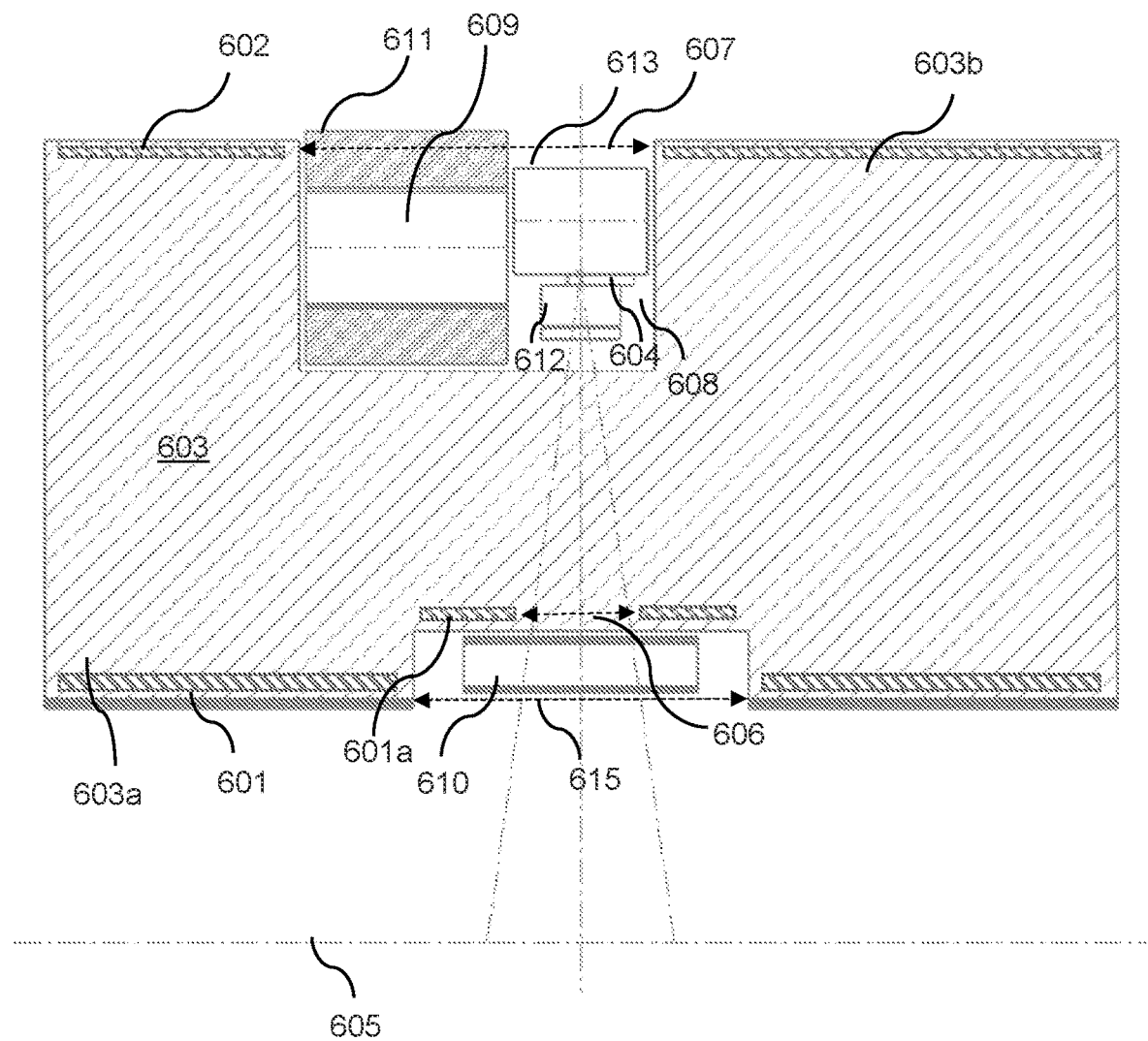
FIG. 6A shows an upper portion of a cross-sectional view of an exemplary therapeutic apparatus viewed along the X direction according to some embodiments of the present disclosure.

The MLC 410 may be configured to reshape the radiation beam. For example, the MLC 410 may adjust the irradiating shape, the irradiating area, etc., of the radiation beam. The MLC 410 may be placed anywhere on the path of the radiation beam. For example, the MLC 410 may be placed close to the linear accelerator 409 as shown in FIG. 4A. Thus, the radiation beam, after being reshaped by the MLC 410, may further pass through the neck portion of the cryostat 403 and the gap 406 between the plurality of main magnetic coils to arrive at the treatment region. As another example, the MLC 410 may be placed at a relatively long distance away from the linear accelerator (e.g., as shown in FIG. 6A) such that the MLC 410 may be closer to, e.g., the patient to be radiated.

The MLC 410 may stay fixed relative to the linear accelerator 409, thus rotating together with the linear accelerator 409 around the axis 405. The MLC 410 may include a plurality of individual leaves of high atomic numbered materials (e.g., tungsten) moving independently in and out of the path of the radiation beam in order to block it. The shape of the radiation beam may vary when the plurality of individual leaves move in and out, forming different slots that simulates the cross section of the tumor viewed from an axis of the radiation beam (i.e., the vertical dotted line 416 shown in FIG. 4A). In some embodiments, the MLC 410 may include one or more layers of leaves. For example, the MLC 410 may have only one layer of leaves and the height of the MLC 410 along the axis of the radiation beam may be between 7 and 10 centimeters. For another example, the MLC 410 may include two layers and the height of the MLC 410 may be at least 15 centimeters.

Figure 4B:
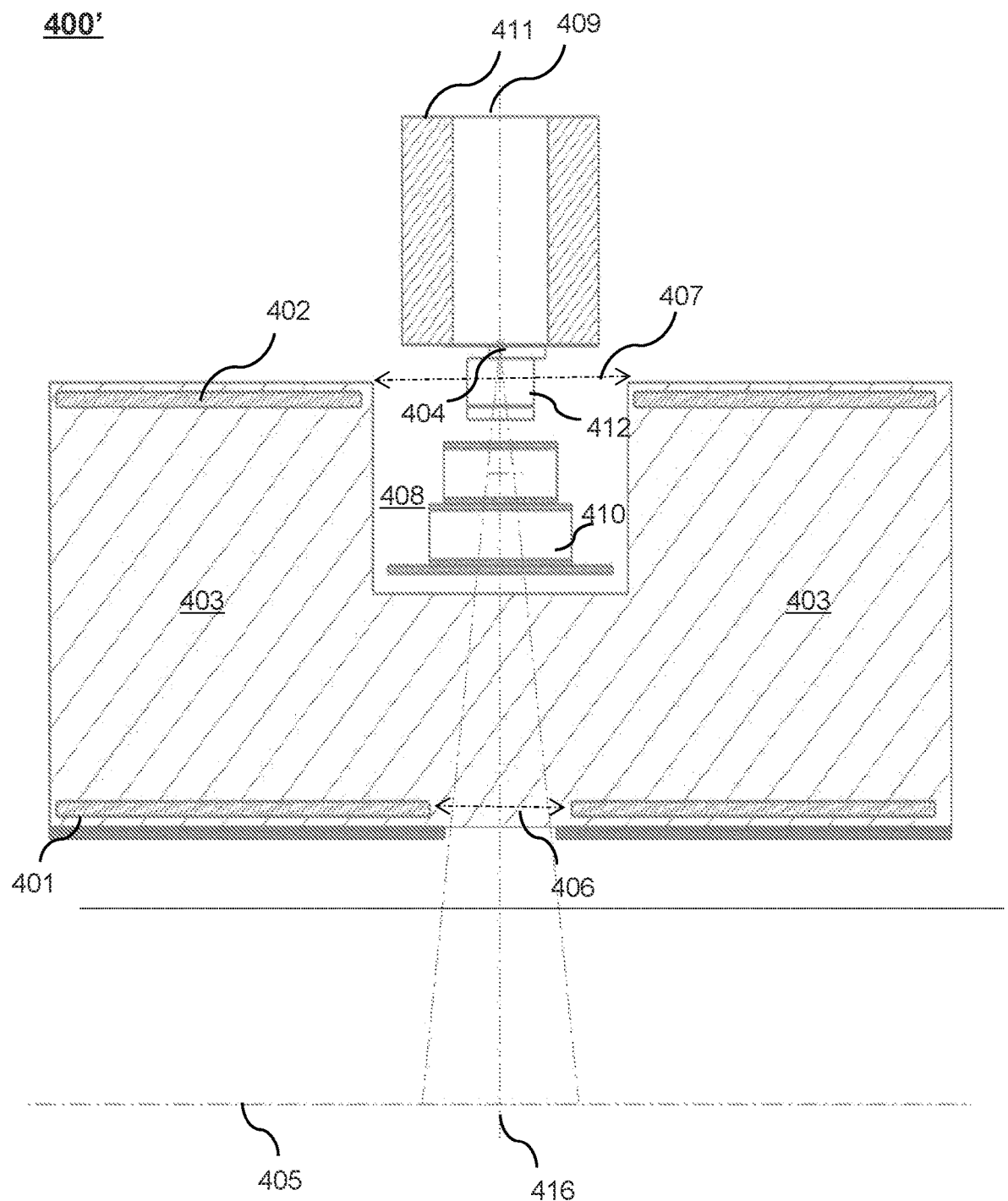
FIG. 4B shows an upper portion of a cross-sectional view of another exemplary therapeutic apparatus viewed along the X direction according to some embodiments of the present disclosure.

FIG. 4B shows an upper portion of a cross-sectional view of an exemplary therapeutic apparatus 400' viewed along the X direction according to some embodiments of the present disclosure. Compared with the therapeutic apparatus 400 described in FIG. 4A, at least part of the linear accelerator 409 of the therapeutic apparatus 400' may be located at the outside of the recess 408 along the radial direction of the cryostat 403. As shown in FIG. 4B, the linear accelerator 409 and the shielding structure 411 surrounding it along the axis of the radiation beam may stretch out of the opening 407 formed by the outer walls of the cryostat 403. In some embodiments, the linear accelerator 409 and the shielding structure 411 may be supported by or mounted to a gantry or a drum (e.g., the gantry 306 or the drum 312) that is capable of rotating around the axis 405.

Figure 4C:
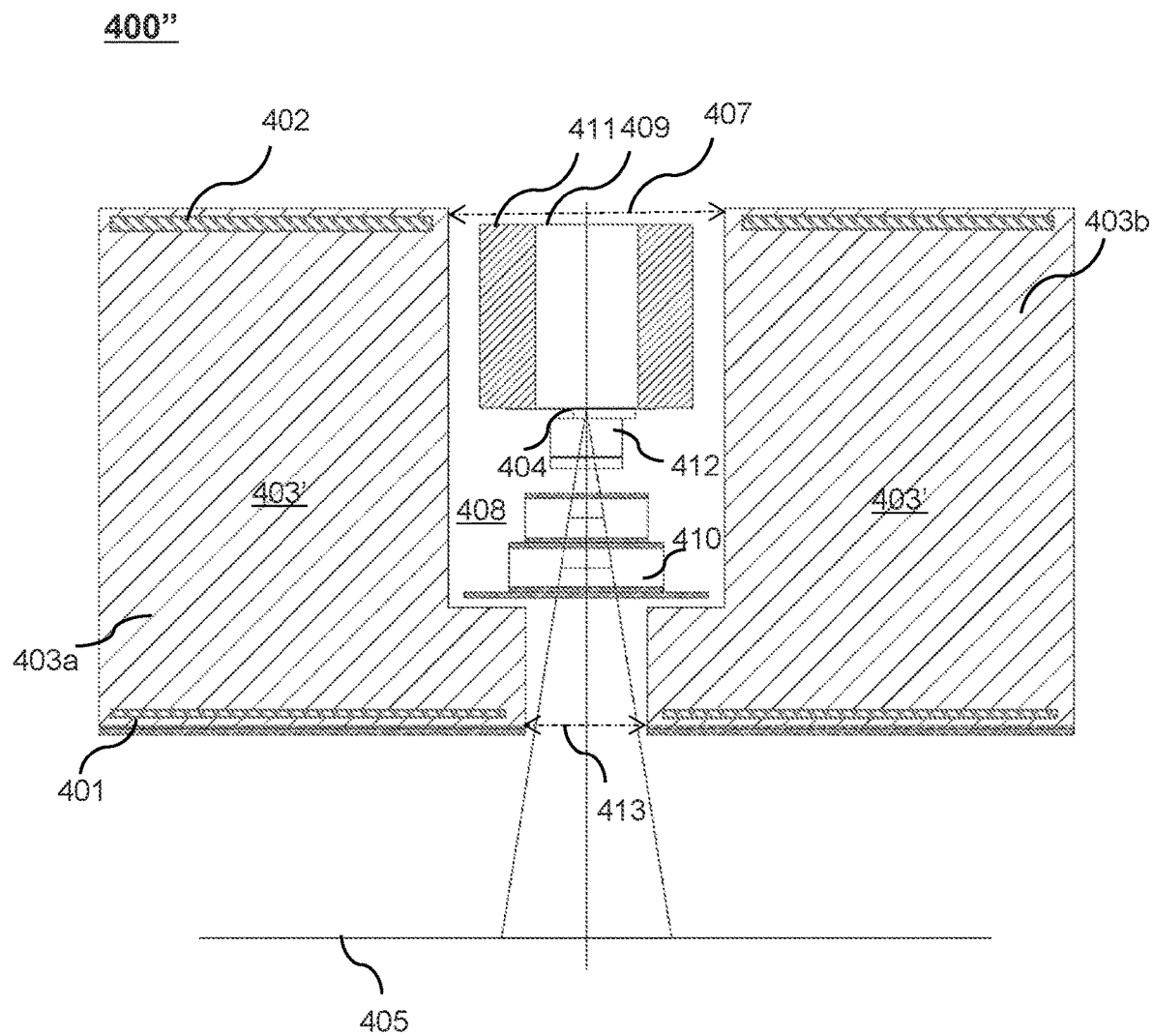
FIG. 4C shows an upper portion of a cross-sectional view of another exemplary therapeutic apparatus viewed along the X direction according to some embodiments of the present disclosure.

FIG. 4C shows an upper portion of a cross-sectional view of an exemplary therapeutic apparatus 400" viewed along the X direction according to some embodiments of the present disclosure. Compared with the therapeutic apparatus 400 described in FIG. 4A, the cryostat 403' of therapeutic apparatus 400" may have two isolated chambers. As shown in FIG. 4C, the left chamber 403a and the right chamber 403b may be isolated from each other and thus no fluid communication is established between them. The cryostat 403' may have two different inner walls for the left chamber 403a and the right chamber 403b. Another opening 413 of the recess 408 may be formed between the two different inner walls. The radiation beam, after being reshaped by the MLC 410, may pass through the opening 413 and arrive at the treatment region.

Figure 4D:
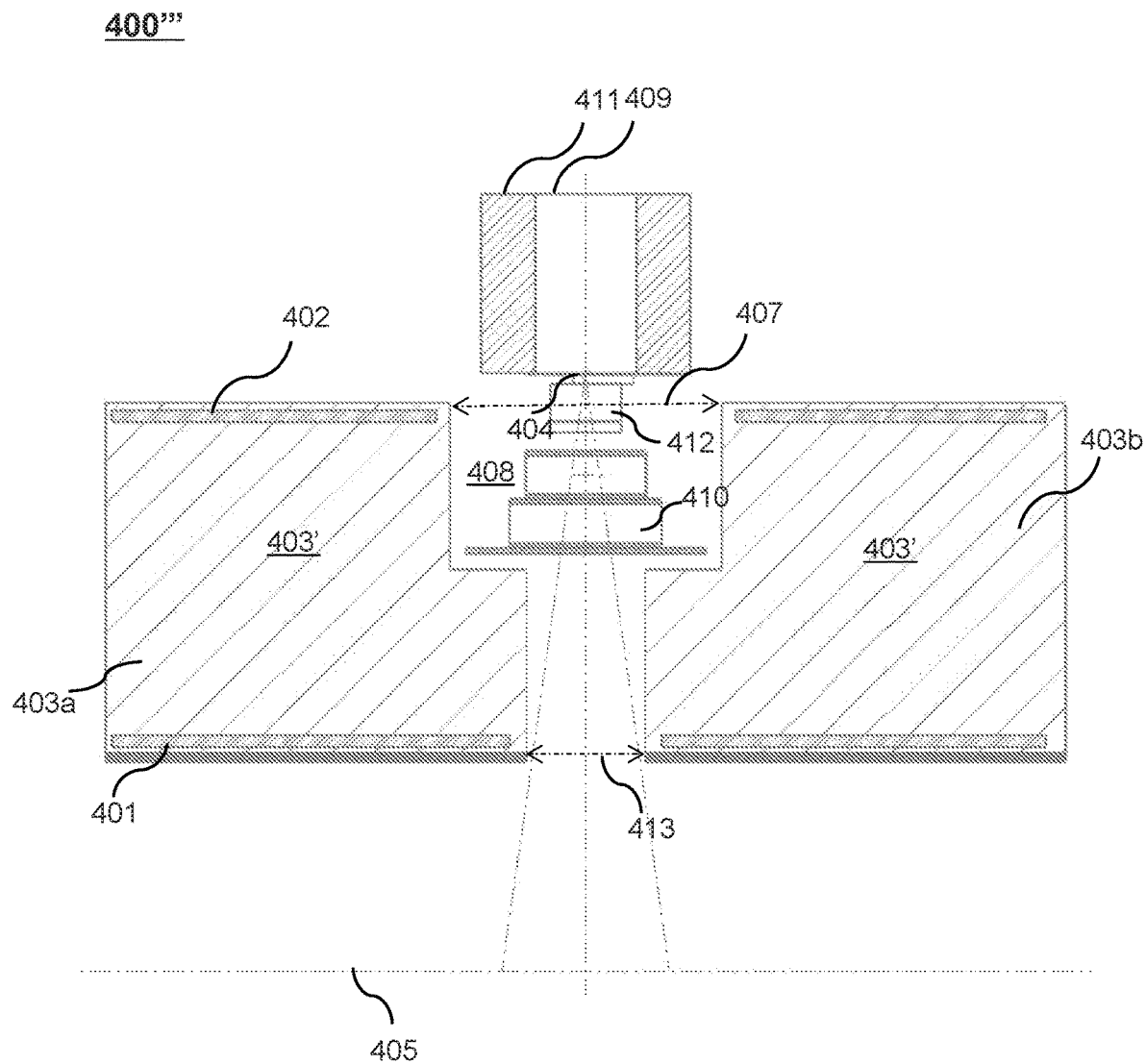
FIG. 4D shows an upper portion of a cross-sectional view of another exemplary therapeutic apparatus viewed along the X direction according to some embodiments of the present disclosure.

FIG. 4D shows an upper portion of a cross-sectional view of another exemplary therapeutic apparatus 400''' viewed along the X direction according to some embodiments of the present disclosure. Compared with the therapeutic apparatus 400" described in FIG. 4C, at least part of the linear accelerator 409 of the therapeutic apparatus 400''' may be located at the outside of the recess 408 along the radial direction of the cryostat 403'. As shown in FIG. 4D, the linear accelerator 409 and the shielding structure 411 surrounding it along the axis of the radiation beam may stretch out of the opening 407 formed by the outer walls of the cryostat 403'. In some embodiments, the linear accelerator 409 and the shielding structure 411 may be supported by or mounted to a gantry or a drum (e.g., the gantry 306 or the drum 312) that is capable of rotating around the axis 405.

It should be noted that the above description of the therapeutic apparatus 400, 400', 400", or 400''' is merely provided for the purposes of illustration, and not intended to limit the scope of the present disclosure. For persons having ordinary skills in the art, multiple variations and modifications may be made under the teachings of the present disclosure. For example, the collimator 412 and the MLC 410 may be integrated to form a single collimator. For another example, the neck portion illustrated in the cryostat 403 may not form an entire annulus. Specifically, the neck portion may be discrete arcs that connect the left chamber and the right chamber of the cryostat 403. Therefore, the neck portion may intermittently appear in the path of the radiation beam when the linear accelerator 409 rotates around the axis 405 to generate the radiation beam.

Figure 5A:
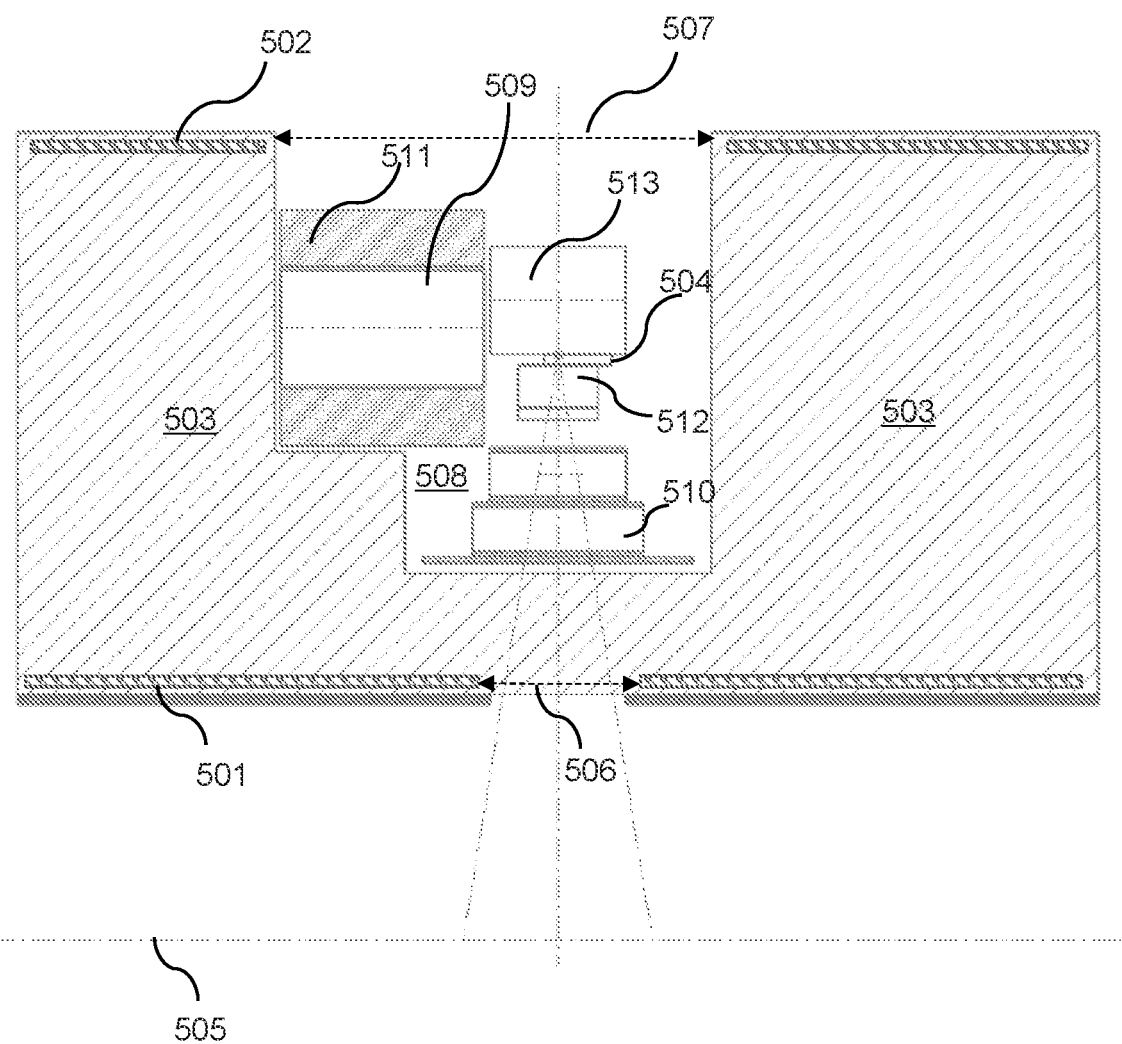
FIG. 5A shows an upper portion of a cross-sectional view of an exemplary therapeutic apparatus viewed along the X direction according to some embodiments of the present disclosure.

FIG. 5A shows an upper portion of a cross-sectional view of an exemplary therapeutic apparatus 500 viewed along the X direction according to some embodiments of the present disclosure. As shown in FIG. 5A, the therapeutic apparatus 500 may include a plurality of main magnetic coils 501, a plurality of shielding magnetic coils 502, a cryostat 503 with an axis, a target 504, a gap 506, an opening 507, a recess 508, a linear accelerator 509, an MLC 510, a shielding structure 511, a collimator 512, and a deflection unit 513. The plurality of main magnetic coils 501, the plurality of shielding magnetic coils 502, the cryostat 503, the target 504, the axis 505, the gap 506, the opening 507, the recess 508, the MLC 510, and the collimator 512 may be similar to the plurality of main magnetic coils 401, the plurality of shielding magnetic coils 402, and the cryostat 403, the target 404, the axis 405, the gap 406, the opening 407, the recess 408, the MLC 410, and the collimator 412, and the descriptions thereof are not repeated here.

Unlike the linear accelerator 409, the axis of the accelerating waveguide (tube) of the linear accelerator 509 may be parallel to the axis 505. Therefore, the accelerating waveguide (tube) may provide a linear path for accelerating the electrons along a beam path that is parallel to the axis 505 (also referred to as "parallel beam pass"). The plurality of main magnetic coils 501 and the plurality of shielding magnetic coils 502 may generate a magnetic field that is parallel or substantially parallel to the axis 505 (also referred to as "parallel magnetic field"). It shall be appreciated that the parallel magnetic field may pose least influence to the parallel beam pass. Therefore, the linear accelerator 509 may help reduce the influence of the magnetic field generated by the MRI apparatus on the electrons. Similarly, the accelerating waveguide (tube) of the linear accelerator 509 may be at least partially surrounded by the shielding structure 511. The shielding structure 511 may be continuously distributed along the direction of the axis 505. In some embodiments, the shielding structure 511 may stretch to cover two ends of the linear accelerator along the direction of the axis, meaning that the shielding structure 511 may have a larger size than the linear accelerator 509 along the direction of the axis. The shielding structure 511 may be configured to further reduce the interference from the magnetic field generated by the MRI apparatus.

The deflection unit 513 may be configured to deflect the accelerated electrons from the parallel beam path onto the target 504. In some embodiments, the deflected electrons may perpendicularly impinge on the target 504, and therefore the deflection angle of the electrons may be 90 or 270 degrees. In some embodiments, the deflection unit 513 may include one or more magnets configured to provide a deflection magnetic field to deflect the accelerated electrons.

As shown in FIG. 5A, both of the linear accelerator 509 and the deflection unit 513 are disposed within the recess 508 between the opening 507 and the gap 506. In some embodiments, no shielding magnetic coil is arranged to "cover" the linear accelerator 509 and/or the deflection unit 513 along the radial direction of the cryostat 503. That is, there is no overlap between the axial positions of the plurality of shielding magnetic coils 502 and that of the linear accelerator 509 and/or the deflection unit 513. Further, the cryostat 503 may have a continuous body (i.e., a body which provides continuous fluid communication) along the radial direction of the cryostat 503, which accommodates both of the plurality of main magnetic coils 501 and the plurality of shielding magnetic coils 502.

Figure 5B:
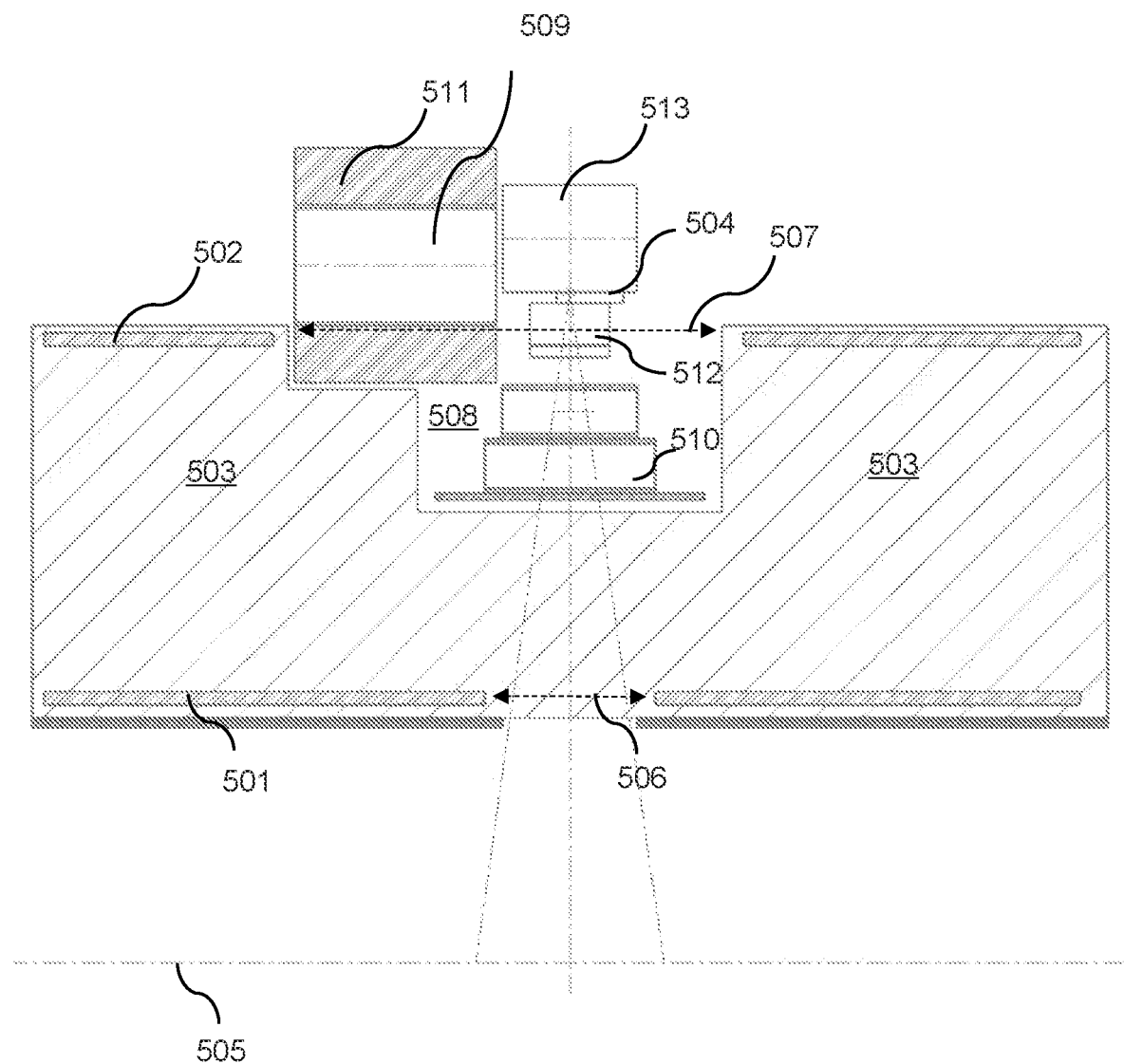
FIG. 5B shows an upper portion of a cross-sectional view of another exemplary therapeutic apparatus viewed along the X direction according to some embodiments of the present disclosure.

FIG. 5B shows an upper portion of a cross-sectional view of an exemplary therapeutic apparatus 500' viewed along the X direction according to some embodiments of the present disclosure. Compared with the therapeutic apparatus 500 described in FIG. 5A, at least part of the linear accelerator 509 of the therapeutic apparatus 500' may be located at the outside of the recess 508 along the radial direction of the cryostat 503. As shown in FIG. 5B, the linear accelerator 509, the shielding structure 511 and the deflection unit 513 may at least partially stretch out of the opening 507 formed by the outer walls of the cryostat 503. In some embodiments, the linear accelerator 509 and the shielding structure 511 may be supported by or mounted to a gantry or a drum (e.g., the gantry 306 or the drum 312) that is capable of rotating around the axis 505.

Figure 5C:
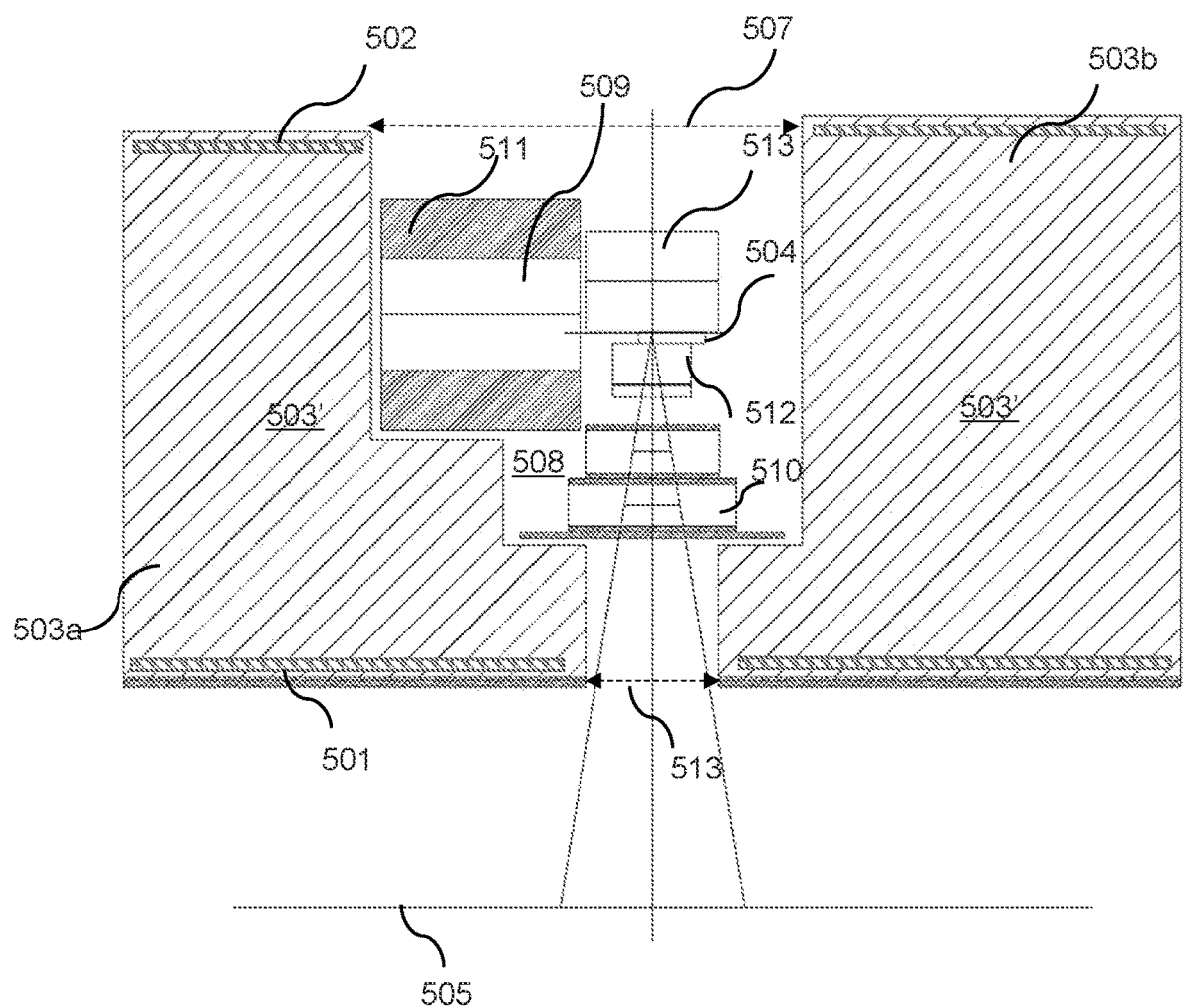
FIG. 5C shows an upper portion of a cross-sectional view of another exemplary therapeutic apparatus viewed along the X direction according to some embodiments of the present disclosure.

FIG. 5C shows an upper portion of a cross-sectional view of another exemplary therapeutic apparatus 500" viewed along the X direction according to some embodiments of the present disclosure. Compared with the therapeutic apparatus 500 described in FIG. 5A, the cryostat 503' of therapeutic apparatus 500" may have two isolated chambers. As shown in FIG. 5C, the left chamber 503a and the right chamber 503b may be isolated from each other and thus no fluid communication is established between them. The cryostat 503' may have two different inner walls for the left chamber 503a and the right chamber 503b. Another opening 513 of the recess 508 may be formed between the two different inner walls. The radiation beam, after being reshaped by the MLC 510, may pass through the opening 513 and arrive at the treatment region.

Figure 5D:
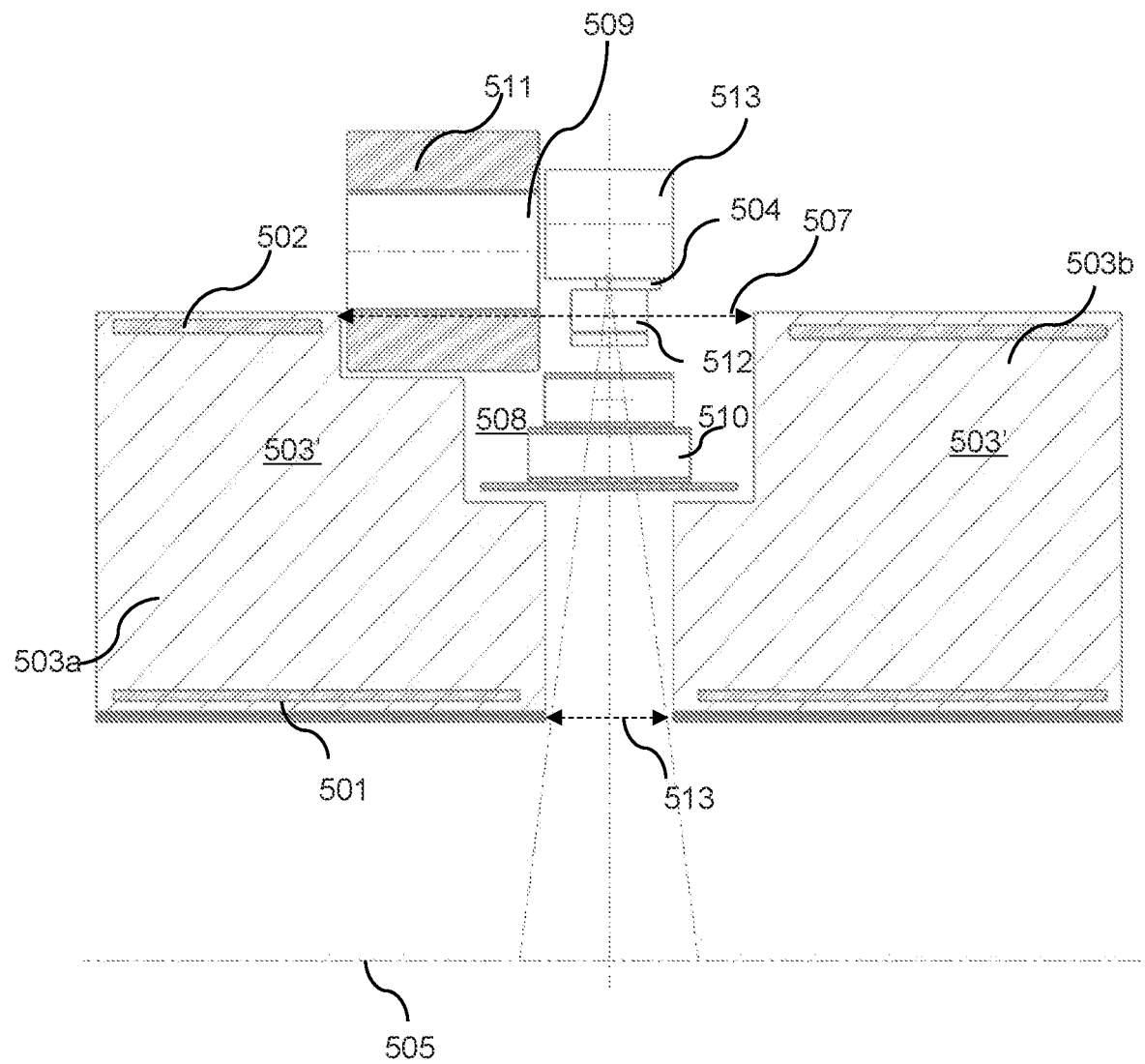
FIG. 5D shows an upper portion of a cross-sectional view of another exemplary therapeutic apparatus viewed along the X direction according to some embodiments of the present disclosure.

FIG. 5D shows an upper portion of a cross-sectional view of an exemplary therapeutic apparatus 500'" viewed along the X direction according to some embodiments of the present disclosure. Compared with the therapeutic apparatus 500" described in FIG. 5C, at least part of the linear accelerator 509 of the therapeutic apparatus 500'" may be located at the outside of the recess 508 along the radial direction of the cryostat 503'. As shown in FIG. 5D, the linear accelerator 509, the shielding structure 511 and the deflection unit 513 may at least partially stretch out of the opening 507 formed by the outer walls of the cryostat 503'. In some embodiments, the linear accelerator 509, the shielding structure 511, and the deflection unit 513 may be supported by or mounted to a gantry or a drum (e.g., the gantry 306 or the drum 312) that is capable of rotating around the axis 505.

It should be noted that the above description of the therapeutic apparatus 500, 500', 500", or 500'" is merely provided for the purposes of illustration, and not intended to limit the scope of the present disclosure. For persons having ordinary skills in the art, multiple variations and modifications may be made under the teachings of the present disclosure. For example, the collimator 512 and the MLC 510 may be integrated to form a single collimator. For another example, the neck portion illustrated in the cryostat 503 may not form an entire annulus. Specifically, the neck portion may be discrete arcs that connect the left chamber and the right chamber of the cryostat 503. Therefore, the neck portion may intermittently appear in the path of the radiation beam when the linear accelerator 509 rotates around the axis 505 to generate the radiation beam.

FIG. 6A shows an upper portion of a cross-sectional view of an exemplary therapeutic apparatus 600 viewed along the X direction according to some embodiments of the present disclosure. As shown in FIG. 6A, the therapeutic apparatus 600 may include a plurality of main magnetic coils 601, a plurality of shielding magnetic coils 602, a cryostat 603 with an axis 605, a target 604, a first opening 607, a second opening 615, a recess 608, a linear accelerator 609, an MLC 610, a shielding structure 611, a collimator 612, and a deflection unit 613. The plurality of main magnetic coils 601, the plurality of shielding magnetic coils 602, the target 604, the axis 605, the first opening 607, the recess 608, the linear accelerator 609, the collimator 612, and the deflection unit 613 may be similar to the plurality of main magnetic coils 501, the plurality of shielding magnetic coils 502, the target 504, the axis 505, the opening 507, the recess 508, the linear accelerator 509, the collimator 512, and the deflection unit 513 and the descriptions are not repeated here.

Compared with the MLC 510 shown in FIG. 5A, the MLC 610 may be located apart from the linear accelerator 609 along the radial direction such that the MLC 610 may be closer to, for example, the treatment region to be radiated. It shall be noted that the closer the distance between the MLC and the treatment region, the more accurate the shape of the radiation beam that irradiates on the treatment region may be controlled by the MLC.

The cryostat 603 may have a concave structure at the inner walls of the cryostat 603 to accommodate the MLC 610. Similar to the recess 608 that has the first opening 607 formed between the outer walls of the two chambers of the cryostat 603, the concave structure may have a second opening 615 formed between the inner walls of the two chambers of the cryostat 603. The concave structure may have the shape of an annulus and may be coaxial with the recess 608. The concave structure and the recess 608 may be separated by the neck portion of the cryostat 603. That is, the outermost surface of the neck portion forms the innermost boundary of the recess 608, and the innermost surface of the neck portion forms the outermost boundary of the concave structure. The concave structure may have a depth along the radial direction of the cryostat 603 that is larger than the height of the MLC 610 along the axis of the radiation beam. In some embodiment, one or more of the plurality of main magnetic coils 601 (e.g., 601a) may be arranged to surround the concave structure along the axis 605. The main magnetic coils 601a and the rest main magnetic coils in the left/right chamber of the cryostat 603 may form a step structure. The main magnetic coils 601a may have a larger radius from the axis 605 than that of the rest main magnetic coils. Further, a gap 606 may be formed between the main magnetic coils 601a, allowing the radiation beam to pass through. In some embodiments, no main magnetic coil is arranged to surround the concave along the axis 605, and thus all the plurality of main magnetic coils 601 may be arranged to surround the inner walls of the cryostat 603 and have the same radius from the axis 605.

Figure 6B:
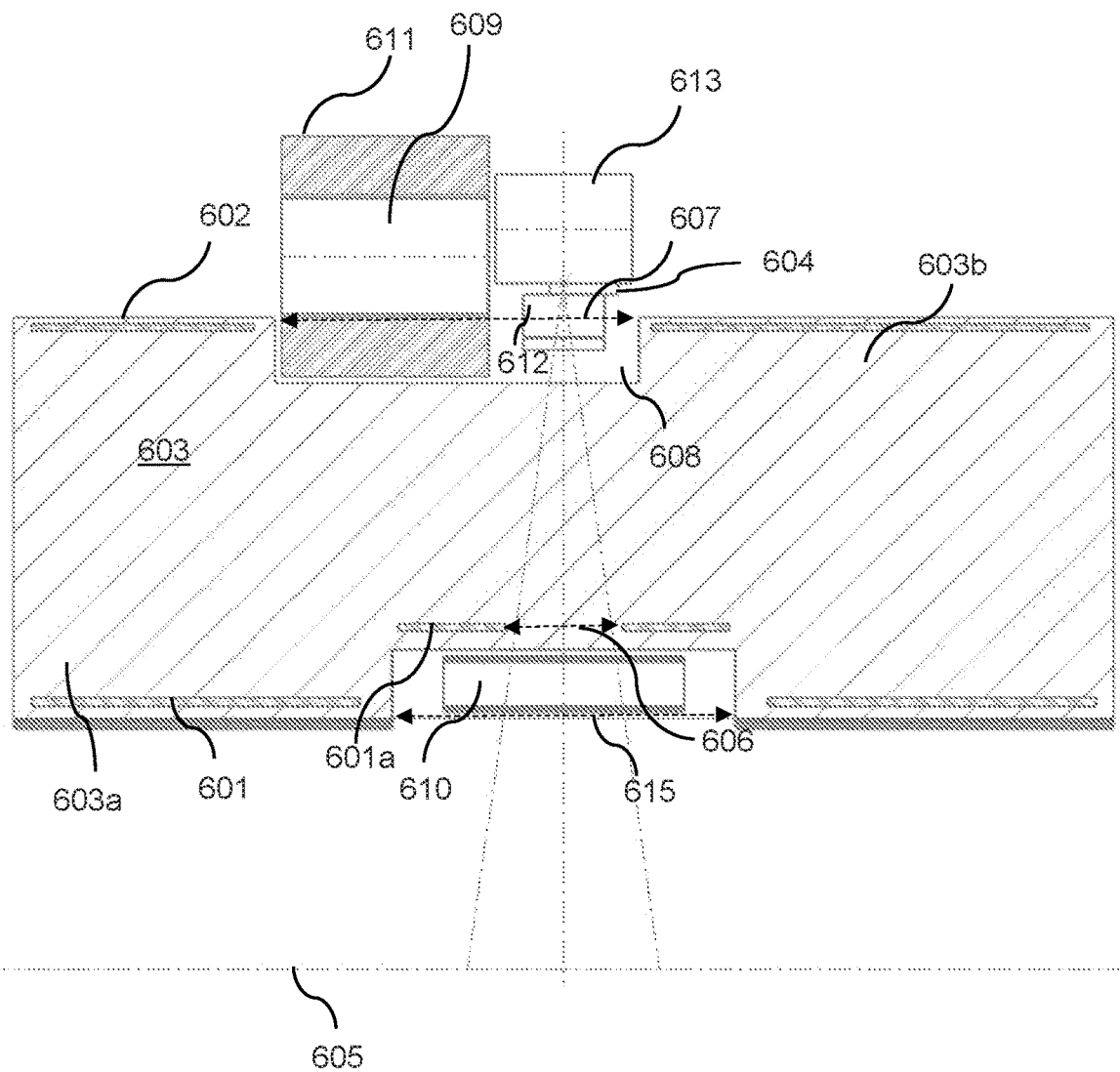
FIG. 6B shows an upper portion of a cross-sectional view of another exemplary therapeutic apparatus viewed along the X direction according to some embodiments of the present disclosure.

FIG. 6B shows an upper portion of a cross-sectional view of an exemplary therapeutic apparatus 600' viewed along the X direction according to some embodiments of the present disclosure. Compared with the therapeutic apparatus 600 described in FIG. 6A, at least part of the linear accelerator 609 of the therapeutic apparatus 600' may be located at the outside of the recess 608 along the radial direction of the cryostat 603. As shown in FIG. 6B, the linear accelerator 609, the shielding structure 611 and the deflection unit 613 may at least partially stretch out of the opening 607 formed by the outer walls of the cryostat 603. In some embodiments, the linear accelerator 609, the shielding structure 611, and the deflection unit 613 may be supported by or mounted to a gantry or a drum (e.g., the gantry 306 or the drum 312) that is capable of rotating around the axis 605.

Figure 7A:
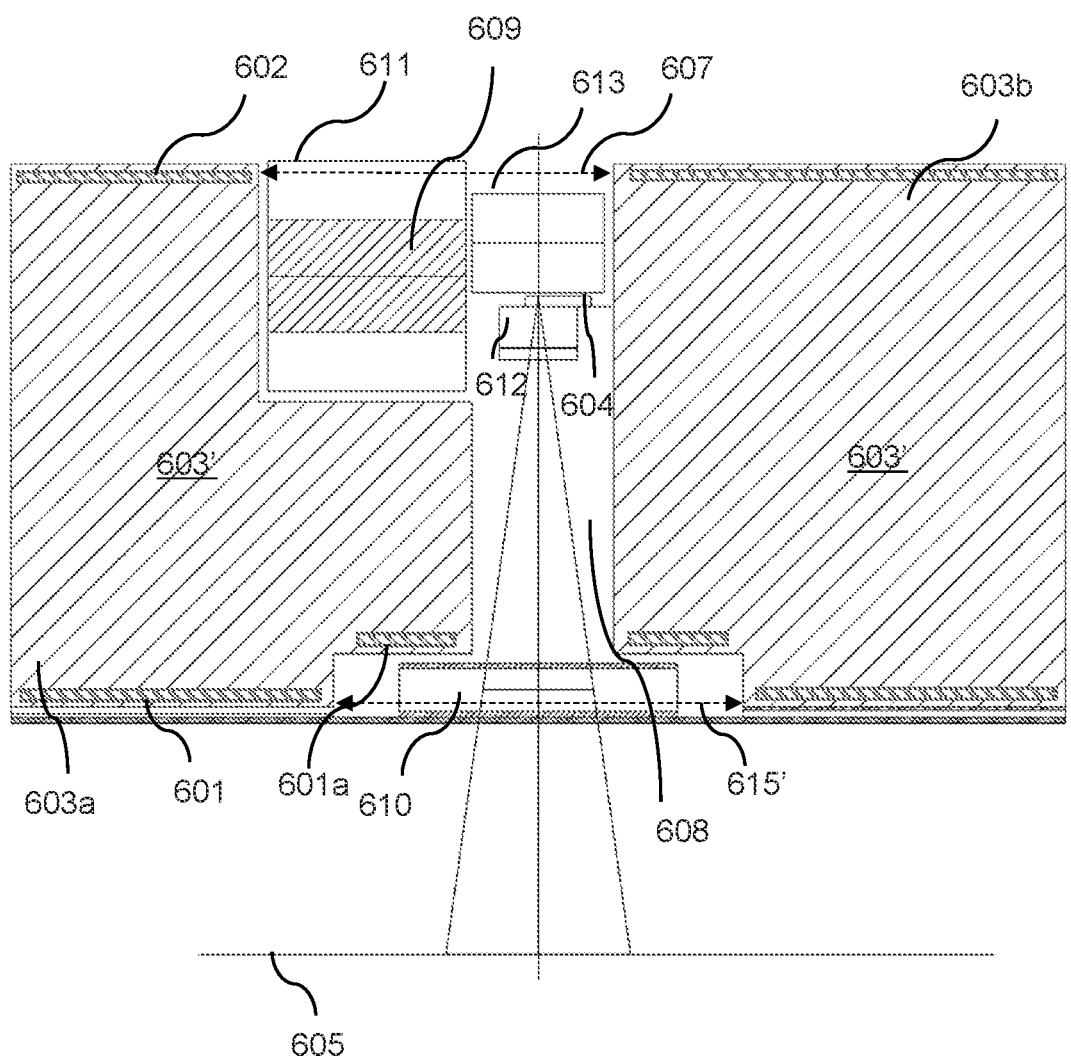
FIG. 7A shows an upper portion of a cross-sectional view of another exemplary therapeutic apparatus viewed along the X direction according to some embodiments of the present disclosure.

FIG. 7A shows an upper portion of a cross-sectional view of another exemplary therapeutic apparatus 600" viewed along the X direction according to some embodiments of the present disclosure. Compared with the therapeutic apparatus 600 described in FIG. 6A, the cryostat 603' of therapeutic apparatus 600" may have two isolated chambers. The concave structure of the cryostat 603' may be connected with the recess 608, forming a larger annulus around the axis 605. In this case, no portion of the cryostat 603 lies in the path of the radiation beam.

In some embodiments, to achieve the synchronous rotation of the linear accelerator and the MLC, various mechanisms may be used. For example, in FIG. 6A, a sliding structure (e.g., a sliding rail, not shown) may be mounted on the MLC 610. When the linear accelerator 609 is rotated by a gantry or a drum as described above, the MLC 610 may synchronously move along the inner wall of the cryostat 603 by the sliding structure to stay fixed relative to the linear accelerator 609. The movement of the MLC 610 may be controlled according to an instruction generated by the one or more processing engines 120. As another example, in FIG. 7A, the MCL 610 may be mechanically connected to the linear accelerator 609 via a rigid structure (e.g., two or more rods, one or more plate, not shown). To reduce the width of the recess 608 along the direction of the axis 605, the two or more rods may be arranged at different circumferential positions of the recess 608 with respect to the linear accelerator 609. For example, the two or more rods may be located at both the left side and the right side of the linear accelerator 609 when viewed along the axis 605. It shall be noted that the mechanisms to achieve the synchronous rotation of the linear accelerator and the MLC is not limited to the descriptions above, any modification or adjustment may be performed according to different scenarios. For example, in FIG. 7A, the MLC 610 may also move along a sliding structure to achieve the synchronous rotation with the linear accelerator 609.

Figure 7B:
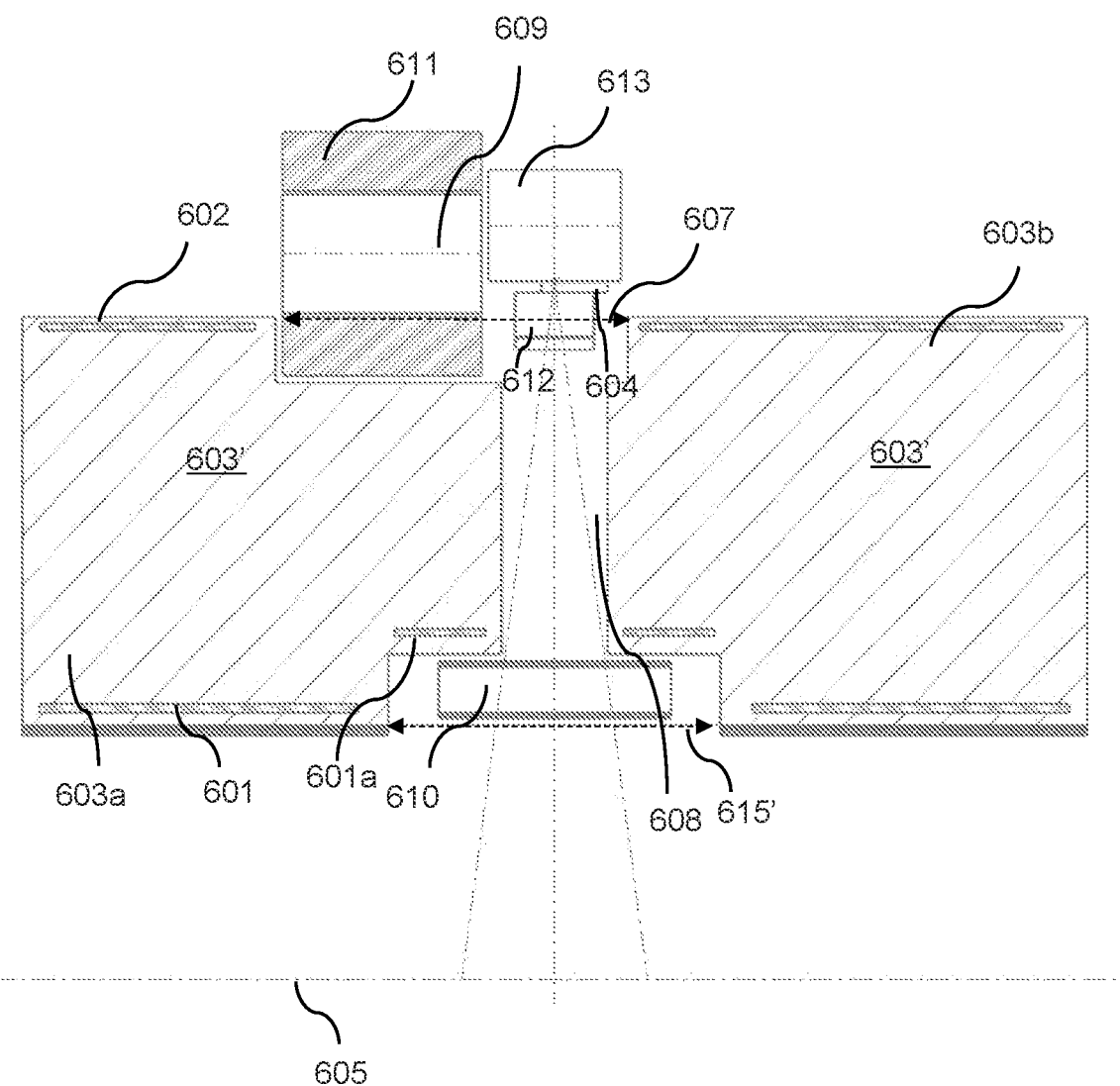
FIG. 7B shows an upper portion of a cross-sectional view of another exemplary therapeutic apparatus viewed along the X direction according to some embodiments of the present disclosure.

FIG. 7B shows an upper portion of a cross-sectional view of an exemplary therapeutic apparatus 600''' viewed along the X direction according to some embodiments of the present disclosure. Compared with the therapeutic apparatus 600" described in FIG. 7A, at least part of the linear accelerator 609 of the therapeutic apparatus 600''' may be located at the outside of the recess 608 along the radial direction of the cryostat 603'. As shown in FIG. 7B, the linear accelerator 609, the shielding structure 611 and the deflection unit 613 may at least partially stretch out of the opening 607 formed by the outer walls of the cryostat 603'. In some embodiments, the linear accelerator 609, the shielding structure 611, and the deflection unit 613 may be supported by or mounted to a gantry or a drum (e.g., the gantry 306 or the drum 312) that is capable of rotating around the axis 605.

It should be noted that the above description of the therapeutic apparatus 600, 600', 600", or 600''' is merely provided for the purposes of illustration, and not intended to limit the scope of the present disclosure. For persons having ordinary skills in the art, multiple variations and modifications may be made under the teachings of the present disclosure. For example, the neck portion illustrated in the cryostat 603 may not form an entire annulus. Specifically, the neck portion may be discrete arcs that connect the left chamber and the right chamber of the cryostat 603. Therefore, the neck portion may intermittently appear in the path of the radiation beam when the linear accelerator 609 rotates around the axis 605 to generate the radiation beam.

As described elsewhere in the present disclosure, the MRI apparatus and the radiation therapy apparatus may interfere with and impair the proper operations of each other. Merely by way of example, the magnetic field produced by the main magnetic coils and the shielding magnetic coils of the MRI apparatus may interfere with the accelerating of the electron beam in the linear accelerator of the radiation therapy apparatus. In order to prevent such interference, the shielding structures described above may at least include a magnetic shielding arrangement to isolate the linear accelerator from the magnetic field. For brevity, the magnetic shielding arrangement shall at least provide a pathway near the linear accelerator that is easier for the magnetic field to pass through, such that the magnetic field may bypass the linear accelerator. In some embodiments, the magnetic shielding arrangement may include one or more magnetic shielding structures that are made of high magnetic susceptibility and/or permeability materials. The one or more magnetic shielding structures may include at least one magnetic shielding plate or layer continuously distributed along the axial direction of the cryostat, providing a continuous pathway for the magnetic field to pass through. The one or more magnetic shielding structures may surround or substantially surround the linear accelerator, such that the magnetic field near the linear accelerator may be conducted through the one or more magnetic shielding structures instead of the space where the linear accelerator locates. As used herein, the substantially surrounding may denote that one or more slots may be formed on the one or more magnetic shielding structures, provided that at least one continuous pathway along the axis of the cryostat exists for the magnetic field to pass through. More details regarding the configuration of the magnetic shielding arrangement may be described below.

Figure 8A:
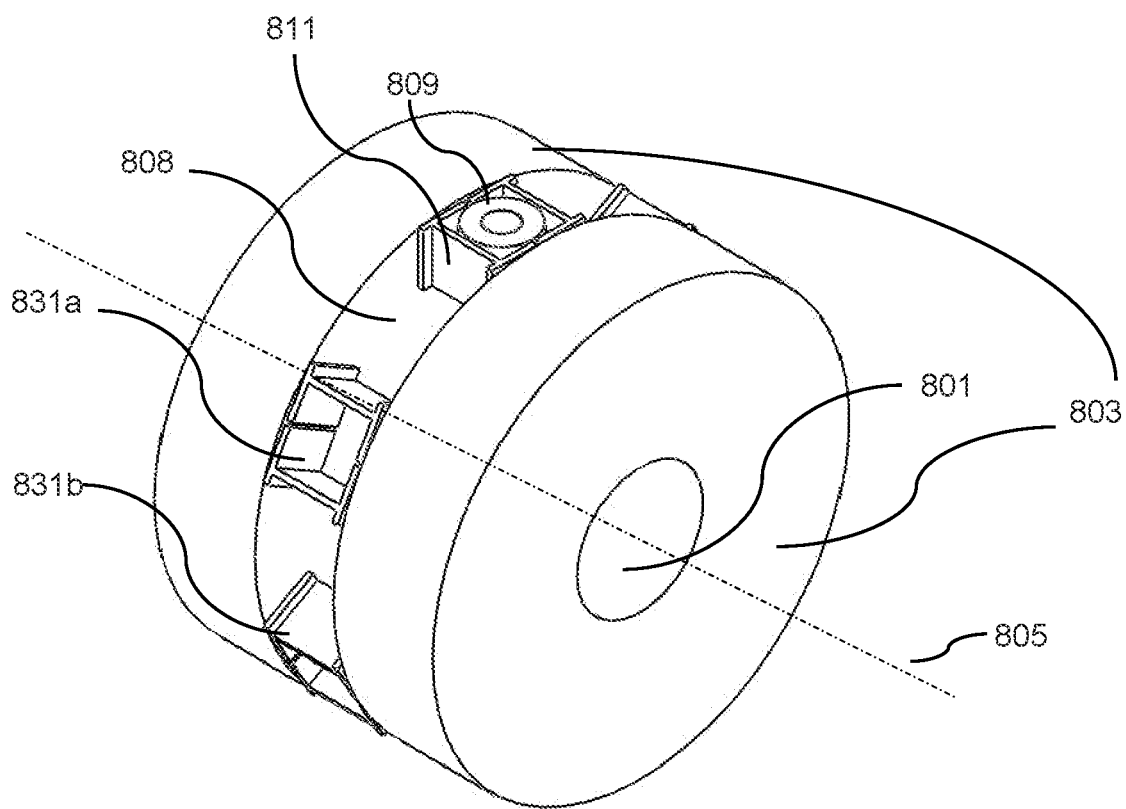
FIG. 8A shows a perspective view of an exemplary therapeutic apparatus according to some embodiments of the present disclosure.

FIG. 8A shows a perspective view of an exemplary therapeutic apparatus 800 according to some embodiments of the present disclosure.

As shown in FIG. 8A, the therapeutic apparatus 800 may include a bore 801, an annular cryostat 803 with an axis 805, a recess 808, a linear accelerator 809, and a magnetic shielding arrangement. The cryostat 803, the axis 805, the recess 808, the linear accelerator 809 may be similar to the cryostat 403, 403', 503, 503', 603, or 603', the axis 405, 505, or 605, the recess 408, 508, or 608, the linear accelerator 409, 509, or 609 and the descriptions are not repeated here.

The magnetic shielding arrangement may include a plurality of magnetic shielding structures including, for example, a magnetic shielding structure 811, a magnetic shielding structure 831a, a magnetic shielding structure 831b, etc. The linear accelerator 809 may be surrounded or substantially surrounded by the magnetic shielding structure 811. The magnetic shielding structure 811 may include a first plate located at one side of the linear accelerator 809 along the circumferential direction of the recess 808 and a second plate located at the opposite side of the linear accelerator 809 along the circumferential direction of the recess 808. The first plate and the second plate may be symmetrical to each other with respect to the axis of the linear accelerator 809. The first plate and the second plate may form an enclosing structure to surround and/or hold the linear accelerator 809. Each of the two plates may have a shape similar to the symbol "工", which provides a continuous pathway along the axial direction (i.e., the direction of the axis 805) of the cryostat 803 for the magnetic field to pass through. In that the two plates of the magnetic shielding structure 811 are made of high magnetic susceptibility and/or permeability materials, the magnetic field may be conducted by the two plates and kept from the region formed between them, thus achieving the magnetic shielding for the linear accelerator 909. In some embodiments, each of the two plates may be radially arranged about the axis 805, and at least one side of each of the two plates may point to the axis 805.

In some embodiments, the first plate and the second plate may be connected to each other at both sides of the linear accelerator 909 along the axial direction of the cryostat 803, thus forming a closed loop around the linear accelerator 909. In some embodiments, the first plate and the second plate may be separate from each other at both sides of the linear accelerator 909 along the axial direction of the cryostat 803, thus forming a semi-closed loop substantially around the linear accelerator 909. It shall be noted that the configuration of the magnetic shielding structure 811 is not limited, any other configurations (e.g., a hollow cylinder or other shape with curved sides) may also be used to achieve the magnetic shielding.

Additionally, the presence of the magnetic shielding structure 811 within the magnetic field of the MRI apparatus may exert an influence on the magnetic field (e.g., deform the distribution and cause the in-homogeneity of the magnetic field). In order to correct the deformation of the magnetic field caused by the magnetic shielding structure 811, similar magnetic shielding structures of the magnetic shielding arrangement, including the magnetic shielding structure 831a, the magnetic shielding structure 831b, etc., may also be placed within the recess 808. In some embodiments, all the magnetic shielding structures may be identical to each other. For example, the magnetic shielding structure 831a and the magnetic shielding structure 831b may be made of identical materials and have the identical structure as the magnetic shielding structure 811. The magnetic shielding structure 811, the magnetic shielding structure 831a, the magnetic shielding structure 831b, etc., may be mounted on the gantry or the drum (not shown) of therapeutic apparatus 800 to achieve the synchronous rotation with the linear accelerator 809.

In some embodiments, the magnetic shielding structure 811, the magnetic shielding structure 831a, the magnetic shielding structure 831b, etc., may be placed at selected symmetrical circumferential locations about the axis 805. For example, all the magnetic shielding structures may be evenly distributed within the recess 808. Each magnetic shielding structure may correspond to an opposite or opposing counterpart. Each magnetic shielding structure and its counterpart may be symmetrical about the axis 805. As used herein, two magnetic shielding structures may be regarded as opposite or opposing if the two magnetic shielding structures are symmetric about the axis 805.

Figure 8B:
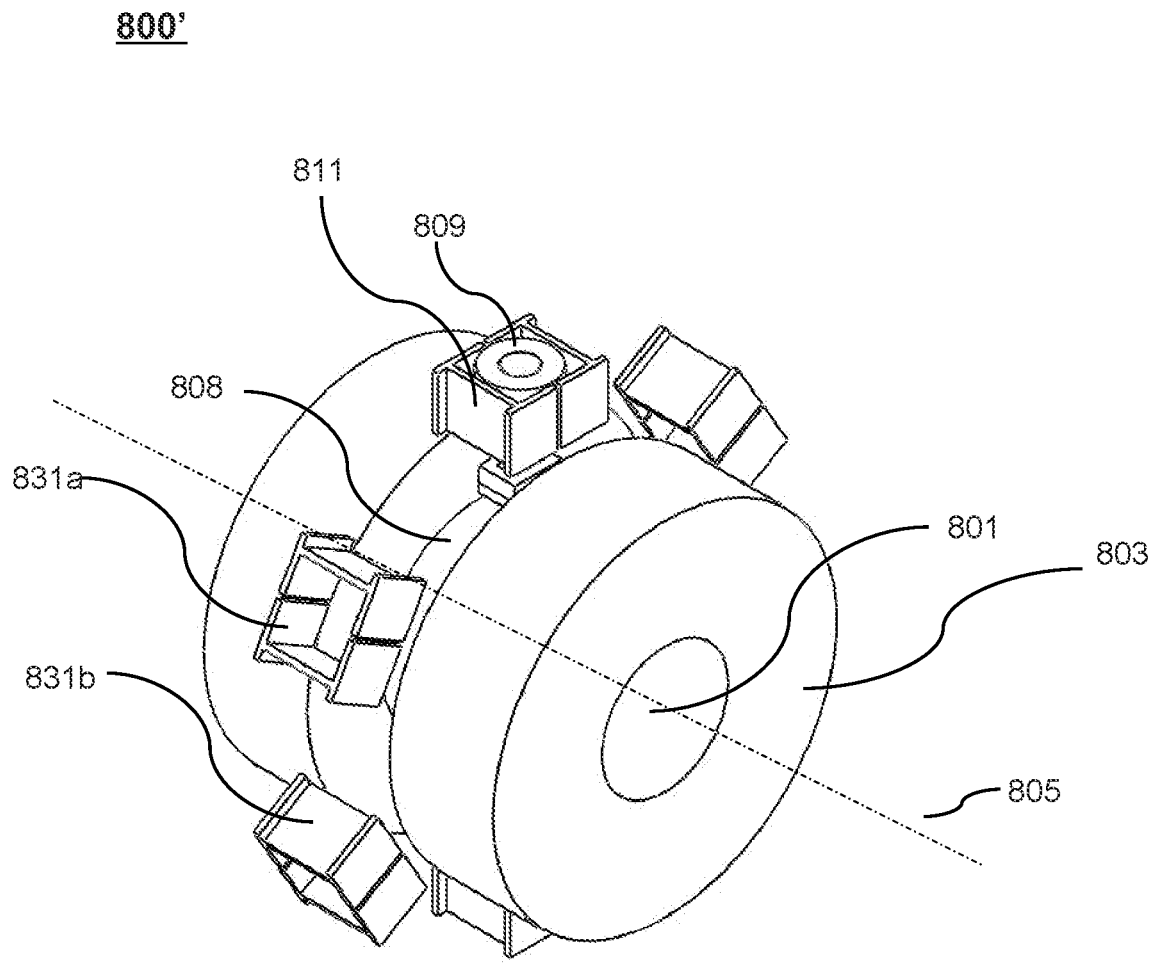
FIG. 8B shows a perspective view of an exemplary therapeutic apparatus according to some embodiments of the present disclosure.

FIG. 8B shows a perspective view of an exemplary therapeutic apparatus 800' according to some embodiments of the present disclosure. Compared with the therapeutic apparatus 800 described in FIG. 8A, at least part of the linear accelerator 809 of the therapeutic apparatus 800' may be located at the outside of the recess 808 along the radial direction of the cryostat 803. As shown in FIG. 8B, the linear accelerator 809 and the magnetic shielding structure 811 surrounding the linear accelerator 809 may stretch out of the opening of the recess 808 formed by the outer walls of the cryostat 803. Similarly, the magnetic shielding structures 831a, 831b, etc., may also stretch out of the opening of the recess 808, thus maintaining the symmetry of the magnetic shielding structures with respect to the axis 805. In some embodiments, the linear accelerator 809 and all the magnetic shielding structures may be supported by or mounted to a gantry or a drum (e.g., the gantry 306 or the drum 312) that is capable of rotating around the axis 805.

Figure 9A:
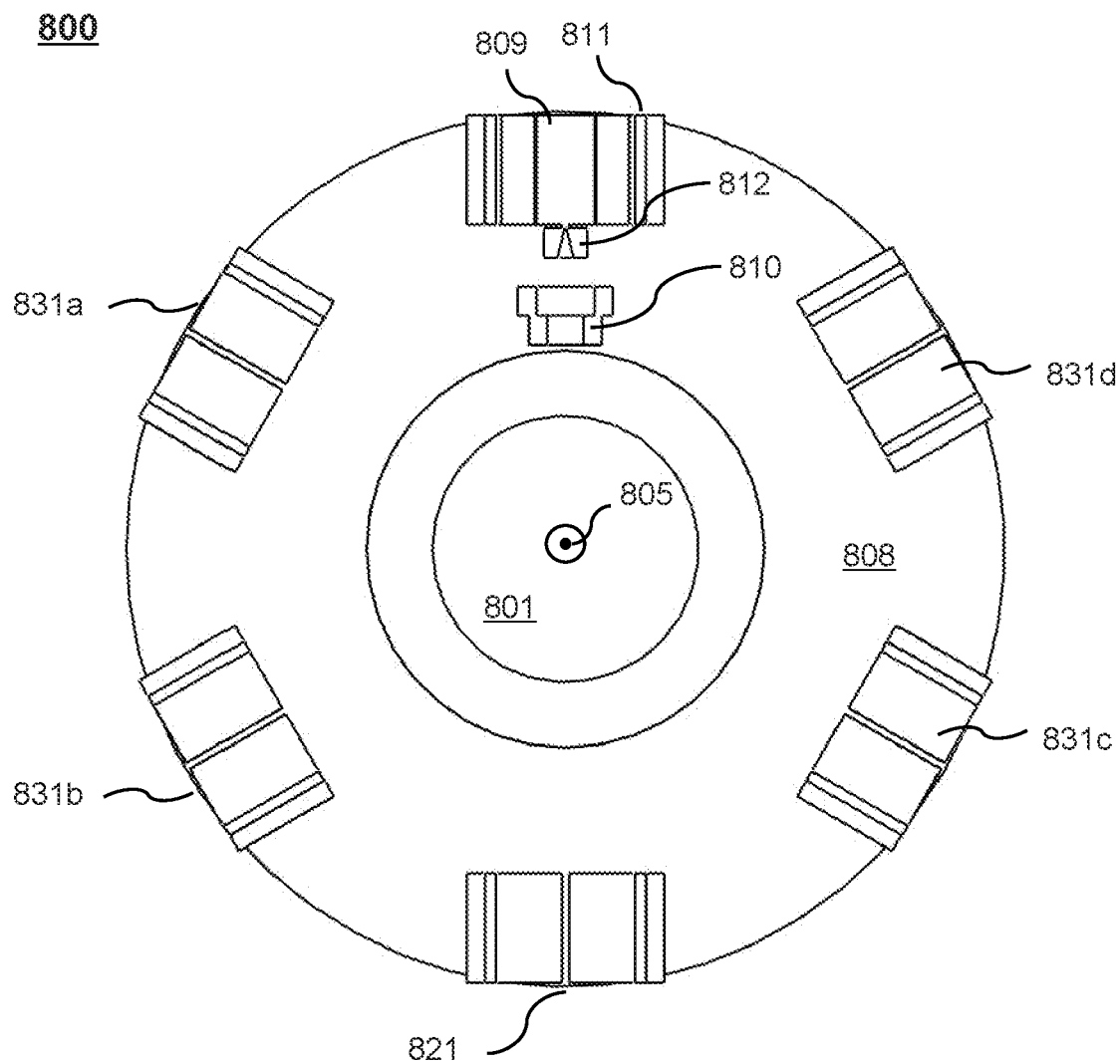
FIG. 9A shows a cross-sectional view of the therapeutic apparatus described in FIG. 8A viewed along the axial direction of the cryostat according to some embodiments of the present disclosure.

FIG. 9A shows the cross-sectional view of the therapeutic apparatus 800 viewed along the axial direction (i.e., the Z direction) of the cryostat according to some embodiments of the present disclosure. The linear accelerator 809, the collimator 812 and the MLC 810 may be similar to the linear accelerator 409, 509, or 609, the collimator 412, 512, or 612, and the MLC 410, 510, or 610, and the descriptions are not repeated here.

As shown in FIG. 9A, the magnetic shielding structure 811, the magnetic shielding structure 821, and the magnetic shielding structures 831a, 831b, 831c, 831d may be evenly distributed within the recess 808 and around the axis 805 of the bore 801. The distances between each two adjacent magnetic shielding structures may be the same. The magnetic shielding structure 821 may be the opposite or opposing counterpart of the magnetic shielding structure 811. The magnetic shielding structure 821 may be identical to the magnetic shielding structure 811 if it rotates clockwise 180 degrees to the position of the magnetic shielding structure 811 around the axis 805. All the magnetic shielding structures may be fixed with respect to the linear accelerator 809, and thus may rotate synchronously with the linear accelerator 809.

Figure 9B:
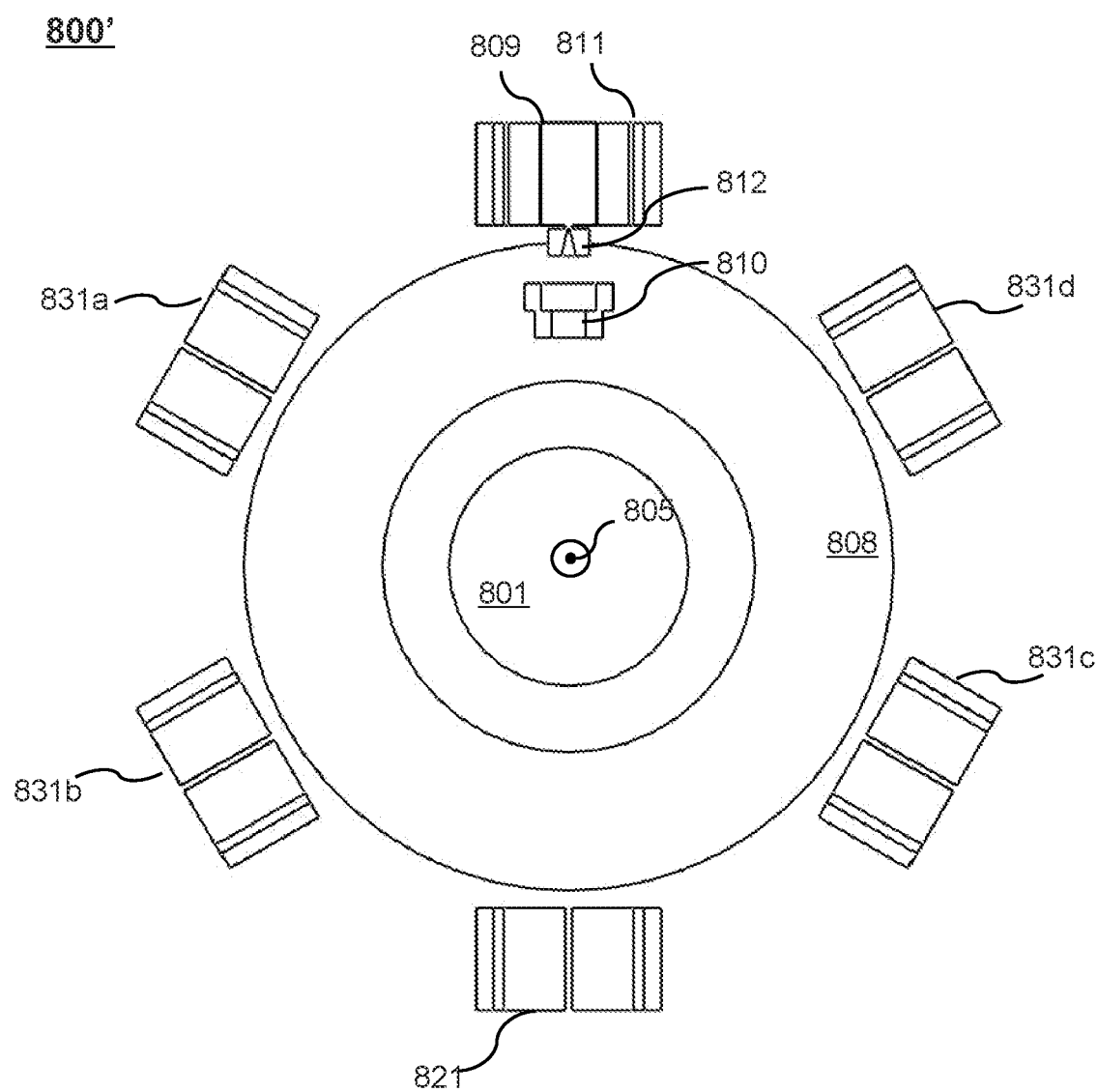
FIG. 9B shows the cross-sectional view of the therapeutic apparatus described in FIG. 8B viewed along the axial direction (i.e., the Z direction) of the cryostat according to some embodiments of the present disclosure.

FIG. 9B shows the cross-sectional view of the therapeutic apparatus 800' viewed along the axial direction (i.e., the Z direction) of the cryostat according to some embodiments of the present disclosure. As described in connection with FIG. 8B, as shown in FIG. 9B, at least part of the linear accelerator 809 of the therapeutic apparatus 800' may be located at the outside of the recess 808 along the radial direction of the cryostat 803.

Figure 10A:
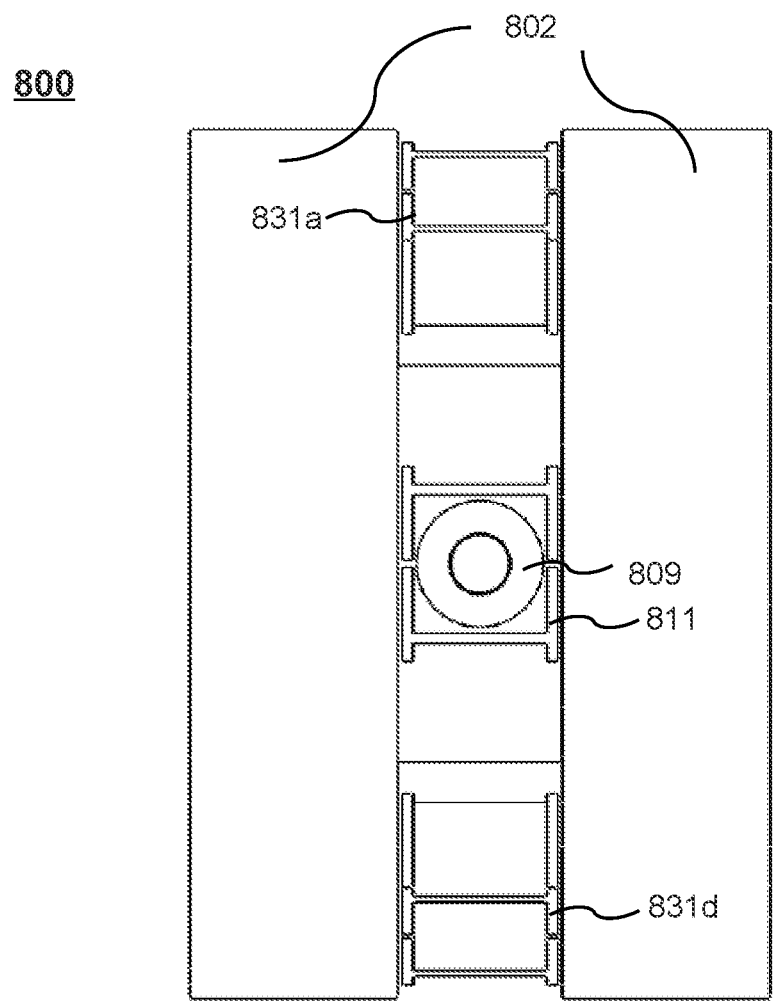
FIG. 10A shows another the cross-sectional view of the therapeutic apparatus described in FIG. 8A according to some embodiments of the present disclosure.

FIG. 10A shows the cross-sectional view of the therapeutic apparatus 800 viewed along the Y direction according to some embodiments of the present disclosure.

Figure 10B:
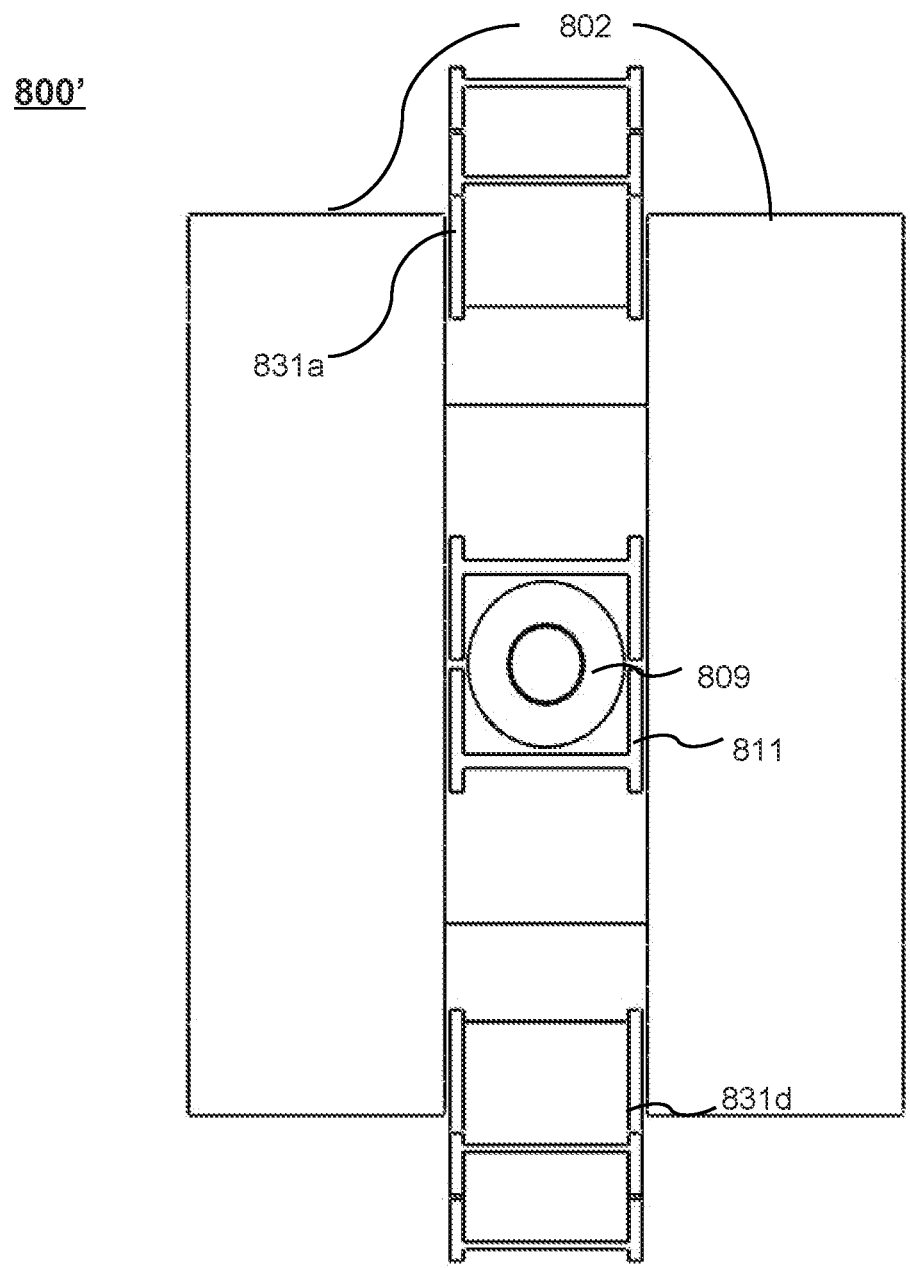
FIG. 10B shows the cross-sectional view of the therapeutic apparatus described in FIG. 8B viewed along the Y direction according to some embodiments of the present disclosure.

FIG. 10B shows the cross-sectional view of the therapeutic apparatus 800' viewed along the Y direction according to some embodiments of the present disclosure.

Figure 11A:
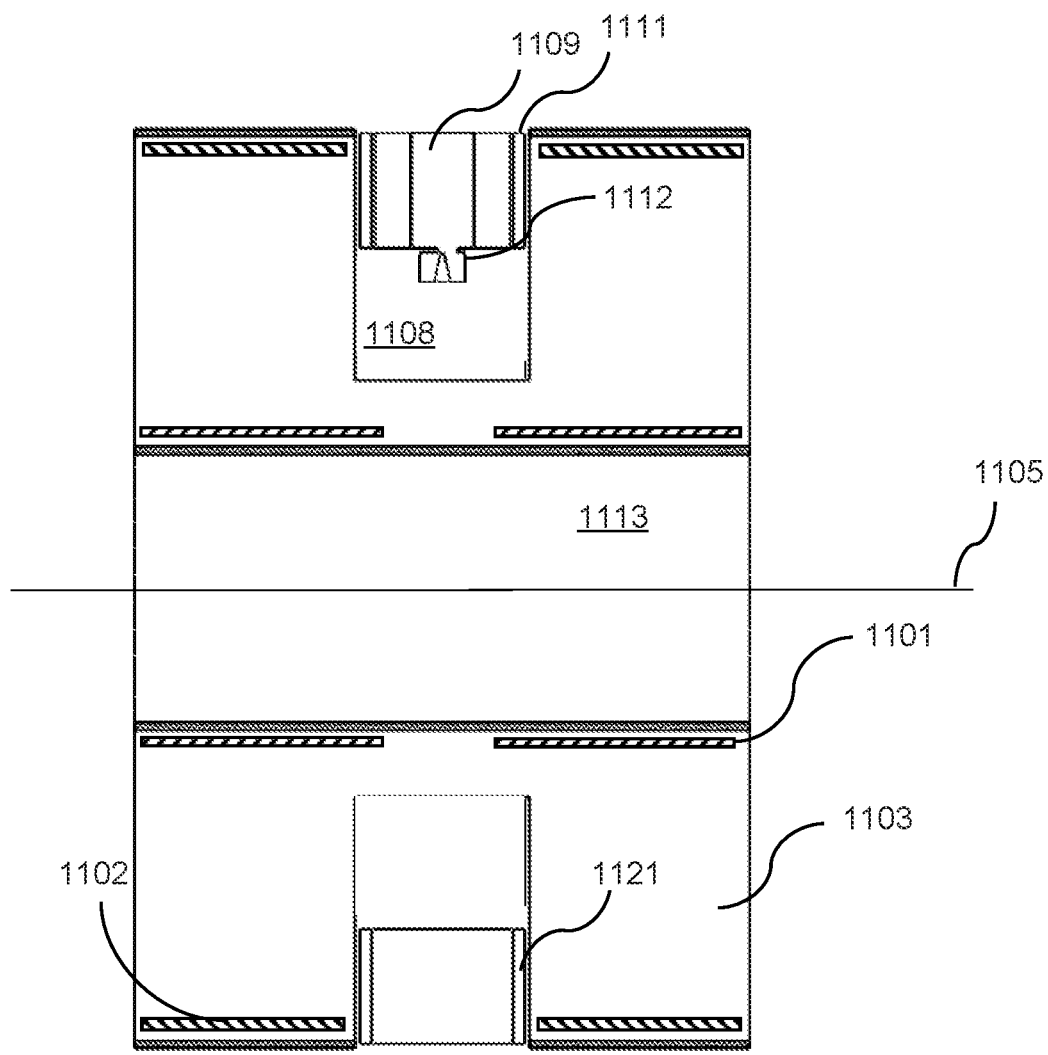
FIG. 11A shows a cross-sectional view of an exemplary therapeutic apparatus viewed along the X direction according to some embodiments of the present disclosure.

It shall be noted that the number of magnetic shielding structures in the magnetic shielding arrangement is not limited. Any number of magnetic shielding structures may be used in the therapeutic apparatus, provided that a symmetry of the magnetic shielding structures is achieved. FIG. 11A shows a cross-sectional view of an exemplary therapeutic apparatus 1100 having two magnetic shielding structures viewed along the X direction according to some embodiments of the present disclosure. As shown in FIG. 11A, the therapeutic apparatus 1100 may include a plurality of main magnetic coils 1101, a plurality of shielding magnetic coils 1102, an cryostat 1103 with an axis 1105, a recess 1108, a linear accelerator 1109, a first magnetic shielding structure 1111, a collimator 1112, a second magnetic shielding structure 1121, and a bore 1113. The plurality of main magnetic coils 1101, the plurality of shielding magnetic coils 1102, the cryostat 1103, the axis 1105, the recess 1108, the linear accelerator 1109, and the collimator 1112 may be similar to the plurality of main magnetic coils 401, 501, or 601, the plurality of shielding magnetic coils 402, 502, or 602, the cryostat 403, 403', 503, 503', 603, 603', or 803, the axis 405, 505, 605, or 805, the recess 408, 508, 608, or 808, the linear accelerator 409, 509, 609, or 809, and the collimator 412, 512, 612, or 812, and the descriptions are not repeated here.

The second magnetic shielding structure 1121 may be the opposite or opposing counterpart of the first magnetic shielding structure 1111 and may be configured to reduce the field in-homogeneity caused by the presence of the first magnetic shielding structure 1111. The second magnetic shielding structure 1121 and the first magnetic shielding structure 1111 may form a symmetrical structure within the magnetic field of the MRI apparatus. That is, the second magnetic shielding structure 1121 may be located within the recess 1108 and be at the opposite position of the first magnetic shielding structure 1111 with respect to the axis 1105. The second magnetic shielding structure 1121 may be made of the identical materials and have the identical structure as the first magnetic shielding structure 1121. For example, the second magnetic shielding structure 1121 may be identical to the first magnetic shielding structure 1111 if it rotates 180 degrees to the position of the first magnetic shielding structure 1111 around the axis 1105.

Figure 11B:
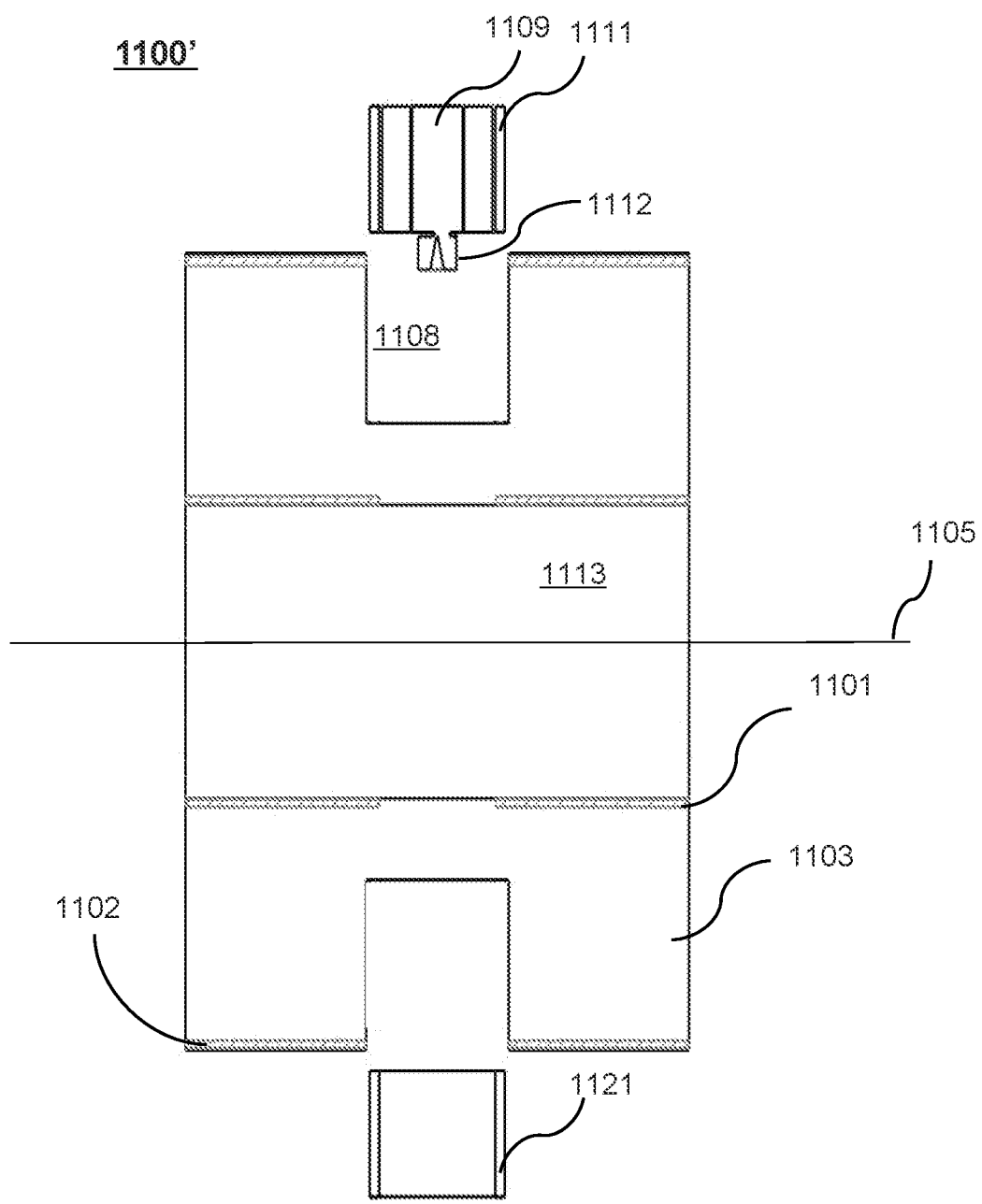
FIG. 11B shows another exemplary therapeutic apparatus having two magnetic shielding structures viewed along the X direction according to some embodiments of the present disclosure.

FIG. 11B shows an exemplary therapeutic apparatus 1100' having two magnetic shielding structures viewed along the X direction according to some embodiments of the present disclosure. Compared with the therapeutic apparatus 1100 described in FIG. 11A, at least part of the linear accelerator 1109 of the therapeutic apparatus 1100' may be located at the outside of the recess 1108 along the radial direction of the cryostat 1103. As shown in FIG. 11B, the linear accelerator 1109, the first shielding structure 1111, and the second magnetic shielding structure 1121 may at least partially stretch out of the opening of the recess 1108 formed by the outer walls of the cryostat 1103. The first shielding structure 1111 and the second magnetic shielding structure 1121 may still be symmetrical about the axis 1105. In some embodiments, the linear accelerator 1109, the first shielding structure 1111, and the second magnetic shielding structure 1121 may be supported by or mounted to a gantry or a drum (e.g., the gantry 306 or the drum 312) that is capable of rotating around the axis 1105.

Figure 12A:
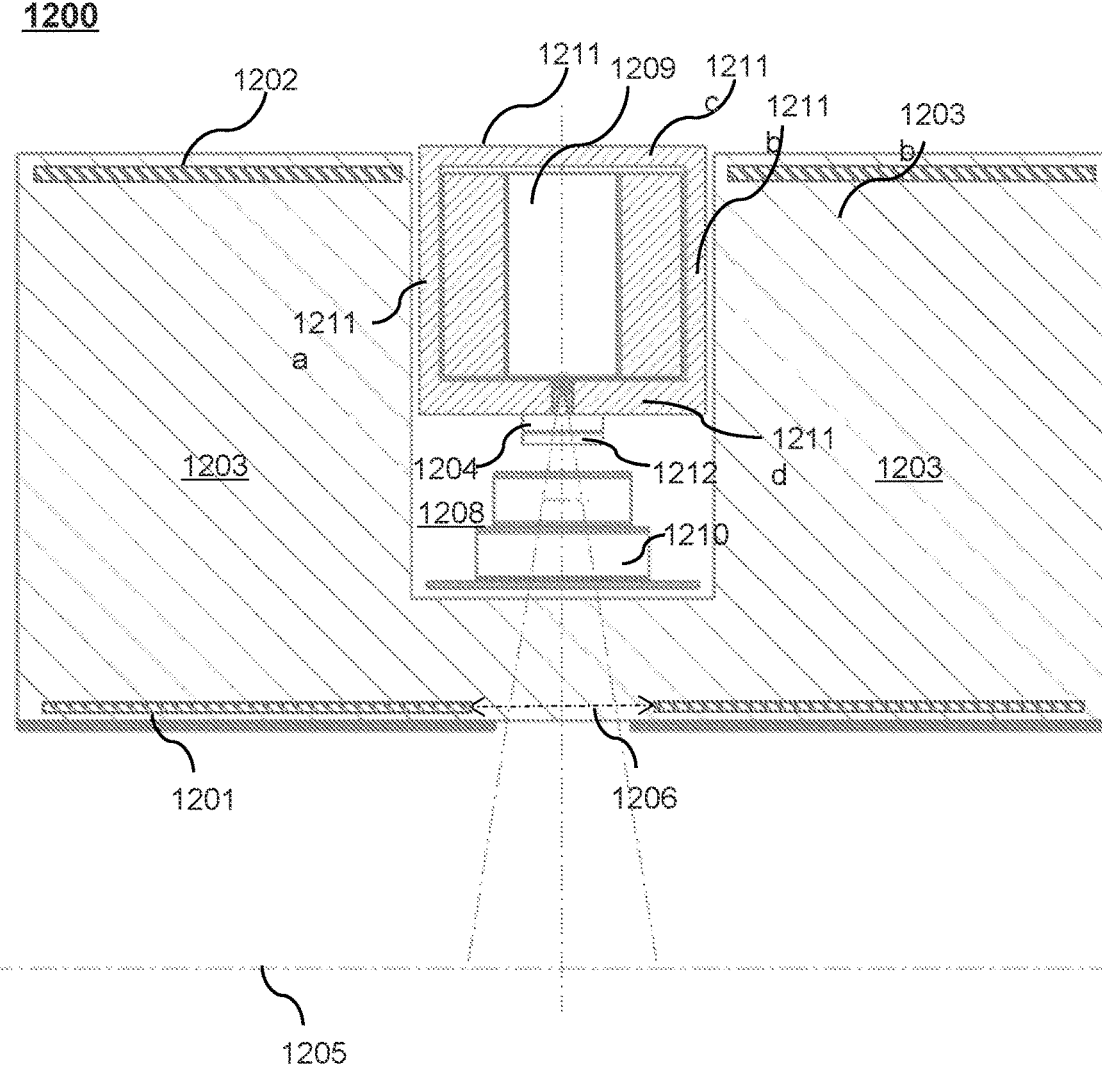
FIG. 12A shows an upper portion of a cross-sectional view of an exemplary therapeutic apparatus viewed along the X direction according to some embodiments of the present disclosure.

FIG. 12A shows an upper portion of a cross-sectional view of an exemplary therapeutic apparatus 1200 viewed along the X direction according to some embodiments of the present disclosure. As shown in FIG. 12A, the therapeutic apparatus 1200 may include a plurality of main magnetic coils 1201, a plurality of shielding magnetic coils 1202, a cryostat 1203, a target 1204, an axis 1205, a gap 1206, a recess 1208, a linear accelerator 1209, an MLC 1210, a magnetic shielding structure 1211, and a collimator 1212. The plurality of main magnetic coils 1201, the plurality of shielding magnetic coils 1202, the cryostat 1203, the target 1204, the axis 1205, the gap 1206, the recess 1208, the linear accelerator 1209, the MLC 1210, and the collimator 1212 may be similar to the plurality of main magnetic coils 401, the plurality of shielding magnetic coils 402, and the cryostat 403, 503, 603, 803, or 1103, the target 404, 504, or 604, the axis 405, 505, 605, 805, or 1105, the gap 406, 506, or 606, the recess 408, 508, 608, 808, or 1108, the linear accelerator 409, 509, 609, 809, or 1109, the MLC 410, 510, 610, or 810, and the collimator 412, 512, 612, 812, or 1112, and the descriptions thereof are not repeated here.

As shown in FIG. 12A, the magnetic shielding structure 1211 may include a first side plate 1211a, a second side plate 1211b, an upside plate 1211c and a downside plate 1211d. The first side plate 1211a and the second side plate 1211b may be placed at opposite sides of the linear accelerator 1209 along the axial direction (i.e., the direction along the axis 1205) of the cryostat 1203. The upper side plate 1211c and the downside plate 1211d may be placed at opposite sides of the linear accelerator 1209 along the axial direction of the linear accelerator 1209. The first side plate 1211a, the second side plate 1211b, the upside plate 1211c and the downside plate 1211d may form a closed loop surrounding the linear accelerator 1209. Provided that each plate is made of high magnetic susceptibility and/or permeability materials, the magnetic field may be conducted by the upside plate 1211c and the downside plate 1211d from one side of the cryostat 1203 to the other side of the cryostat 1203 along the axial direction of the cryostat 1203 (e.g., from the left side to the right side), bypassing the linear accelerator 1209 and thus achieving the magnetic shielding for the linear accelerator 1209. The downside plate 1211d may further provide at least one slot to allow the radiation beam produced by the linear accelerator 1209 to pass through.

Figure 12B:
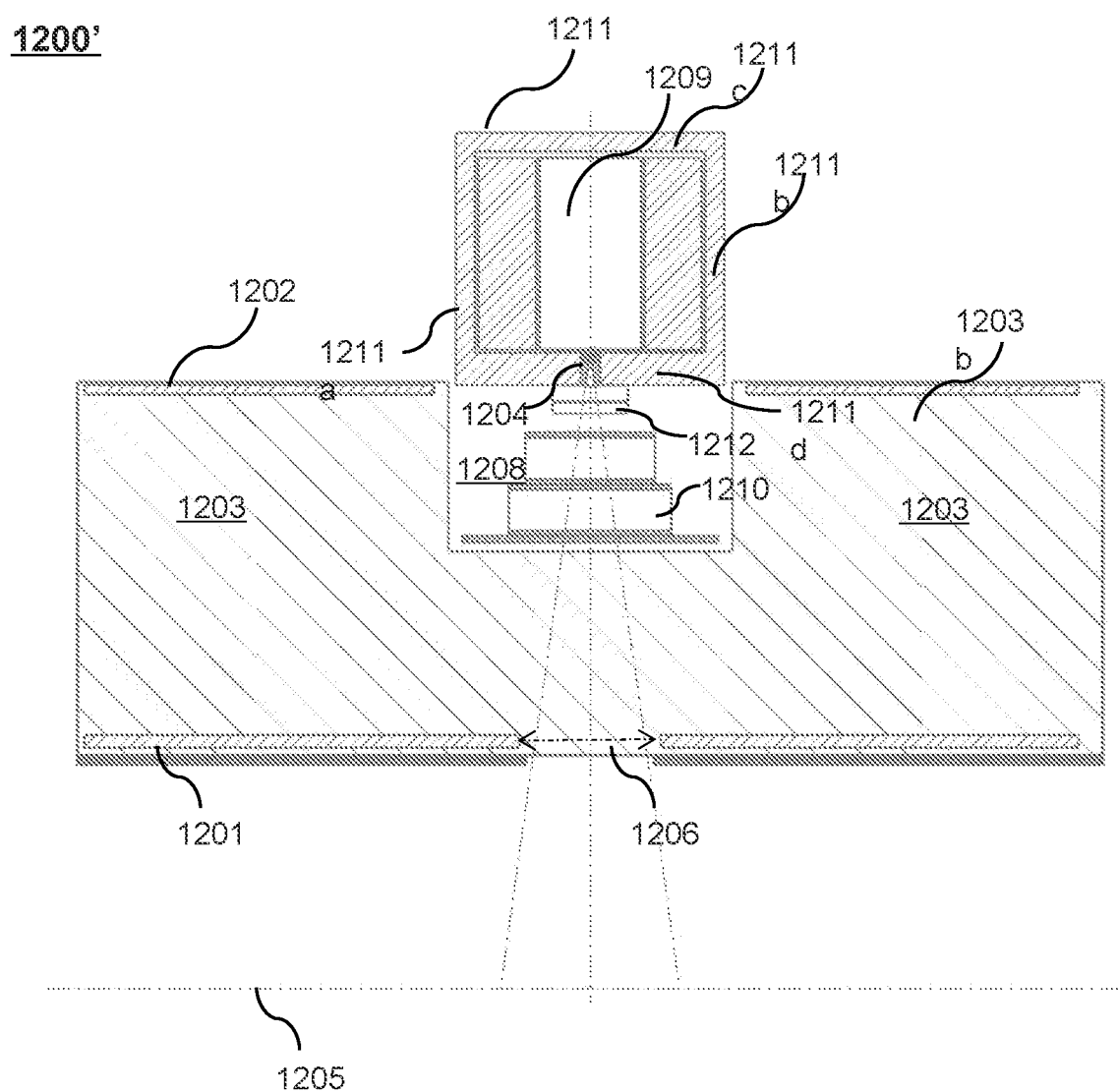
FIG. 12B shows an upper portion of a cross-sectional view of another exemplary therapeutic apparatus viewed along the X direction according to some embodiments of the present disclosure.

FIG. 12B shows an upper portion of a cross-sectional view of an exemplary therapeutic apparatus 1200' viewed along the X direction according to some embodiments of the present disclosure. Compared with the therapeutic apparatus 1200 described in FIG. 12A, at least part of the linear accelerator 1209 of the therapeutic apparatus 1200' may be located at the outside of the recess 1208 along the radial direction of the cryostat 1203. As shown in FIG. 12B, the linear accelerator 1209 and the magnetic shielding structure 1211 may at least partially stretch out of the opening of the recess 1208 formed by the outer walls of the cryostat 1203. Specifically, the first side plate 1211a, the second side plate 1211b, and the upside plate 1211c of the magnetic shielding structure 1211 may stretch out of the opening of the recess 1208. In some embodiments, the linear accelerator 1209 and the magnetic shielding structure 1211 may be supported by or mounted to a gantry or a drum (e.g., the gantry 306 or the drum 312) that is capable of rotating around the axis 1205.

Figure 12C:
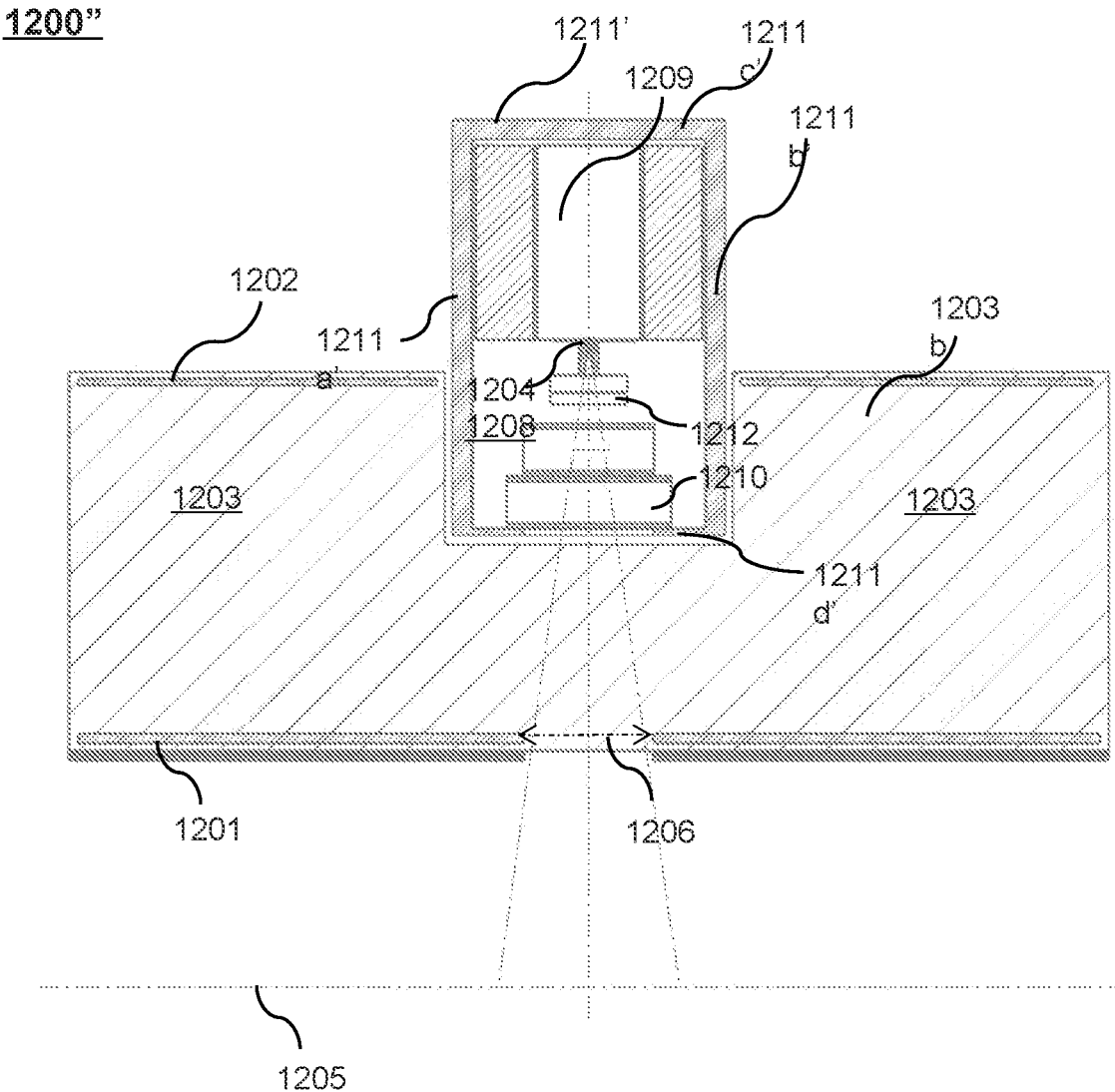
FIG. 12C shows an upper portion of a cross-sectional view of another exemplary therapeutic apparatus viewed along the X direction according to some embodiments of the present disclosure.

FIG. 12C shows an upper portion of a cross-sectional view of an exemplary therapeutic apparatus 1200'' viewed along the X direction according to some embodiments of the present disclosure. Compared with the therapeutic apparatus 1200 described in FIG. 12A and the therapeutic apparatus 1200' described in FIG. 12B, the magnetic shielding structure 1211' of the therapeutic apparatus 1200'' may form a closed loop surrounding the linear accelerator 1209, the collimator 1212, and the MLC 1210. As shown in FIG. 12C, the first side plate 1211a' and the second side plate 1211b' may at least stretch from the innermost radial position of the MLC 1210 to the outermost radial position of the linear accelerator 1209 along the radial direction. The downside plate 1211d' may be located at the innermost side of the MLC 1210 and further provide at least one slot to allow the radiation beam produced by the linear accelerator 1209 to pass through. Therefore, the magnetic shielding structure 1211' may provide magnetic shielding for both of the linear accelerator 1209 and the MLC 1210.

Figure 13A:
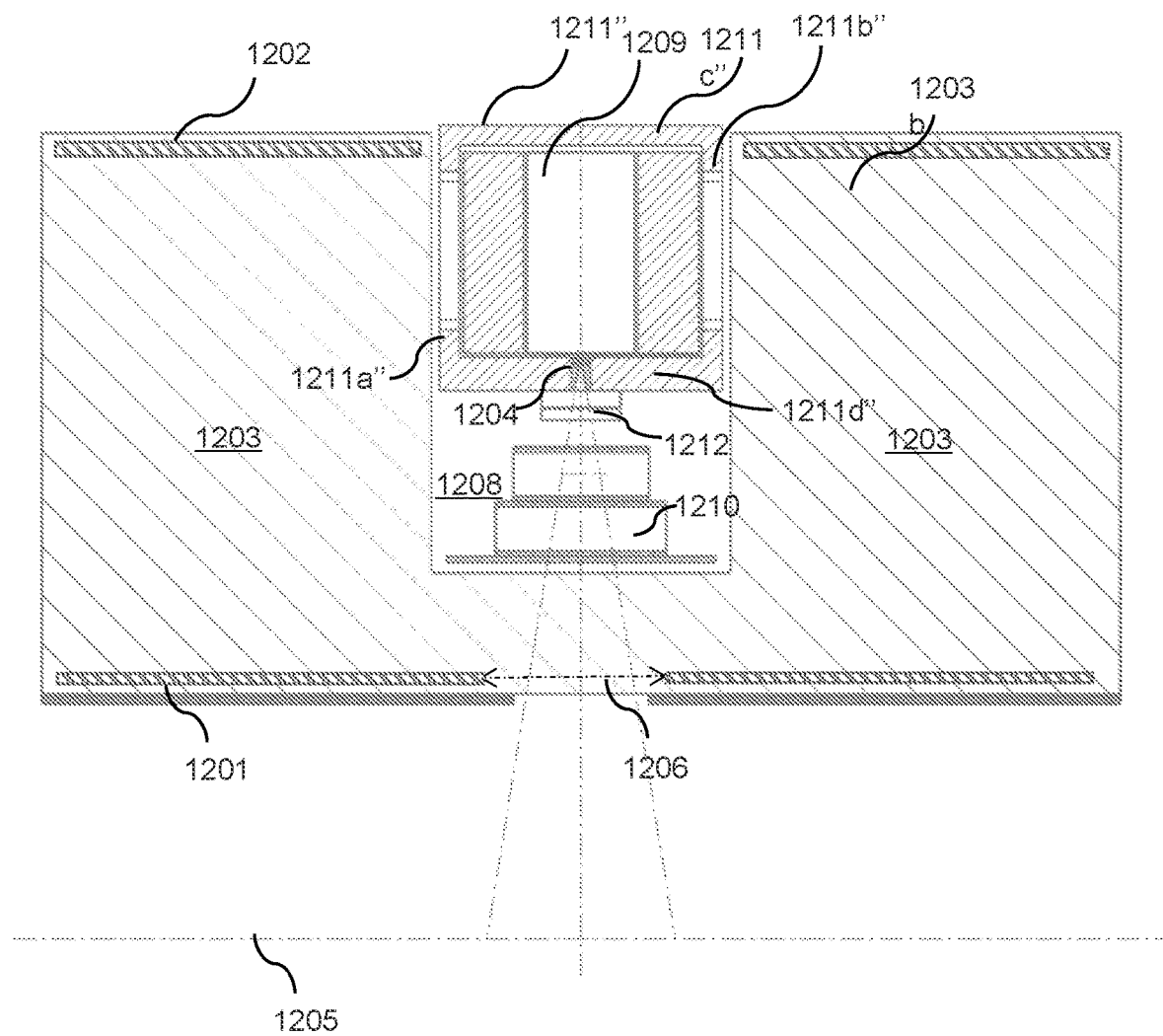
FIG. 13A shows an upper portion of a cross-sectional view of an exemplary therapeutic apparatus viewed along the X direction according to some embodiments of the present disclosure.

FIG. 13A shows an upper portion of a cross-sectional view of an exemplary therapeutic apparatus 1300 viewed along the X direction according to some embodiments of the present disclosure. Compared with the magnetic shielding structure 1211 described in FIG. 12A, the side plate 1211a'' and the side plate 1211b" of the magnetic shielding structure 1211" may both have a slot. The slot may be of any shape, such as a rectangle, an ellipse, or the like. It shall be noted that the magnetic field may still be conducted by the upside plate 1211c" and the downside plate 1211d", provided that the slots are small enough to prevent the magnetic field from entering the linear accelerator 1209 through the slots.

Figure 13B:
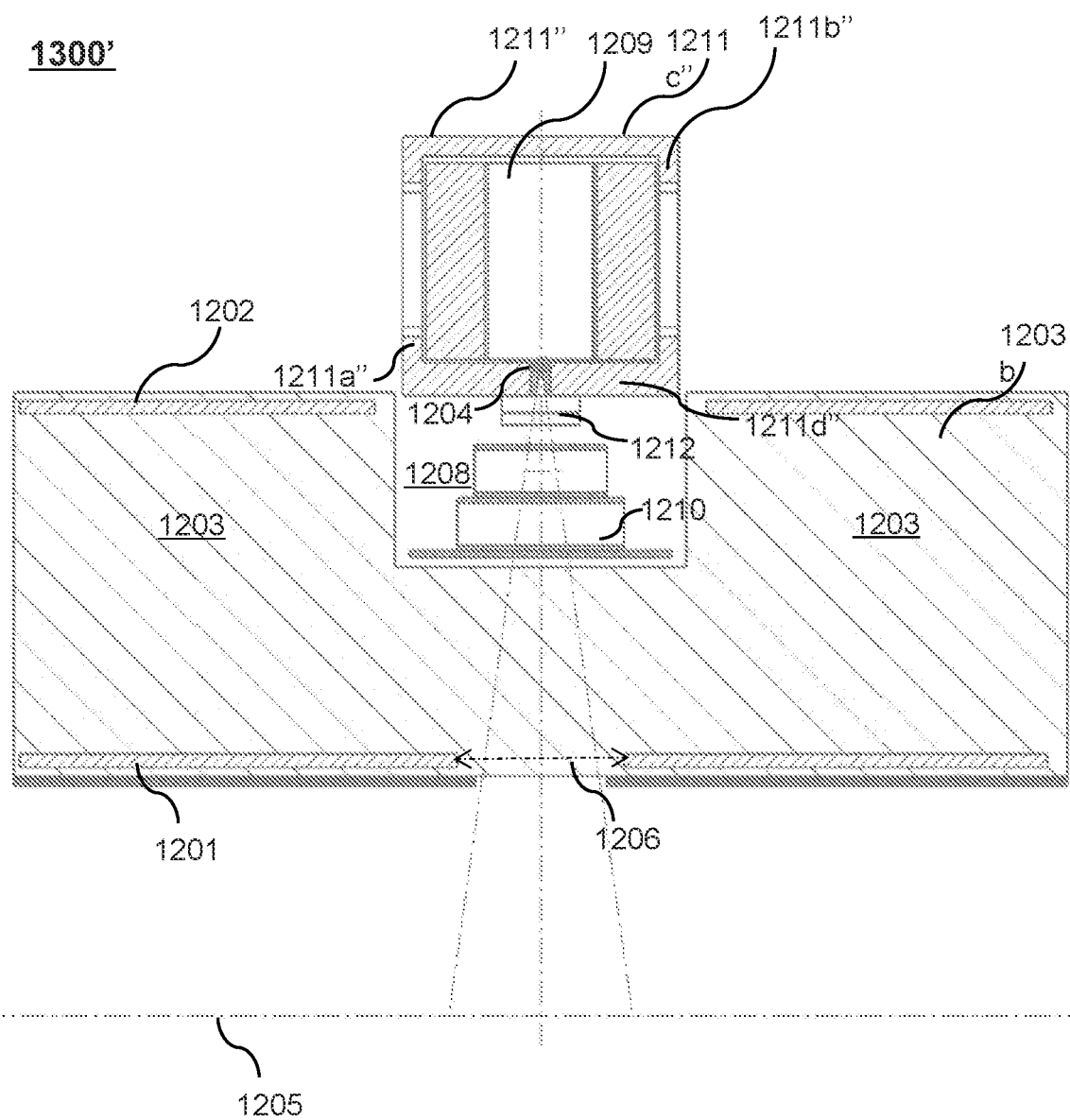
FIG. 13B shows an upper portion of a cross-sectional view of another exemplary therapeutic apparatus viewed along the X direction according to some embodiments of the present disclosure.

FIG. 13B shows an upper portion of a cross-sectional view of an exemplary therapeutic apparatus 1300' viewed along the X direction according to some embodiments of the present disclosure. Compared with the therapeutic apparatus 1300 described in FIG. 13A, at least part of the linear accelerator 1209 of the therapeutic apparatus 1300' may be located at the outside of the recess 1208 along the radial direction of the cryostat 1203. As shown in FIG. 13B, the linear accelerator 1209 and the magnetic shielding structure 1211" may at least partially stretch out of the opening of the recess 1208 formed by the outer walls of the cryostat 1203. Specifically, the first side plate 1211a", the second side plate 1211b", and the upside plate 1211c" of the magnetic shielding structure 1211" may stretch out of the opening of the recess 1208. In some embodiments, the linear accelerator 1209 and the magnetic shielding structure 1211" may be supported by or mounted to a gantry or a drum (e.g., the gantry 306 or the drum 312) that is capable of rotating around the axis 1205.

Figure 13C:
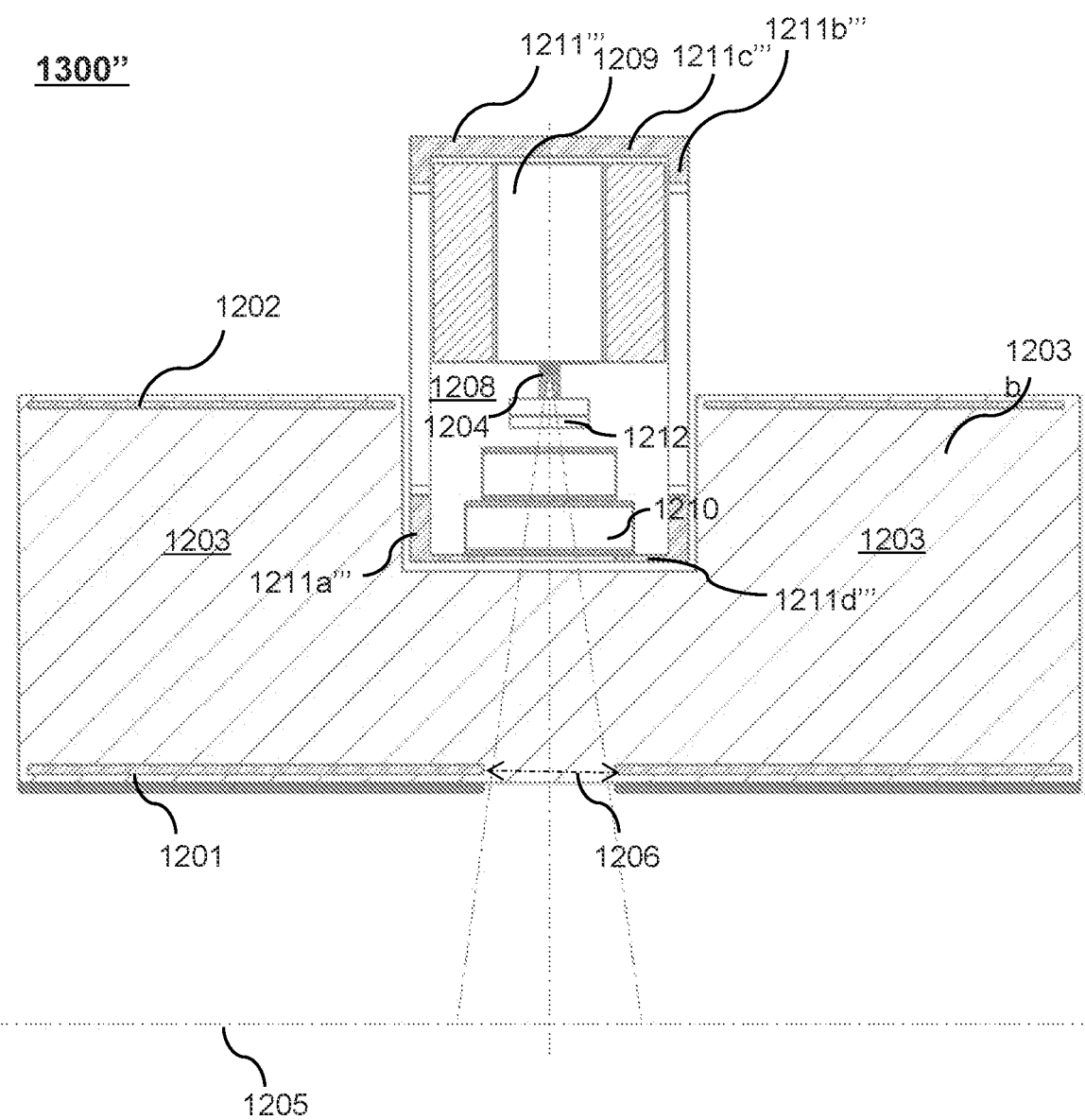
FIG. 13C shows an upper portion of a cross-sectional view of another exemplary therapeutic apparatus viewed along the X direction according to some embodiments of the present disclosure.

FIG. 13C shows an upper portion of a cross-sectional view of an exemplary therapeutic apparatus 1300" viewed along the X direction according to some embodiments of the present disclosure. Compared with the therapeutic apparatus 1300 described in FIG. 13A and the therapeutic apparatus 1300' described in FIG. 13B, the magnetic shielding structure 1211' of the therapeutic apparatus 1300" may surround the linear accelerator 1209, the collimator 1212, and the MLC 1210. As shown in FIG. 13C, the first side plate 1211a''' and the second side plate 1211b''' may at least stretch from the innermost radial position of the MLC 1210 to the outermost radial position of the linear accelerator 1209 along the radial direction. The downside plate 1211d''' may be located at the innermost side of the MLC 1210 and further provide at least one slot to allow the radiation beam produced by the linear accelerator 1209 to pass through.

Figure 14A:
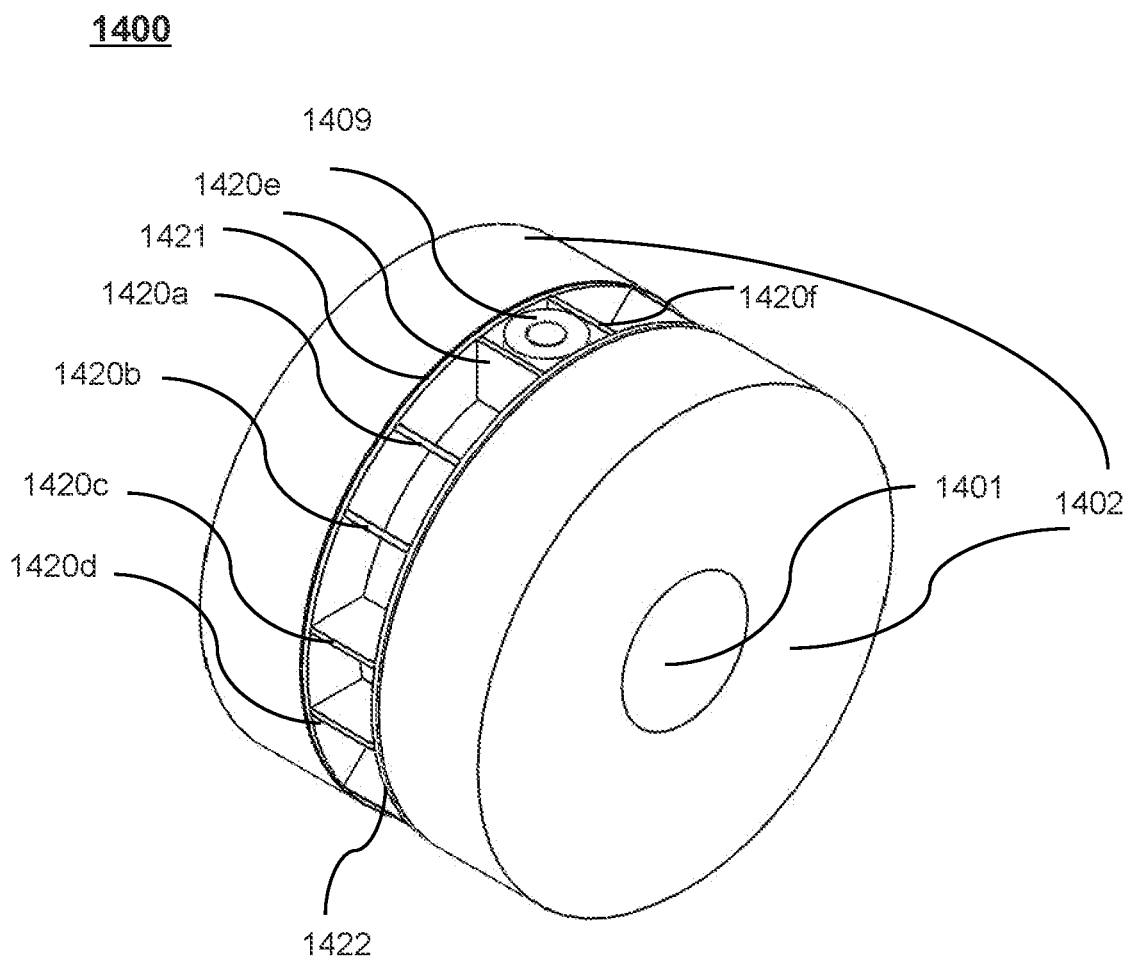
FIG. 14A shows a perspective view of an exemplary therapeutic apparatus according to some embodiments of the present disclosure.

FIG. 14A shows a perspective view of an exemplary therapeutic apparatus 1400 according to some embodiments of the present disclosure. The therapeutic apparatus 1400 may include a bore 1401, a magnetic body 1402 (similar to or same as a "cryostat"), a linear accelerator 1409, and a magnetic shielding arrangement. The magnetic shielding arrangement may include a first magnetic shielding layer 1421, a second magnetic shielding layer 1422, and a plurality of magnetic shielding separators (e.g., 1420a, 1420b, 1420c). The linear accelerator 1409, the bore 1401, and the magnetic body 1402 may be similar to the linear accelerator 409, 509, 609, 809, 1109, or 1209, the bore 301, or 801, and the magnetic body 302 and the descriptions are not repeated here.

As shown in FIG. 14A, the first magnetic shielding layer 1421 may be located between the linear accelerator 1409 and one chamber of the magnetic body 1402, and the second magnetic shielding layer 1422 may be located between the linear accelerator 1409 and the other chamber of the magnetic body 1402. The first magnetic shielding layer 1421 and the second magnetic shielding layer 1422 may have the same shape of an annulus. The first magnetic shielding layer 1421 and the second magnetic shielding layer 1422 may be parallel to each other and coaxial with the bore 1401. The outer diameter of the first magnetic shielding layer 1421 may be equal to or larger than that of the magnetic body 1402. The inner diameter of the first magnetic shielding layer 1421 may be larger than or equal to that of the magnetic body 1402. The difference between the outer diameter and the inner diameter of the annulus may be larger than or equal to the longitudinal length of the linear accelerator 1409.

Each of the plurality of magnetic shielding separators may be located between the first magnetic shielding layer 1421 and the second magnetic shielding layer 1422. Each of the plurality of magnetic shielding separators may connect the first magnetic shielding layer 1421 and the second magnetic shielding layer 1422. Every two adjacent magnetic shielding separators (e.g., the magnetic shielding separator 1420e and the magnetic shielding separator 1420f) may form a magnetic shielding structure with part of the first magnetic shielding layer 1421 and part of the second magnetic shielding layer 1422. The linear accelerator 1409 may be located within one of the magnetic shielding structures. Each magnetic shielding structure may have an opposite or opposing counterpart. Each magnetic shielding structure and its counterpart may be symmetrical about the axis of the bore 1401.

The plurality of magnetic shielding separators 1420 may be evenly or unevenly distributed between the first magnetic shielding layer 1421 and the second magnetic shielding layer 1422. In some embodiments, the number of the plurality of magnetic shielding separators 1420 may be a multiple of 2, forming an even-numbered magnetic shielding structures and thus reducing the field in-homogeneity caused by the presence of the plurality of magnetic shielding separators 1420.

As shown in FIG. 14A, the first magnetic shielding layer 1421, the second magnetic shielding layer 1422 and the plurality of magnetic shielding separators may form the similar magnetic shielding structures as the magnetic shielding structures described in FIG. 8A. For example, part of the first magnetic shielding layer 1421, part of the second magnetic shielding layer 1422, the magnetic shielding separator 1420f and the magnetic shielding separator 1420e may form a magnetic shielding structure similar to the magnetic shielding layer 811. The magnetic shielding separator 1420f and the magnetic shielding separator 1420e may provide the continuous pathway along the axial direction of the magnetic body 1402 for the magnetic field to pass through. As another example, part of the first magnetic shielding layer 1421, part of the second magnetic shielding layer 1422, the magnetic shielding separator 1420a and the magnetic shielding separator 1420b may form another magnetic shielding structure similar to the magnetic shielding layer 831a. As still another example, part of the first magnetic shielding layer 1421, part of the second magnetic shielding layer 1422, the magnetic shielding separator 1420c and the magnetic shielding separator 1420d may form another magnetic shielding structure similar to the magnetic shielding layer 831b.

Figure 14B:
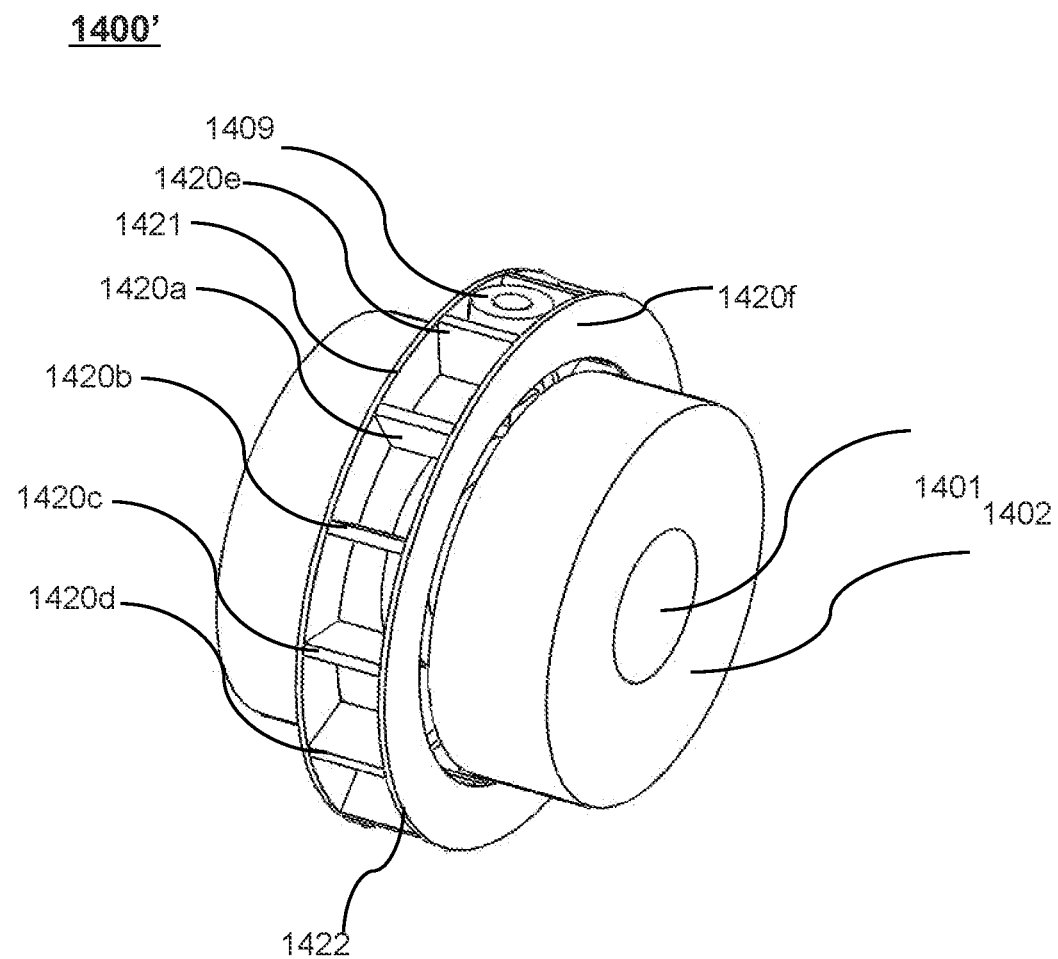
FIG. 14B shows a perspective view of another exemplary therapeutic apparatus according to some embodiments of the present disclosure.

FIG. 14B shows a perspective view of an exemplary therapeutic apparatus 1400' according to some embodiments of the present disclosure. Compared with the therapeutic apparatus 1400 described in FIG. 14A, at least part of the linear accelerator 1409 of the therapeutic apparatus 1400' may be located at the outside of the recess (not shown) along the radial direction of the magnetic body 1402. As shown in FIG. 14, the linear accelerator 1409 and the magnetic shielding arrangement may at least partially stretch out of the opening of the recess formed by the outer walls of the magnetic body 1402. Specifically, the first magnetic shielding layer 1421, the second magnetic shielding layer 1422, and the plurality of magnetic shielding separators (e.g., 1420*a*, 1420*b*, 1420*c*) may stretch out of the opening of the recess. In some embodiments, the linear accelerator 1409 and the magnetic shielding arrangement may be supported by or mounted to a gantry or a drum (e.g., the gantry 306 or the drum 312) that is capable of rotating around the axis of the magnetic body 1402.

Figure 15A:
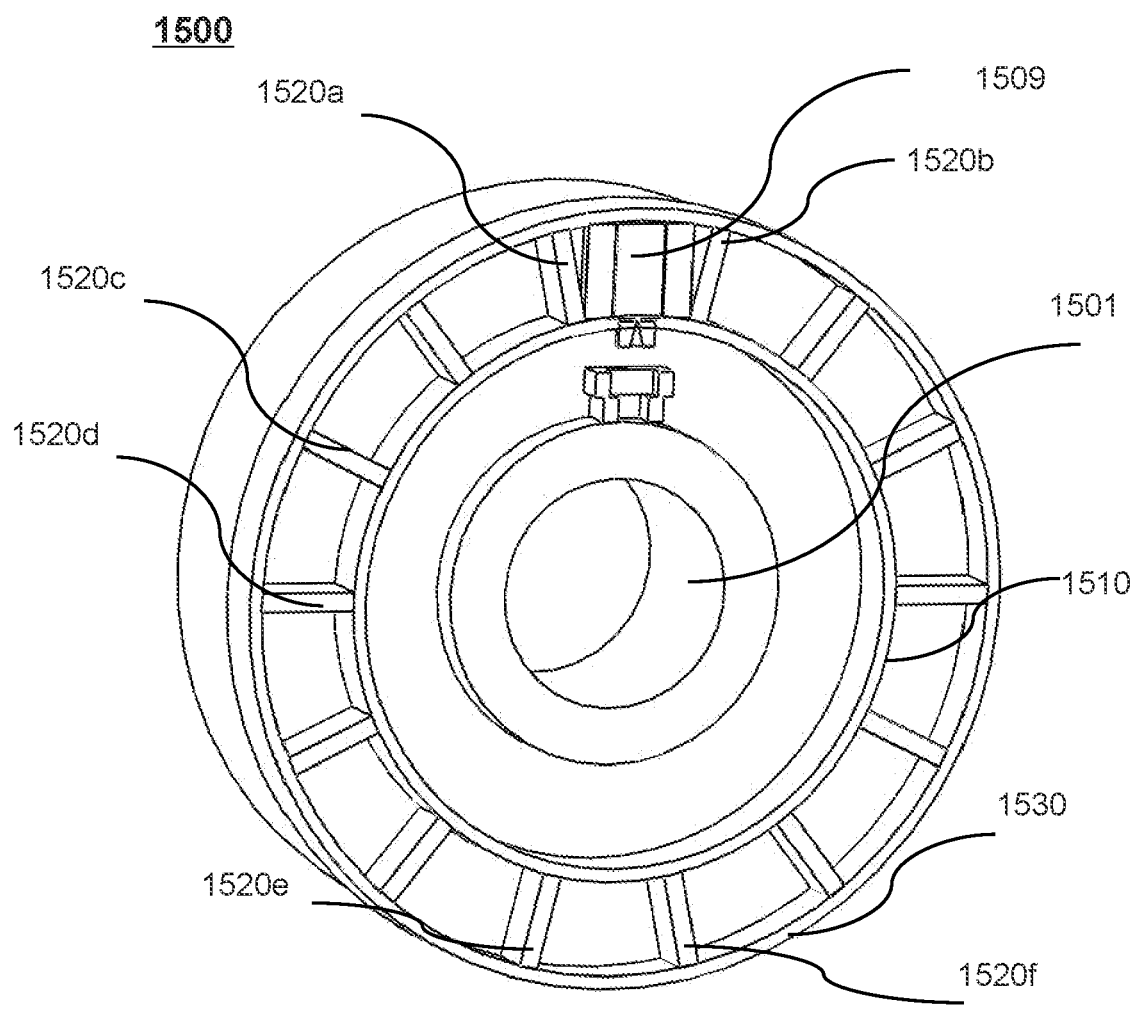
FIG. 15A shows a perspective view of a therapeutic apparatus according to some embodiments of the present disclosure.

FIG. 15A shows a perspective view of a therapeutic apparatus 1500 according to some embodiments of the present disclosure. The therapeutic apparatus 1500 may include a bore 1501, a linear accelerator 1509, and a magnetic shielding arrangement. The magnetic shielding arrangement may include a plurality of magnetic shielding separators (e.g., 1520*a*, 1520*b*, 1520*c*, 1520*d*, 1520*e*, 1520*f*), an inner magnetic shielding layer 1510 and an outer magnetic shielding layer 1530. The linear accelerator 1509 and the bore 1501 may be similar to the linear accelerator 809 and the bore 801 as described in FIG. 9A and the descriptions are not repeated here.

As shown in FIG. 15A, the inner magnetic shielding layer 1510 and the outer magnetic shielding layer 1530 may be two hollow cylinders sharing the same axis. For example, the inner magnetic shielding layer 1510, the outer magnetic shielding layer 1530 and the bore 1501 may form concentric circles when viewed along the axial direction of the bore 1501. The inner magnetic shielding layer 1510 and the outer magnetic shielding layer 1530 may be placed in a recess as described elsewhere in the present disclosure. The recess may be similar to the recess 408, 508, or 608 and be configured to accommodate the linear accelerator 1509. The inner magnetic shielding layer 1510 may be located at the innermost side of the recess and have a smaller radius than the outer magnetic shielding layer 1530.

Each of the plurality of magnetic shielding separators (e.g., 1520*a*, 1520*b*, 1520*c*, 1520*d*, 1520*e*, 1520*f*) may be located between the inner magnetic shielding layer 1510 and the outer magnetic shielding layer 1530. For example, each of the plurality of magnetic shielding separators may connect the outer surface of the inner magnetic shielding layer 1510 and the inner surface of the outer magnetic shielding layer 1530. The plurality of magnetic shielding separators may be radially arranged around the bore 1501. In some embodiments, each magnetic shielding separator may point to the center of the bore 1501. Every two adjacent magnetic shielding separators (e.g., the magnetic shielding separator 1520*a* and the magnetic shielding separator 1520*b*) may form a magnetic shielding structure with part of the inner magnetic shielding layer 1510 and part of the outer magnetic shielding layer 1530. The linear accelerator 1509 may be located within one of the magnetic shielding structure. Each magnetic shielding structure may have an opposite or opposing counterpart. Each separate space and its counterpart may be symmetrical about the axis of the bore 1501. The magnetic shielding structures formed by the plurality of magnetic shielding separators may be the same or different. For example, the plurality of magnetic shielding separators may be evenly distributed between the inner magnetic shielding layer 1510 and the outer magnetic shielding layer 1530, thus forming a plurality of uniform magnetic shielding structures.

As shown in FIG. 15A, when the linear accelerator 1509 is located inside the magnetic shielding structure formed by part of the inner magnetic shielding layer 1510, part of the outer magnetic shielding layer 1530, the magnetic shielding separator 1520*a* and the magnetic shielding separator 1520*b*, the magnetic field may be conducted by the inner magnetic shielding layer 1510, the outer magnetic shielding layer 1530, the magnetic shielding separator 1520*a* and/or the magnetic shielding separator 1520*b* and be kept from the linear accelerator 1509 located therebetween, thus achieving the magnetic shielding for the linear accelerator 1509. In some embodiments, in order to let through the radiation beam emitted from the linear accelerator 1509, the inner magnetic shielding layer 1510 may have one or more openings on the transmission path of the radiation beam.

In some embodiments, two more magnetic shielding layers similar to the magnetic shielding layer 1421 may be added to the magnetic shielding arrangement shown in FIG. 15A. For brevity, the first magnetic shielding layer 1421 and the second magnetic shielding layer 1422 described in FIG. 14A may be connected to the outer magnetic shielding layer 1530 at their outer sides, and be connected to the inner magnetic shielding layer 1510 at their inner sides. Each of the plurality of magnetic shielding separators may connect the first magnetic shielding layer 1421 and the second magnetic shielding layer 1422, forming a magnetic shielding structure whose cross-sectional view may be similar to that shown in FIG. 12A. The diameter of the outer magnetic shielding layer 1530 may be equal to or smaller than the outer diameter of the magnetic body 1402. The diameter of the inner magnetic shielding layer 1510 may be equal to or larger than the inner diameter of the magnetic body 1402. The difference between the diameter of the outer magnetic shielding layer 1530 and the diameter of the inner magnetic shielding layer 1510 may be larger than or equal to the longitudinal length of the linear accelerator 1509.

Figure 15B:
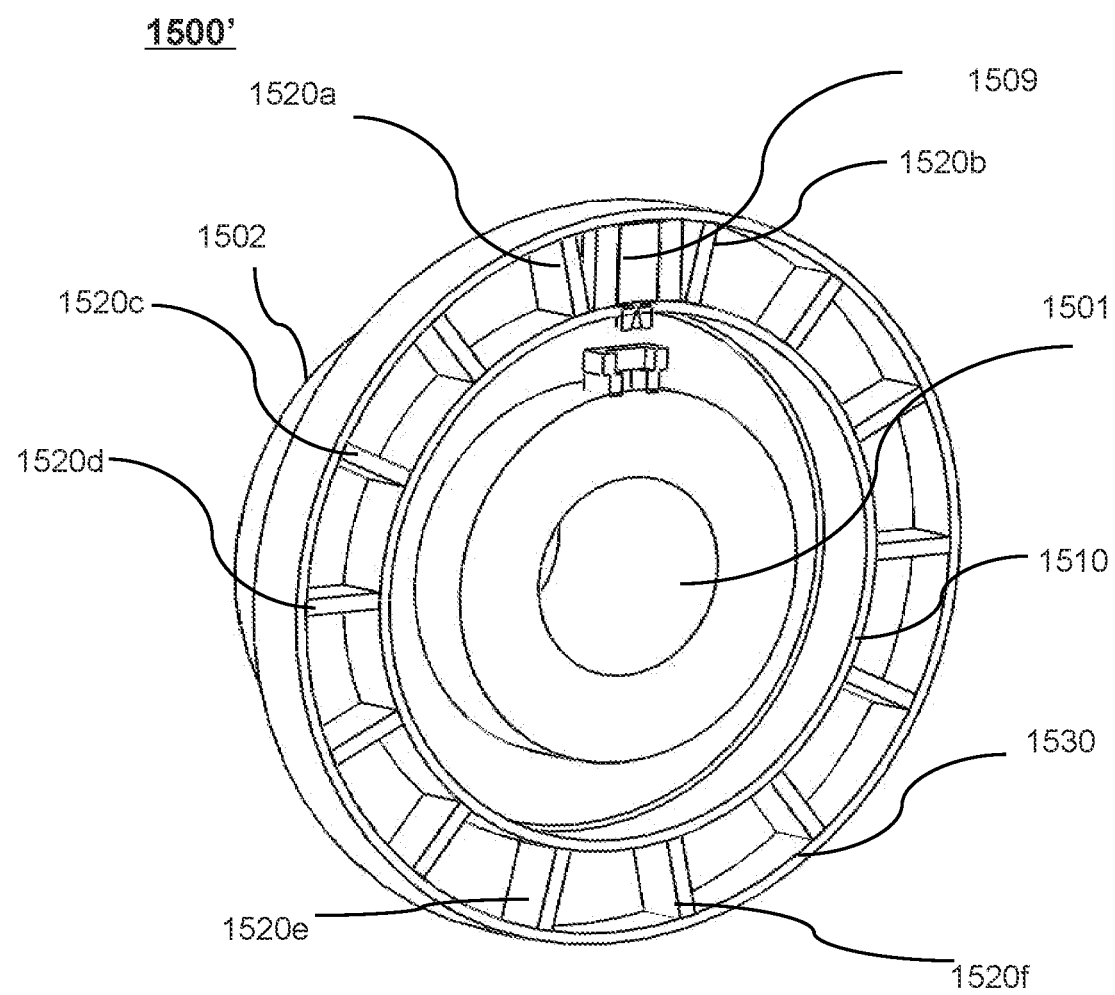
FIG. 15B shows a perspective view of a therapeutic apparatus according to some embodiments of the present disclosure.

FIG. 15B shows a perspective view of a therapeutic apparatus 1500' according to some embodiments of the present disclosure. Compared to the therapeutic apparatus 1500 described in FIG. 15A, at least part of the linear accelerator 1509 of the therapeutic apparatus 1500' may be located at the outside of the recess (not shown) along the radial direction of the magnetic body 1502. As shown in FIG. 15B, the linear accelerator 1509 and the magnetic shielding arrangement may at least partially stretch out of the recess formed by the outer walls of the magnetic body 1502. Specifically, the outer magnetic shielding layer 1530 may have a larger radius than that of the magnetic body 1502. The plurality of magnetic shielding separators (e.g., 1520*a*, 1520*b*, 1520*c*, 1520*d*, 1520*e*, 1520*f*) may stretch out of the opening of the recess. In some embodiments, the linear accelerator 1509 and the magnetic shielding arrangement may be supported by or mounted to a gantry or a drum (e.g., the gantry 306 or the drum 312) that is capable of rotating around the axis of the magnetic body 1502.

Figure 15C:
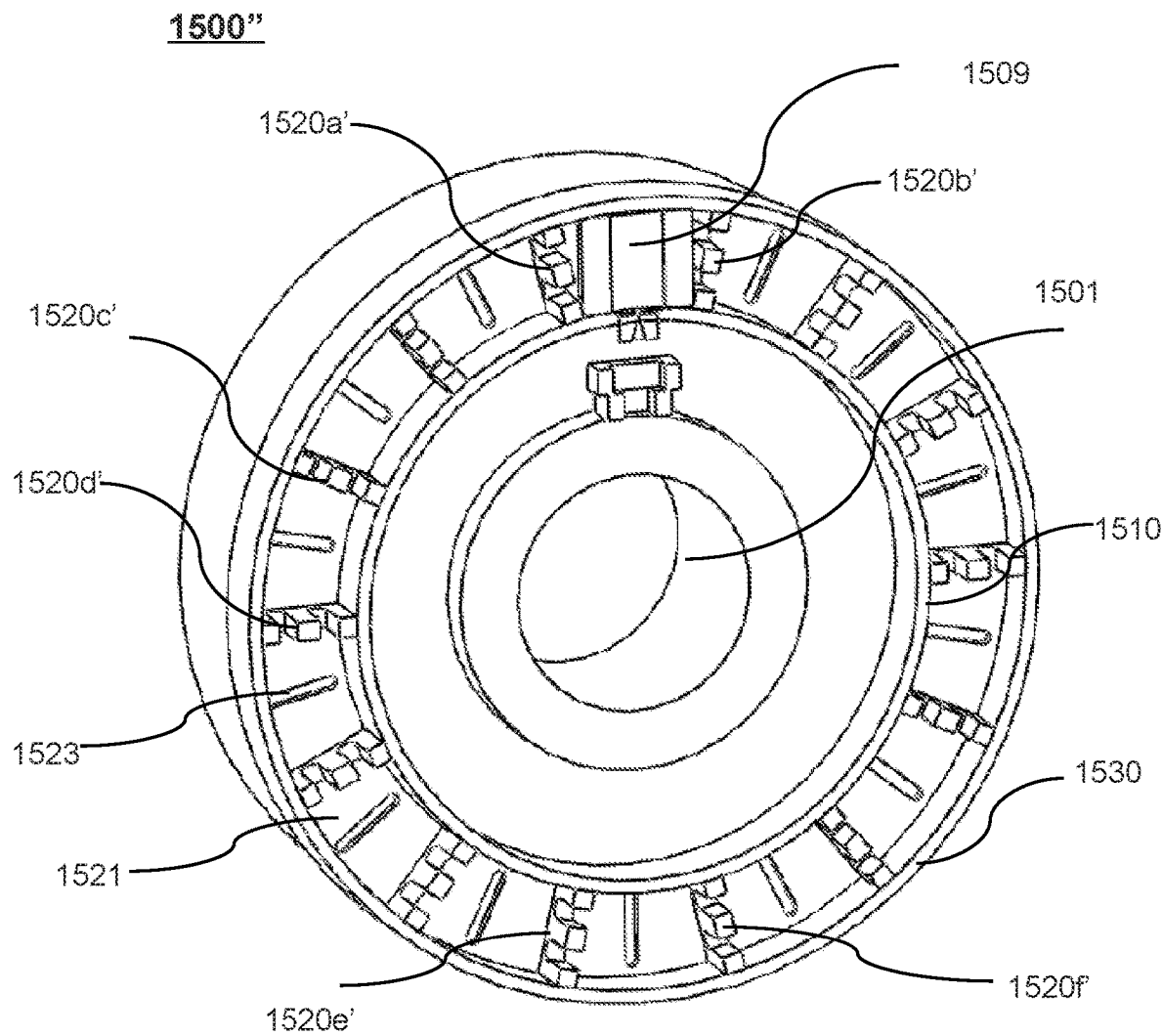
FIG. 15C shows a perspective view of another therapeutic apparatus according to some embodiments of the present disclosure.

FIG. 15C shows a perspective view of a therapeutic apparatus 1500" according to some embodiments of the present disclosure. Compared with the therapeutic apparatus 1500 described in FIG. 15A, the magnetic shielding separators of the therapeutic apparatus 1500" may have different configurations. Specifically, the magnetic shielding separator 1520*a*' may have the shape of a strip or a rod. A plurality of parallel strips or rods may be used to replace the magnetic shielding separator 1520 having the shape of a plate. The plurality of parallel strips or rods may connect the magnetic shielding layer 1521 located between the linear accelerator 1509 and one chamber of the cryostat (not shown) and another magnetic shielding layer (not shown) located between the linear accelerator 1509 and the other chamber of the cryostat. It shall be noted that the number of the strips or rods at each circumferential position of the cryostat can be any suitable integer, such as, 2, 3, 4, etc. The plurality of parallel strips or rods may also provide the continuous pathway along the axial direction of the bore 1501 for the magnetic field to pass through.

The magnetic shielding layer 1521 may further have a plurality of slots on it. Each slot may have the shape of a rectangle, an ellipse, or the like. Alternatively, the plurality of slots may point to the axis of the bore 1501. The plurality of slots may help better dissipate the heat produced by the MRI apparatus and/or the radiation therapy apparatus. When the slot is provided between the magnetic shielding separator 1520*a*' and the magnetic shielding separator 1520*b*', the magnetic shielding structure may have a cross-section similar to that shown in FIG. 13A.

Figure 15D:
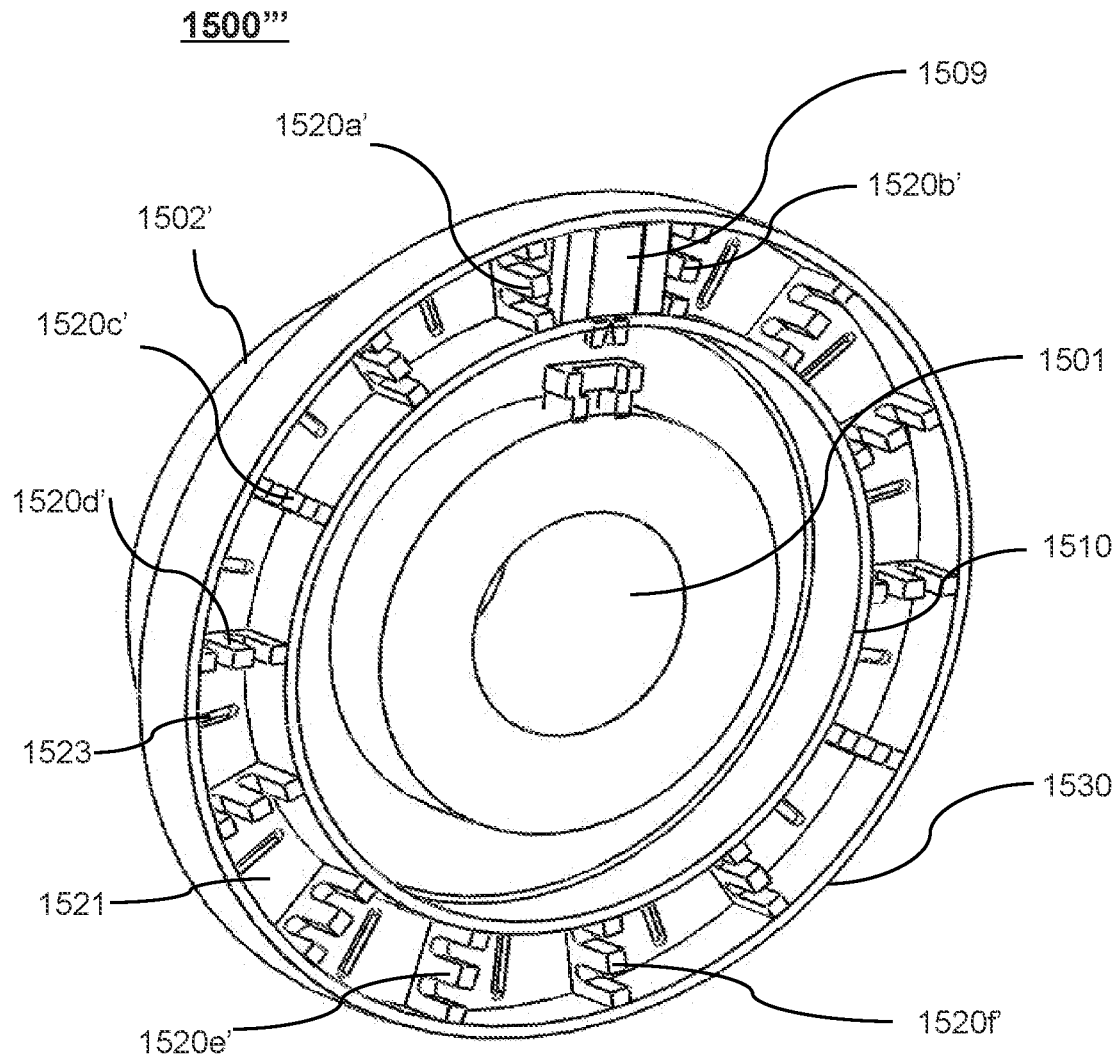
FIG. 15D shows a perspective view of a therapeutic apparatus according to some embodiments of the present disclosure.

FIG. 15D shows a perspective view of a therapeutic apparatus 1500''' according to some embodiments of the present disclosure. Compared to the therapeutic apparatus 1500'' described in FIG. 15C, at least part of the linear accelerator 1509 of the therapeutic apparatus 1500''' may be located at the outside of the recess (not shown) along the radial direction of the magnetic body 1502'. As shown in FIG. 15D, the linear accelerator 1509 and the magnetic shielding arrangement may at least partially stretch out of the recess formed by the outer walls of the magnetic body 1502'. Specifically, the outer magnetic shielding layer 1530' may have a larger radius than that of the magnetic body 1502'. The plurality of magnetic shielding separators (e.g., 1520*a*', 1520*b*', 1520*c*', 1520*d*', 1520*e*', 1520*f*') may stretch out of the opening of the recess. In some embodiments, the linear accelerator 1509 and the magnetic shielding arrangement may be supported by or mounted to a gantry or a drum (e.g., the gantry 306 or the drum 312) that is capable of rotating around the axis of the magnetic body 1502'.

Figure 16A:
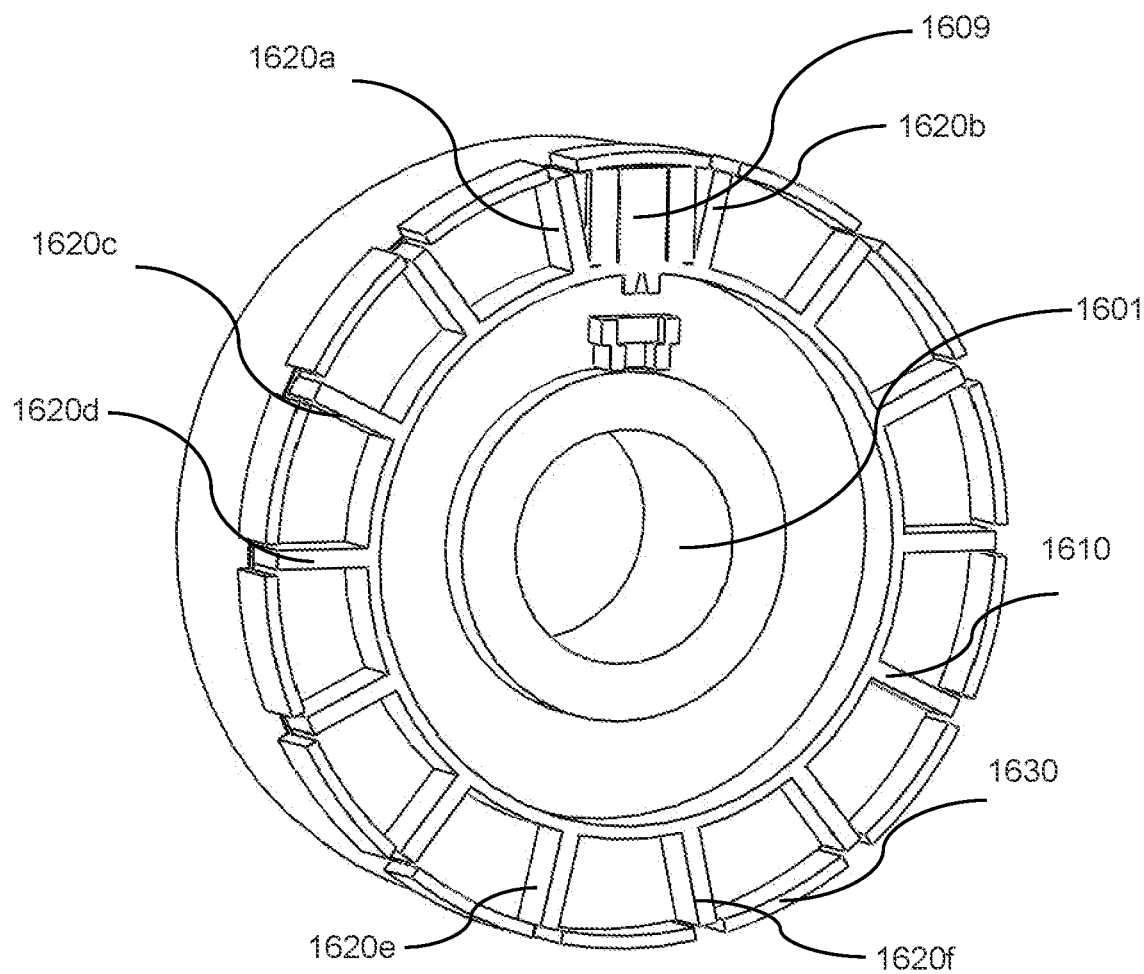
FIG. 16A shows a perspective view of an exemplary therapeutic apparatus according to some embodiments of the present disclosure.

FIG. 16A shows a perspective view of an exemplary therapeutic apparatus 1600 according to some embodiments of the present disclosure. The therapeutic apparatus 1600 may include a bore 1601, a linear accelerator 1609, and a magnetic shielding arrangement. The magnetic shielding arrangement may include a plurality of magnetic shielding separators (e.g., 1620*a*, 1620*b*, 1620*c*, 1620*d*, 1620*e*, 1620*f*), an inner magnetic shielding layer 1610, and an outer magnetic shielding layer 1630. The inner magnetic shielding layer 1610, the plurality of magnetic shielding separators (i.e., 1620*a*, 1620*b*, 1620*c*, 1620*d*, 1620*e*, 1620*f*), the linear accelerator 1609, and the bore 1601 may be similar to the inner magnetic shielding layer 1510, the plurality of magnetic shielding separators (i.e., 1520*a*, 1520*b*, 1520*c*, 1520*d*, 1520*e*, 1520*f*), the linear accelerator 1509, and the bore 1501, and the descriptions are not repeated here.

Unlike the outer magnetic shielding layer 1530, the outer magnetic shielding layer 1630 may not be continuous. As shown in FIG. 16A, the outer magnetic shielding layer 1630 may have a plurality of slots at the contact surfaces of the outer magnetic shielding layer 1630 and the plurality of magnetic shielding separators. The width of each slot along the circumferential direction may be equal to or larger than the thickness of the magnetic shielding separator. The plurality of slots may help better dissipate the heat produced by the MRI apparatus and/or the radiation therapy apparatus. Further, the plurality of slots may also be good for cable layout. In some embodiments, similar slots may also exist in the inner magnetic shielding layer 1610 for the same purposes.

Figure 16B:
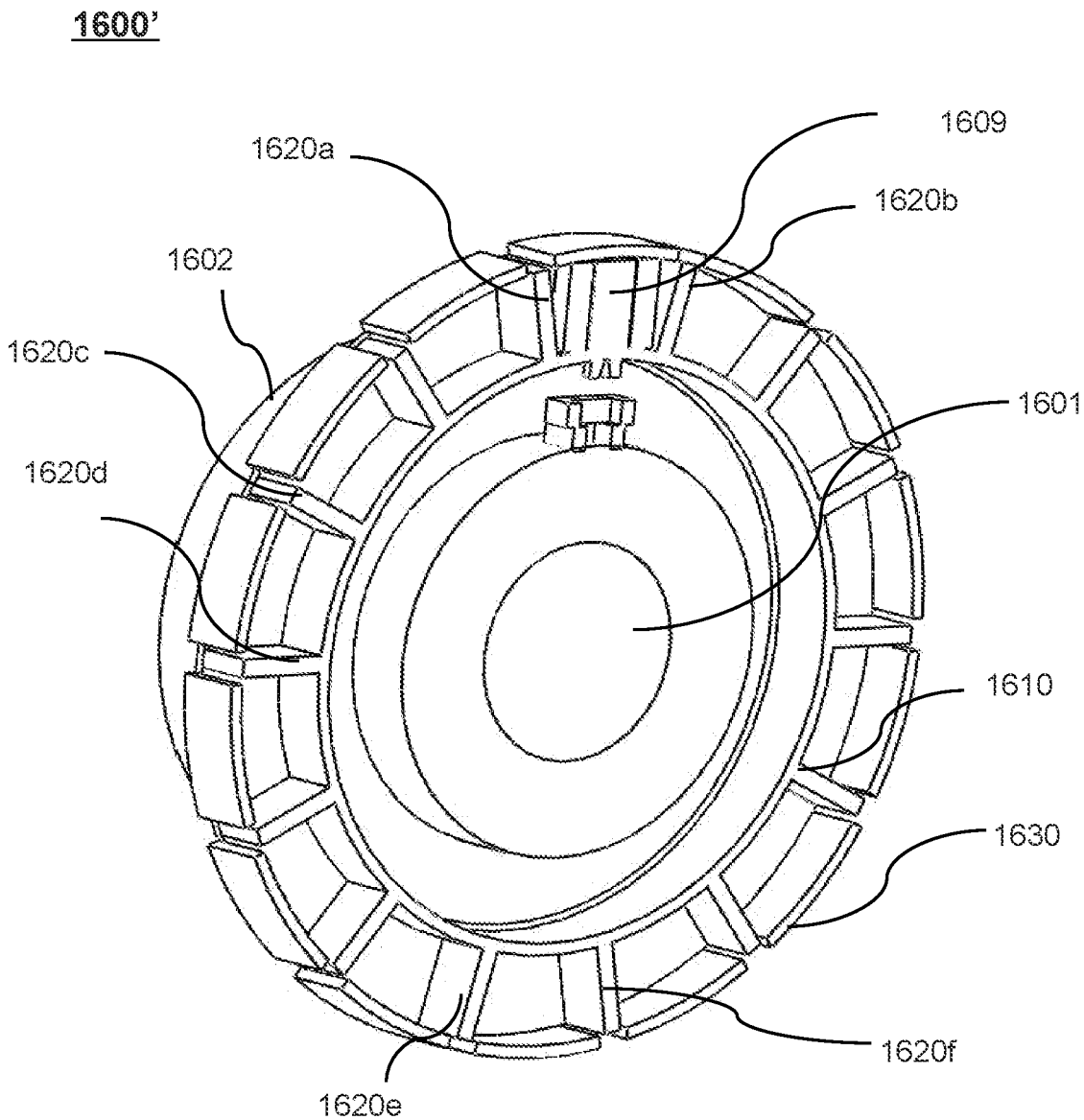
FIG. 16B shows a perspective view of a therapeutic apparatus according to some embodiments of the present disclosure.

FIG. 16B shows a perspective view of a therapeutic apparatus 1600' according to some embodiments of the present disclosure. Compared to the therapeutic apparatus 1600 described in FIG. 16A, at least part of the linear accelerator 1609 of the therapeutic apparatus 1600' may be located at the outside of the recess (not shown) along the radial direction of the magnetic body 1602. As shown in FIG. 16B, the linear accelerator 1609 and the magnetic shielding arrangement may at least partially stretch out of the recess formed by the outer walls of the magnetic body 1602. Specifically, the outer magnetic shielding layer 1630 may have a larger radius than that of the magnetic body 1602. The plurality of magnetic shielding separators (e.g., 1620*a*, 1620*b*, 1620*c*, 1620*d*, 1620*e*, 1620*f*) may stretch out of the opening of the recess. In some embodiments, the linear accelerator 1609 and the magnetic shielding arrangement may be supported by or mounted to a gantry or a drum (e.g., the gantry 306 or the drum 312) that is capable of rotating around the axis of the magnetic body 1602.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A radiation therapy system comprising:
    a magnetic resonance imaging (MRI) apparatus configured to acquire MRI data with respect to a region of interest (ROI), the MRI apparatus including:
    an annular cryostat, the annular cryostat including at least one outer wall and at least one inner wall coaxial around an axis of the annular cryostat;
    a radiation therapy apparatus configured to apply therapeutic radiation to at least one portion of the ROI, the radiation therapy apparatus including:
        a linear accelerator configured to accelerate electrons in an electron beam to produce a photon beam of the therapeutic radiation, at least a portion of the linear accelerator being located within a recess of the MRI apparatus; and
        a first shielding structure configured to provide magnetic shielding for at least one of the linear accelerator and the one or more collimation components; and
    the recess between the at least one outer wall and the at least one inner wall of the annular cryostat, the recess has an opening formed on the at least one outer wall, and the at least a portion of the linear accelerator stretches out of the opening, wherein the at least a portion of the linear accelerator is surrounded by at least a portion of the first shielding structure, the at least a portion of the first shielding structure surrounding the at least a portion of the linear accelerator is located within the recess of the MRI apparatus, and the first shielding structure provides passive magnetic shielding for the linear accelerator.

2. The radiation therapy system of claim 1, wherein the first shielding structure forms a semi-closed loop around an axis of the linear accelerator.

3. The radiation therapy system of claim 1, wherein the radiation therapy apparatus further includes two annular magnetic shielding layers, and the first shielding structure is at least formed by two first magnetic shielding separators connecting the two annular magnetic shielding layers.

4. The radiation therapy system of claim 3, wherein the two annular magnetic shielding layers are coaxial around the axis of the annular cryostat.

5. The radiation therapy system of claim 4, wherein the two annular magnetic shielding layers are arranged along the axis of the annular cryostat and parallel to each other.

6. The radiation therapy system of claim 5, wherein the radiation therapy apparatus further includes an inner magnetic shielding layer and an outer magnetic shielding layer, both of which are connected to the two annular magnetic shielding layers, and the first shielding structure is formed by the two annular magnetic shielding layers, the inner magnetic shielding layer, the outer magnetic shielding layer, and the two first magnetic shielding separators connecting the two annular magnetic shielding layers.

7. The radiation therapy system of claim 6, wherein the outer magnetic shielding layer includes a plurality of slots, and at least one of the plurality of slots is located at a position corresponding to one of the two first magnetic shielding separators.

8. The radiation therapy system of claim 1, wherein electron beam moves along an electron beam path that is parallel to the axis of the annular cryostat, and the radiation therapy apparatus further includes:
    a target; and
    a beam deflection unit configured to deflect the electrons from the electron beam onto the target to produce the photon beam of the therapeutic radiation.

9. The radiation therapy system of claim 1, wherein the annular cryostat includes:
    an annular concave structure; and
    the radiation therapy apparatus further includes:
        a multi-leaf collimator (MLC) accommodated in the annular concave structure of the annular cryostat and configured to control a shape of the photon beam of the therapeutic radiation that passes through it.

10. The radiation therapy system of claim 9, wherein one or more of the plurality of main magnetic coils are arranged to surround the annular concave structure, and the one or more of the plurality of main magnetic coils have a larger radius from the axis than the rest of the plurality of main magnetic coils.

11. The radiation therapy system of claim 9, wherein the MLC is connected to the linear accelerator via two or more rods.

12. The radiation therapy system of claim 9, wherein the MLC is configured to move within the annular concave structure along a sliding structure.

13. The radiation therapy system of claim 1, wherein the recess is an annular recess.

14. The radiation therapy system of claim 13, the radiation therapy apparatus further including at least one second shielding structure, wherein the first shielding structure and the at least one second shielding structure are respectively located at selected circumferential locations within the annular recess.

15. The radiation therapy system of claim 14, wherein the at least one second shielding structure is located at an opposite circumferential position of the first shielding structure with respect to the axis of the annular cryostat.

16. The radiation therapy system of claim 14, wherein the at least one second shielding structure includes more than two second shielding structures, and the first shielding structure and the at least one second shielding structure are evenly distributed within the annular recess.

17. The radiation therapy system of claim 13, wherein the annular cryostat includes at least two chambers and a neck portion, the at least two chambers being connected through the neck portion and in fluid communication with each other, the annular recess being defined at least in part by the at least two chambers and the neck portion.

18. The radiation therapy system of claim 17, wherein the annular recess is located between the at least two chambers, and an outermost surface of the neck portion forms an innermost boundary of the annular recess.

19. The radiation therapy system of claim 1, wherein the first shielding structure is continuously distributed along a direction of the axis of the annular cryostat and stretches to cover two ends of the linear accelerator along the direction of the axis of the annular cryostat.

* * * * *